US008684947B2

(12) United States Patent
Eide

(10) Patent No.: US 8,684,947 B2
(45) Date of Patent: Apr. 1, 2014

(54) METHOD FOR PROCESSING OF CONTINUOUS PRESSURE-RELATED SIGNALS DERIVABLE FROM A HUMAN OR ANIMAL BODY OR BODY-CAVITY

(75) Inventor: Per Kristian Eide, Oslo (NO)

(73) Assignee: DPCOM AS, Oslo (NO)

( * ) Notice: Subject to any disclaimer, the term of this patent is extended or adjusted under 35 U.S.C. 154(b) by 1305 days.

(21) Appl. No.: 12/289,308

(22) Filed: Oct. 24, 2008

(65) Prior Publication Data

US 2009/0124910 A1    May 14, 2009

Related U.S. Application Data

(62) Division of application No. 10/895,387, filed on Jul. 21, 2004, now Pat. No. 7,635,338.

(51) Int. Cl.
*A61B 5/00* (2006.01)
*A61B 5/02* (2006.01)

(52) U.S. Cl.
USPC .......................................... 600/561; 600/485

(58) Field of Classification Search
USPC ................................................. 600/485–503
See application file for complete search history.

(56) References Cited

U.S. PATENT DOCUMENTS

| 4,014,320 A | 3/1977 | Richards |
| 2002/0095087 A1 | 7/2002 | Mourad et al. |
| 2003/0032915 A1 | 2/2003 | Saul |
| 2003/0100845 A1* | 5/2003 | Eide ................ 600/561 |
| 2003/0216666 A1 | 11/2003 | Ericson et al. |
| 2004/0087863 A1 | 5/2004 | Eide |
| 2005/0177047 A1* | 8/2005 | Harpas et al. ......... 600/485 |
| 2006/0167360 A1 | 7/2006 | Bennett et al. |
| 2006/0206021 A1 | 9/2006 | Diab |

FOREIGN PATENT DOCUMENTS

| FR | 2 725 610 A1 | 4/1996 |
| WO | WO-97/09927 A2 | 3/1997 |
| WO | WO-02/062215 A2 | 8/2002 |

* cited by examiner

*Primary Examiner* — Michael Kahelin
*Assistant Examiner* — Karen Toth
(74) *Attorney, Agent, or Firm* — Birch, Stewart, Kolasch & Birch, LLP

(57) ABSTRACT

This invention describes a method for processing pressure signals derivable from locations inside or outside a human or animal body or body cavity. Different aspects of the invention relate to a method for optimal differentiating between cardiac beat- and artifact-induced pressure waves, a method for obtaining new and improved information from said pressure signals, a method for obtaining signals predicting pressures inside a body or body cavity from pressure signals outside said body or body cavity. In particular, this invention describes a method for modifying individual continuous non-invasive pressure-related signals into signals highly predictable of the corresponding invasive pressure-related signals based on already established relationships that can be used for formula-based adjustments of individual signals solely obtained by a non-invasive approach.

23 Claims, 17 Drawing Sheets

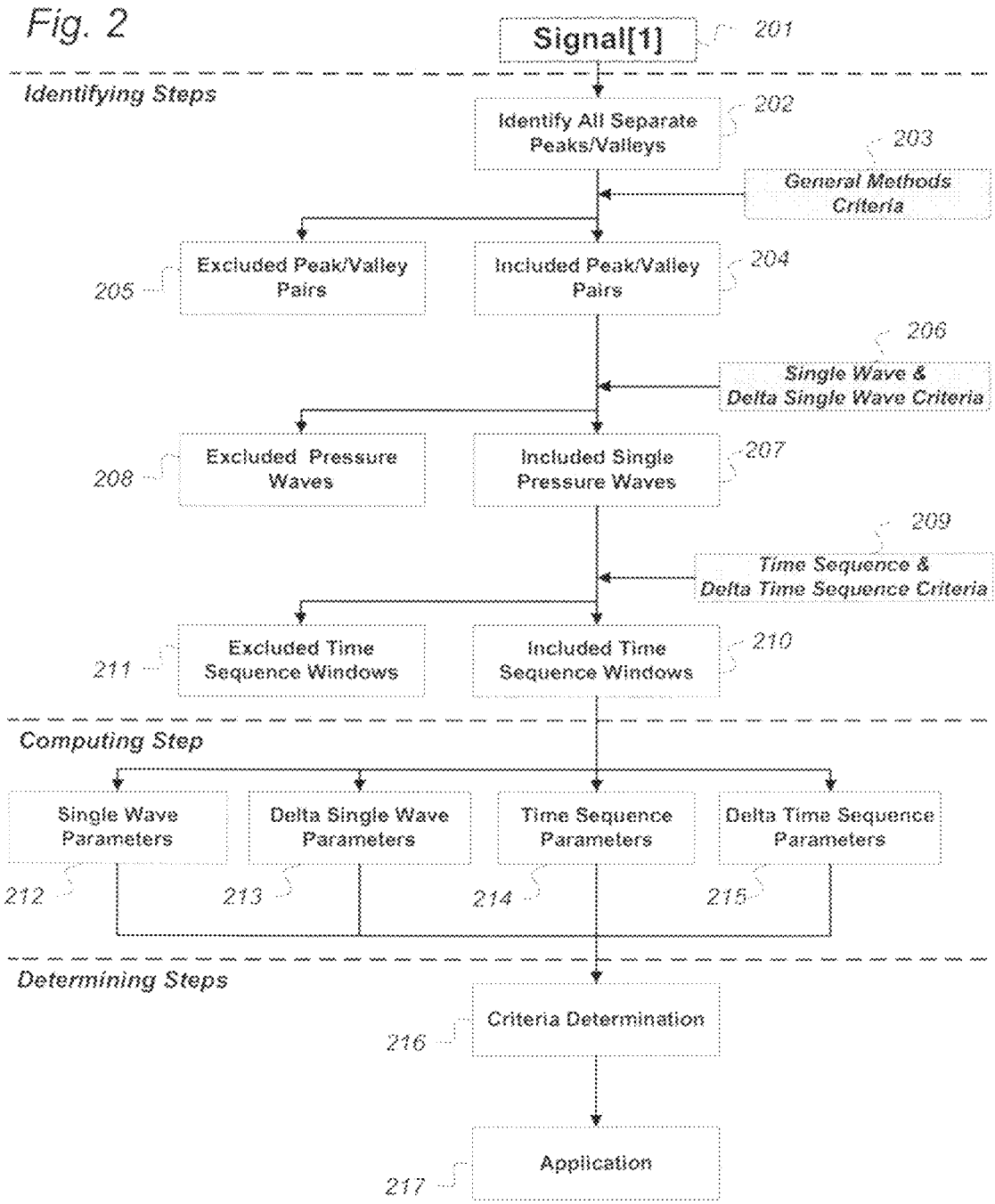

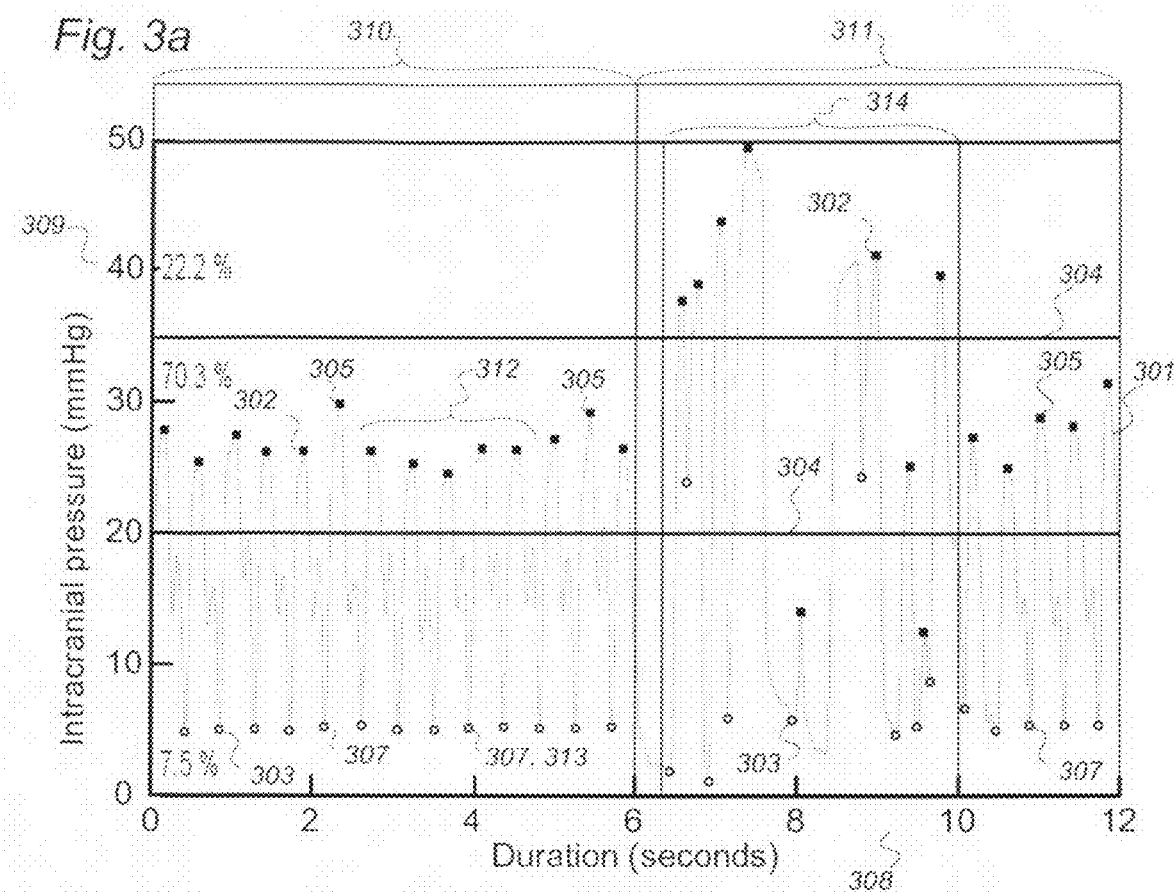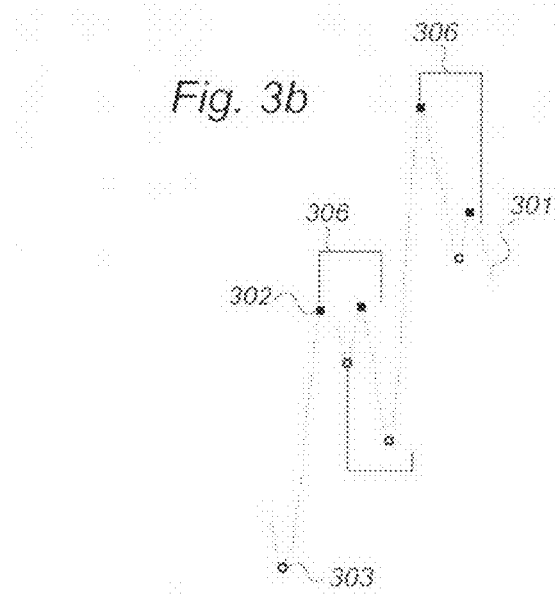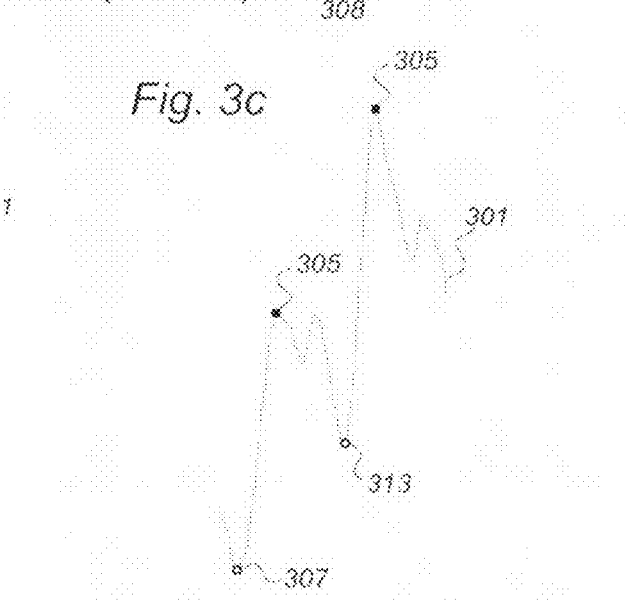

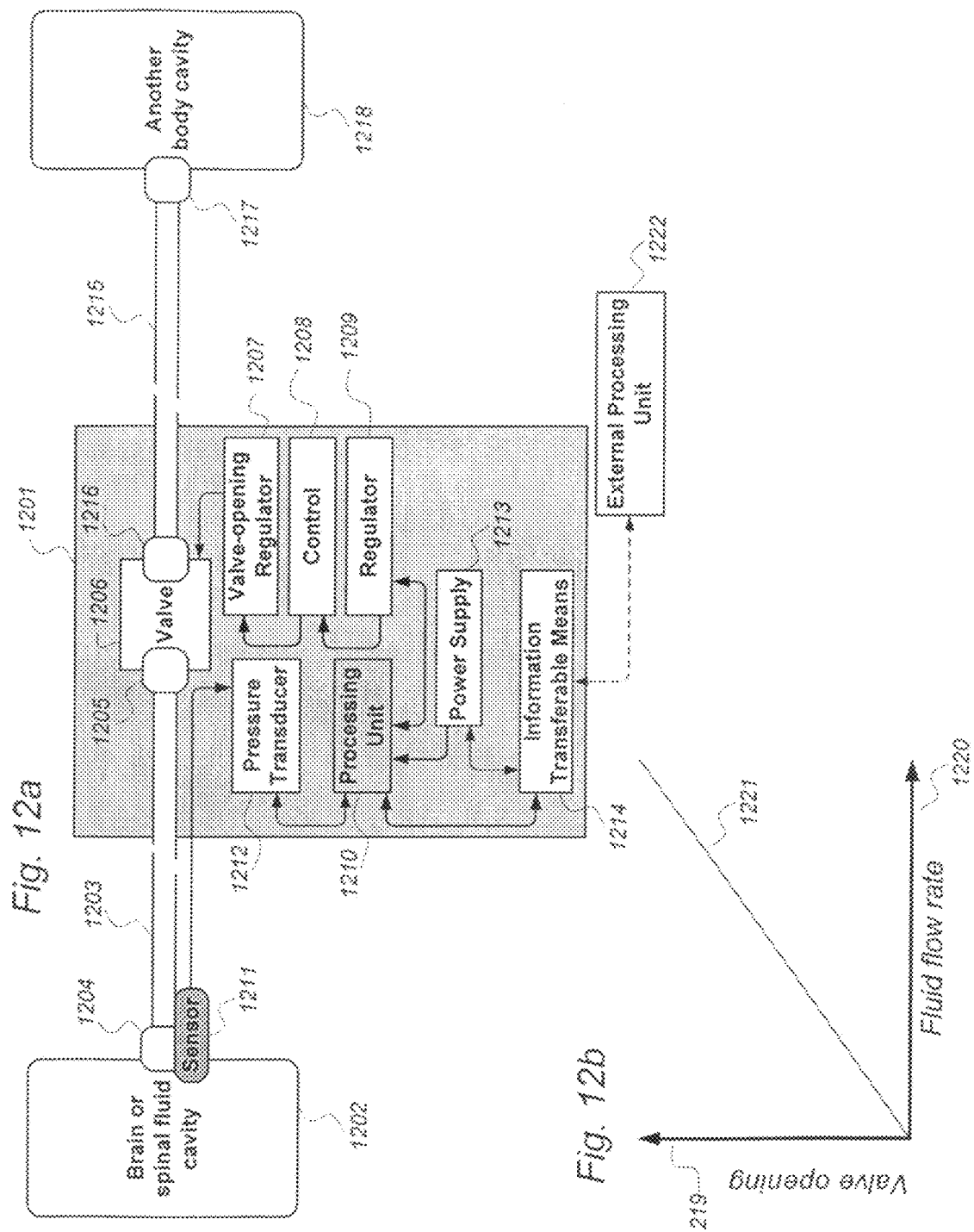

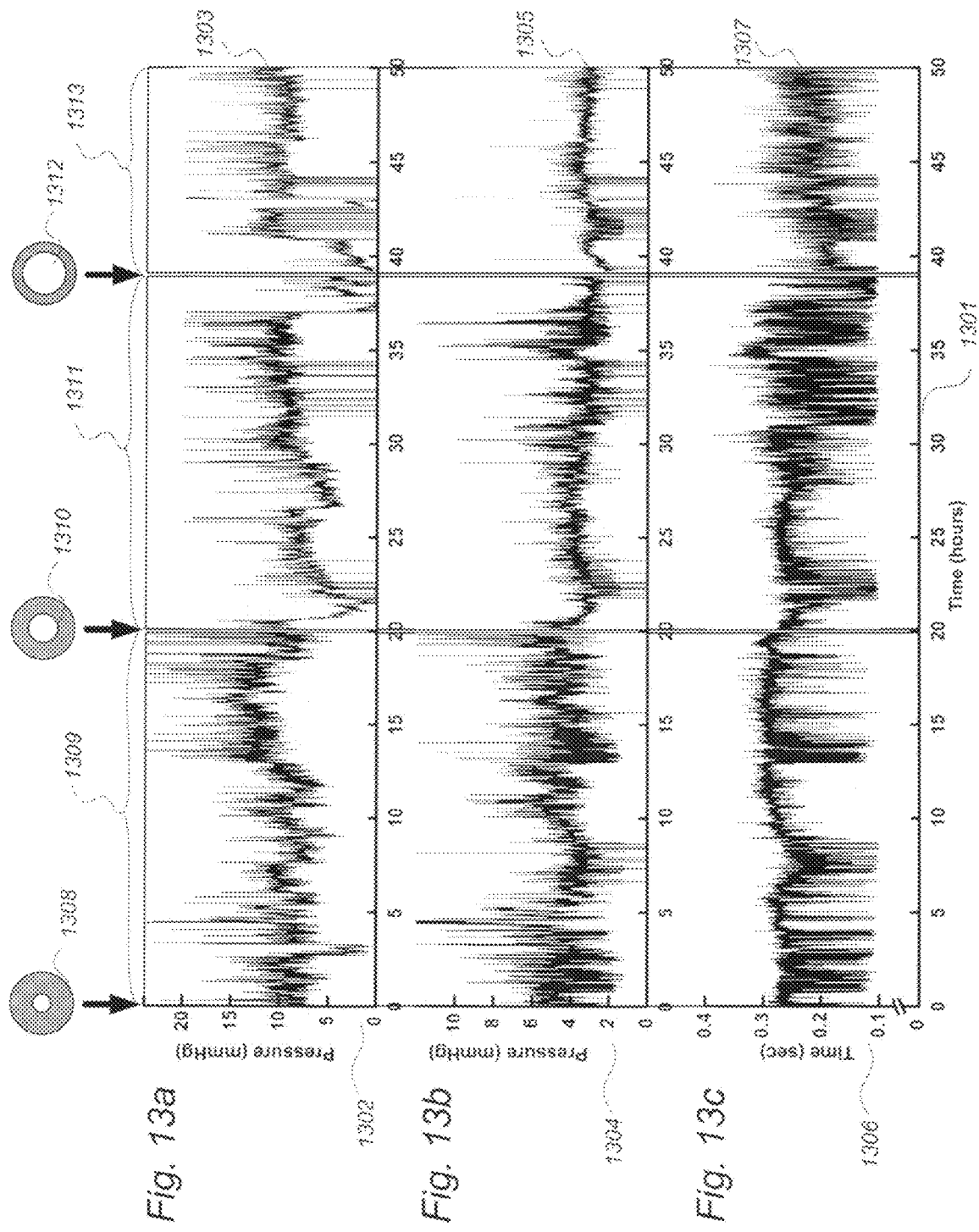

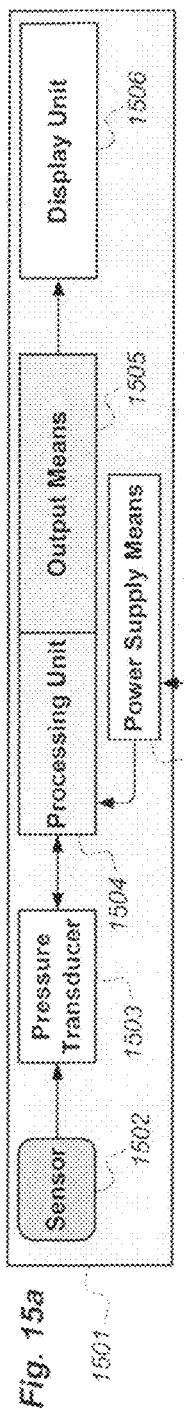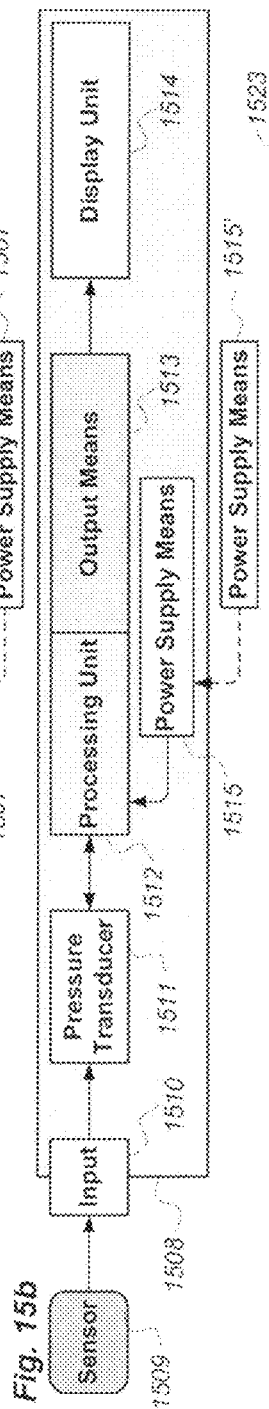

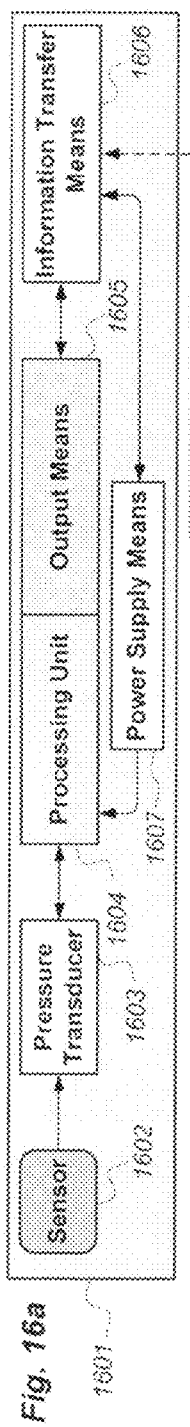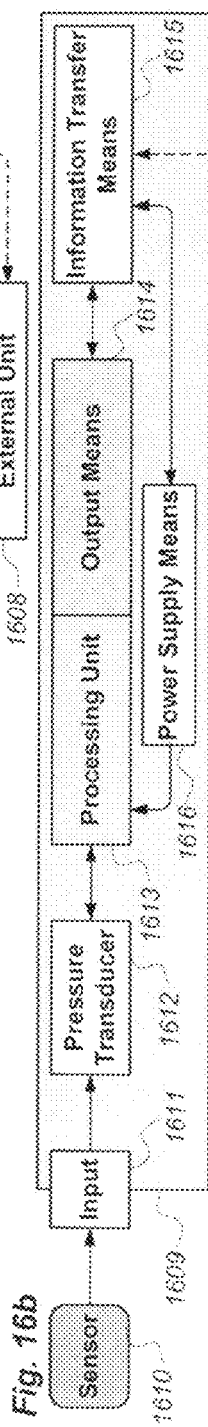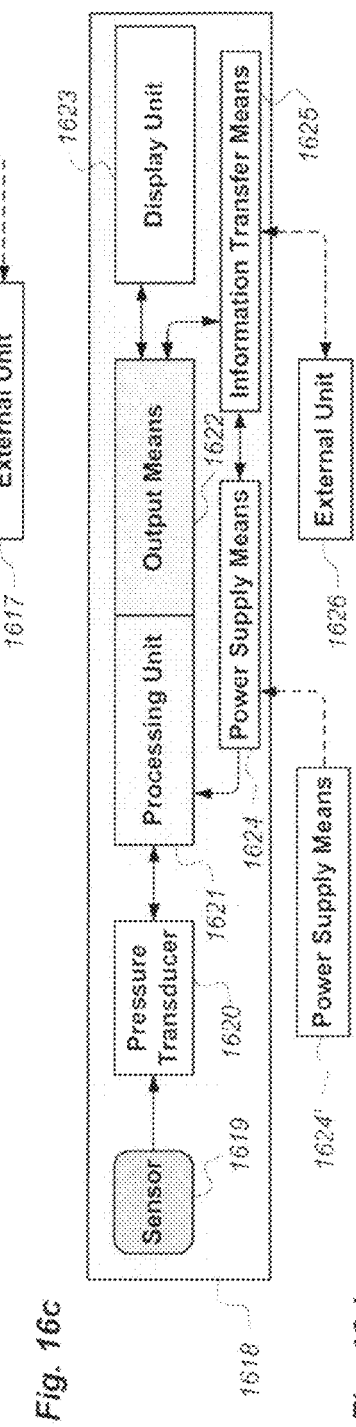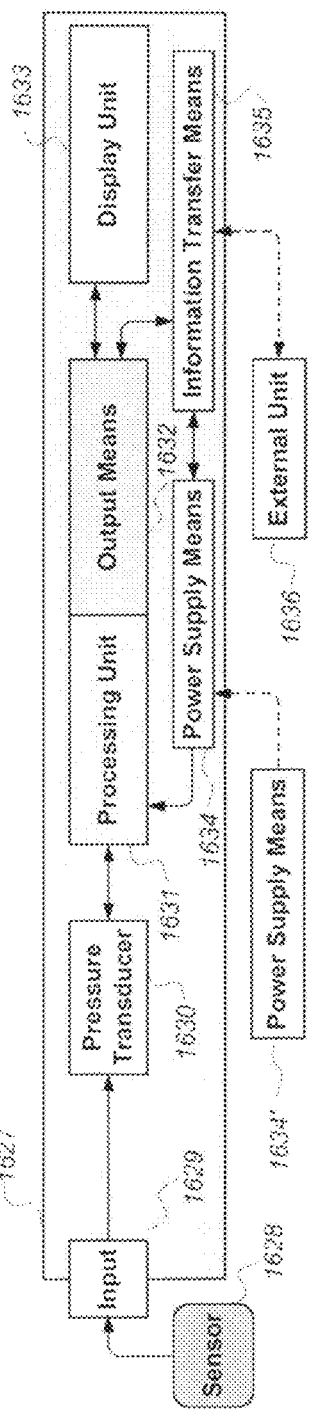
Fig. 16a
Fig. 16b
Fig. 16c
Fig. 16d

METHOD FOR PROCESSING OF CONTINUOUS PRESSURE-RELATED SIGNALS DERIVABLE FROM A HUMAN OR ANIMAL BODY OR BODY-CAVITY

CROSS REFERENCE TO RELATED APPLICATIONS

This application is a Divisional of application Ser. No. 10/895,387, filed on Jul. 21, 2004 now U.S. Pat. No. 7,635,338, the entire contents of which are hereby incorporated by reference and for which priority is claimed under 35 U.S.C. §120.

BACKGROUND OF THE INVENTION

1. Field of the Invention

Continuous monitoring of pressures from a human or animal body or body cavity requires some kind of processing of the pressure measurements. Pressure measurements within a human being or animal are created from pressure waves created by the cardiac beats, though this fact is not necessarily taken into account when measuring human or animal pressures. Pressure measurements may be derived from inside or outside a human or animal body or body cavity. It may be preferable to place a pressure sensor outside a body or body cavity, but the problem is to obtain reliable pressure measurements from such sensor locations. Depending on the type of such pressure measurements, signals related to pressure measurements may be garbled with noise, and the pressure difference from inside to outside the body cavity may be unknown. Pressure monitoring may have a more widespread role than reflected by the current and existing use. For example, various types of fluid flow valves are used to drain excess fluid from a body cavity such as a human brain or spinal fluid body cavity. Related to the function of such valve devices, pressure monitoring has no or a minimal place.

2. Related Art

Continuous pressure monitoring has a widespread use concerning arterial blood pressure monitoring, ocular bulb pressure monitoring, intracranial pressure monitoring, lumbar cerebrospinal fluid pressure monitoring, urinary tract pressure monitoring, and gastrointestinal tract pressure monitoring. Depending on how pressure measurements are performed, continuous pressure signals may be obtained. Most current and existing technologies solely use analogue signals, though modern data technology allows such analogue signals to be converted into digital data signals. Some kind of signal processing may be applied to analogue as well as digital pressure signals.

Though monitoring of pressures within a human body or body cavity has been used for many decades, it is still unclear how pressure measurements should be processed to give best possible information from said measurements. It is well known that pressures have a static component (mean pressure) and a dynamic component (pulse pressure), related to the fact that pressure waves within a human or animal body or body cavity are created by cardiac beat-induced pressure waves. During pressure monitoring usually the static component is assessed whereas the role of the dynamic component is unclear. Technologies (e.g. by using fast Fourier transformation of pressure signals) that measure the dynamic component of pressure measurements give no or minimal control as to whether the dynamic pressure changes are related to cardiac beat-induced pressure waves or not.

Continuous pressure signals are processed by computation of mean pressure, usually computed as the sum of pressure levels divided by the numbers of samples. It is not possible to evaluate whether said mean pressure is related to cardiac beat-induced pressure waves or not. According to current and prior art technology, evaluation whether pressure measurements are associated with cardiac beat-induced pressure waves is based on visual inspection of the pressure wave, or by inspection whether diastolic and systolic pressure values are different. Such evaluation may be very user-dependent and misleading. For practical purposes, continuous inspection of a pressure waveform during pressure monitoring is impossible. Furthermore, waveform analysis according to prior art technology (e.g. fast Fourier analysis or modifications thereof), does not allow assessment whether pressure waves are related to cardiac beats or not. Given bad signal quality such types of analyses can be very misleading. The inventor previously has described a method for processing continuous pressure signals in the following patent application: U.S. Ser. No. 10/283,245; U.S. Ser. No. 10/613,112; PCT/NO02/00164; and PCT/NO03/0029.

During pressure measurements it is preferable to use non-invasive sensors. The term non-invasive refers to the fact that the skin does not need to be penetrated to measure pressure within a body or body cavity. There are numerous examples of non-invasive pressure monitoring. Placing a device on the skin, thereby sensing the arterial blood pressure within the body tissue, may monitor arterial blood pressure. Transcranial Doppler may provide signals that are transformable into pressure-related signals indicative of intracranial pressure. Pressure-related signals indicative of intracranial pressure may as well be measured by means of a sensor device measuring air pressure within the outer ear channel after air-tight sealing of the outer ear by some kind of closing material to exclude interference from the atmospheric air pressure. The problem with so-called non-invasive pressure monitoring is that absolute pressure within the body or body cavity is unknown. The absolute pressure usually refers to the pressure difference between the pressures within the body or body cavity and the atmospheric pressure. Another major problem is that it can be impossible to know whether the pressure measurements are good or bad, i.e. whether the quality of the measurements or pressure signals are good or bad. This problem is at least partly related to the lack of a standard of what might be considered a good (or bad) pressure measurement.

Since the 1950's fluid flow valves have been used to drain excess fluid from a human brain or spinal fluid body cavity. Such fluid flow valves may be controllable, i.e. the degree of fluid drainage is adjustable. Such devices include some kind of mechanically adjustable valves. Pressure monitoring has received no or minimal role as related to said drainage of fluid from a brain or spinal fluid body cavity. A major cause is that pressure monitoring according to prior art technology measures absolute pressure, i.e. relative to atmospheric pressure. Changes in atmospheric pressure would change the zero pressure level and thus the measured pressure values. Sensor-related drift of zero pressure level also heavily affects the pressure measurements that are relative to atmospheric pressure.

SUMMARY OF THE INVENTION

This invention provides technical solutions concerning at least ten features related to pressure monitoring, as further defined in the preamble of attached ten independent claim 1. For the sake of clarity, in this document it is referred to ten features of the invention. This should, however, not be considered as a limitation of the scope of the invention. Although the description and the drawings relate to all of the features of the invention, the claimed part of the invention according to the attached claims is related to the third feature of the invention.

Current and existing technology gives no or minimal opportunities for quality control whether a pressure signal incorporates pressure waves related to the cardiac beats or pressure waves related to artifacts or a combination of cardiac beat-induced and artifact-induced pressure waves. It is well known from prior art that each cardiac beat causes a pressure wave that is transferred from the intra-cardiac and intra-arterial compartments to the other human or animal body cavities. The shape and magnitude of the individual pressure waves depend on the particular body cavity, compartment of body cavity, the way of measuring the pressure wave, the absolute pressure level, and other factors such as posture and medications. Depending on how a pressure signal is measured, the pressure signal may contain noise of various types and pressure waves not related to cardiac beats. The challenge is to identify the single pressure waves corresponding to the cardiac beats, i.e. not to misinterpret an artifact-induced pressure wave as a cardiac beat-induced pressure wave. Said challenge is even greater when a pressure-related signal is derived from a non-invasive source containing much noise in the signal.

The first feature of this invention provides for a method for best possible differentiating between cardiac beat-induced pressure waves and pressure waves related to artifacts or a combination thereof. More specifically said first feature of the invention relates to: A method for processing continuous pressure-related signals derivable from locations inside or outside a human or animal body or body cavity, comprising the steps of obtaining samples of said signals at specific intervals, and converting thus sampled pressure signals into pressure-related digital data with a time reference, wherein for selectable time sequence windows the method comprising the further steps of:

a) identifying from said digital data single pressure waves related to cardiac beat-induced pressure waves,
b) identifying from said digital data pressure waves related to artifacts or a combination of artifacts and cardiac beat-induced pressure waves,
c) computing single pressure wave (SW.x)-related parameters during individual of said time sequence windows,
d) computing delta single pressure wave ($\Delta$SW.x)-related parameters between subsequent single pressure waves (n−1;n) within said time sequence windows,
   said subsequent single pressure waves (n−1;n) representing a current single pressure wave SW[n].x in time n subtracted from the previous SW[n−1].x in time n−1 of said individual time sequence window,
e) computing time sequence (TS.x)-related parameters of said single pressure waves during individual of said time sequence windows,
f) computing delta time sequence ($\Delta$TS.x)-related parameters between subsequent time sequence windows (n−1;n) of said individual time sequence windows,
   said subsequent time sequence windows (n−1;n) representing a current time sequence window TS[n].x in time n subtracted from the previous TS[n−1].x in time n−1 of said individual time sequence window,
g) determining criteria for thresholds and ranges of said single pressure wave (SW.x)-related parameters of said single pressure waves during said time sequence windows,
h) determining criteria for thresholds and ranges of said delta single pressure wave ($\Delta$SW.x)-related parameters between subsequent of said single pressure waves during said time sequence windows,
i) determining criteria for thresholds and ranges of said time sequence (TS.x)-related parameters of said single pressure waves during said time sequence windows,
j) determining criteria for thresholds and ranges of said delta time sequence ($\Delta$TS.x)-related parameters between subsequent time sequence windows, and
k) using said criteria for thresholds and ranges in steps g)-j) to provide optimal differentiating between single pressure waves caused by cardiac beat-induced pressure waves and pressure waves caused by artifact-induced pressure waves or a combination thereof.

Further embodiments of this first feature of the invention are derivable from the descriptive portion of the specification and the related drawings.

This first feature of the invention should be considered an iterative process aiming at establishing a process method for optimal identification of pressure waves created by cardiac beat-induced pressure waves. Said criteria can be determined for specific signals in several recordings (each recording containing one or more signals). After determining said criteria in a selectable number of signals, these new criteria are determined and implemented in the inventive method. Both manual and automatic verification may be used to evaluate whether the improved method identifies pressure waves created by cardiac beat-induced pressure waves, not pressure waves created by artifacts or a combination thereof. Different criteria are determined for different types of signals, different locations of signals, and different sensors wherefrom signals are derived.

The significance of determining criteria related to thresholds and ranges of said single wave (SW.x)-, delta single wave ($\Delta$SW.x)-, time sequence (TS.x)- and delta time sequence ($\Delta$TS.x)-related parameters is that a precise tool is created for excluding pressure waves not related to cardiac beat-induced pressure waves. It has been shown that for specific types of signals and locations, said criteria are quite narrow for single pressure waves related to cardiac beat-induced pressure waves. This fact makes it easy to identify artifact-induced pressure waves, and it is very useful when comparing identical pressures derivable from different locations. Thus, a very precise tool for identification of pressure waves related to cardiac beat-induced pressure waves is established, which is crucial for other features of this invention. Such differentiation between single pressure waves created by cardiac beat-induced pressure waves, pressure waves caused by artifacts, or a combination of cardiac beat and artifact-induced pressure waves is not possible by currently used, prior art technology.

Current and prior art technology of processing pressure signals gives limited and less useful information about the pressures that are measured. An example is given. The major reason for continuous intracranial pressure (ICP) monitoring is to obtain information about cerebral elastance and compliance. Elastance (E) is a function of the relationship between pressure change and volume change (E=$\Delta$P/$\Delta$V). Increased cerebral elastance (E) implies that a small intracranial volume increase ($\Delta$V) causes a large intracranial pressure increase ($\Delta$P). Compliance (C) is the inverse of elastance (C=1/E). These relationships have been described in the pressure-volume curve of Langfit, which is well known from the prior art. Current, prior art technology of processing continuous intracranial pressure (ICP) signals gives no or minimal information about compliance. Instead rather complex pressure-volume relationships must be computed based on introduced volume changes during continuous intracranial pressure (ICP) monitoring. Another major challenge with current technology is that pressure measurements are very sensitive to calibration against a zero pressure level. Pressure signals derived from inside a human or animal body or body cavity usually are absolute pressure values, which are relative to atmospheric pressure level. Problems related to calibration against said atmospheric pressure level or related to drift of a zero pressure level during a measurement may give misleading pressure measurements.

In a second feature of this invention a method for processing continuous pressure-related signals is described that extracts new information about pressures from the pressure signal itself. More specifically said second feature of the invention relates to: A method for processing continuous pressure-related signals derivable from locations inside or outside a human or animal body or body cavity, comprising the steps of obtaining samples of said signals at specific intervals, and converting thus sampled pressure signals into pressure-related digital data with a time reference, wherein for selectable time sequence windows the method comprising the further steps of:

a) identifying from said digital data single pressure waves related to cardiac beat-induced pressure waves,
b) identifying from said digital data pressure waves related to artifacts or a combination of artifacts and cardiac beat-induced pressure waves,
c) computing time sequence (TS.x)-related parameters of said single pressure waves during individual of said time sequence windows, and
d) establishing an analysis output selected from one or more of said time sequence (TS.x)-related parameters of said single pressure waves during individual of said time sequence windows:
  d1) mean wave amplitude (TS.MeanWavedP),
  d2) mean wave latency (TS.MeanWavedT),
  d3) mean wave rise time coefficient (TS.MeanWaveRT),
  d4) mean amplitude (TS.MeandP),
  d5) mean latency (TS.MeandT),
  d6) mean rise time coefficient (TS.MeanRT), and
  d7) mean single wave pressure (TS.Mean$_{SW}$P).

Further embodiments of this second feature of the invention are derivable from the descriptive portion of the specification and the related drawings.

The analysis output of said method may be presented in a variety of ways such as numerical values; trend plots of numerical values, histogram presentations or as a quantitative matrix. Thereby completely new information about pressures is obtained.

The significance of said analysis output is great. For example, computation of TS.MeanWavedP or TS.MeandP makes it possible to demonstrate reduced intracranial compliance, not revealed by current, prior art technology. Thus, information about cerebral compliance is derived from the intracranial pressure (ICP) signal itself. The determined values of these parameters are highly predictable of response to extra-cranial shunt treatment and selection of shunt valve opening. Determination of these parameters (e.g. TS.Mean$_{SW}$P) has made it possible to determine whether a pressure signal is of good quality or of bad quality. For example, in test measurements of several patients (both children and adults) it was found that intracranial pressure (ICP) values indicated normal pressures, despite subcutaneous (below skin) placement of a solid pressure sensor (Codman ICP Microsensor, Johnson & Johnson, Raynham, Mass.). Mean ICP was computed according to existing and prior art technology, as sum of pressure levels divided by number of samples independent whether pressure waves were related to cardiac beats or artifacts. In these cases current and prior art technology computed wrong and misleading pressure measurements. Determination of TS.Mean$_{SW}$P (or other of said TS.x-related parameters) according to this invention, revealed the bad signal quality since no single pressure waves were identified, and hence no time sequence (TS.x) parameters were computed. Furthermore, problems related to zero calibration against atmospheric pressure are eliminated by said second feature of this invention. This is related to the fact that TS parameters such as d1)-d7) all are relative values, not influenced by said atmospheric pressure level.

Current and existing technology includes a number of approaches and methods for non-invasive pressure monitoring, i.e. measuring pressures inside a body or body cavity without introducing the sensor inside said body or body cavity. For example, different variations of applanation technology may be used for measuring arterial blood pressure, ocular pressure (and intracranial pressure in infants). Pressure-related signals indicative of intracranial pressure (ICP) may be derived from transcranial Doppler signals, cranial impedance-related signals or pressure-related signals from within the outer ear channel after airtight sealing of the outer ear channel. However, a problem with said methods of non-invasive pressure monitoring is that only relative changes in pressure over time may be measured, related to the fact that the absolute pressures within the body cavity remain unknown during non-invasive pressure measurements. Another problem relates to the fact that current and existing technology of non-invasive pressure monitoring provides for no or minimal quality control whether the measured signals are good or bad. This is at least partly related to lack of a reference material of what is considered as good signals and bad signals.

A third feature of this invention provides for a method of comparing signals derived simultaneously from different locations. Thereby relationships between such simultaneous signals may be determined. A reference material can be built up for relationships between specific signals (and attributes such as location and sensor type). These established relationships may subsequently be used for formula-based adjustments of individual signals solely obtained by a non-invasive approach, thus modifying the individual continuous non-invasive pressure-related signals into signals highly predictable of the corresponding invasive pressure-related signals. More specifically a first aspect of said third feature of the invention relates to: A method for processing two or more simultaneous continuous pressure-related signals derivable from a human or animal body from one or more locations thereof electable from: inside the body, outside the body, inside body cavity, outside body cavity, comprising the steps of obtaining samples of said signals at specific intervals, and converting thus sampled pressure signals into pressure-related digital data with identical time reference, wherein for selectable and simultaneous time sequence windows the method comprising the further steps of:

a) identifying from said digital data single pressure waves related to cardiac beat-induced pressure waves within said two or more simultaneous signals constituting a pressure recording,
b) identifying from said digital data pressure waves related to artifacts or a combination of artifacts and cardiac beat-induced pressure waves within said two or more simultaneous signals constituting a pressure recording,
c) computing time sequence (TS.x)-related parameters of said single pressure waves during said identical time sequence windows within said two or more simultaneous signals constituting a pressure recording, wherein the method comprising the further steps of:
d) determining relationships between time sequence (TS.x)-related parameters of said identical time sequence windows within said two or more simultaneous signals constituting a pressure recording,
   said relationships calculated as related time sequence (rTS.x) parameters, and
e) determining said related time sequence (rTS.x) parameters for individual recordings,
f) determining said related time sequence (rTS.x) parameters for a population of recordings, and
g) using said related time sequence (rTS.x) parameters for formula-based adjustment of time sequence windows of individual pressure-related signals,
h) creating from said formula-based adjustments factorized time sequence (fTS.x) parameters of said individual time sequence windows of said individual continuous pressure-related signal.

Further embodiments of this third feature of the invention are derivable from the descriptive portion of the specification and the related drawings.

Preferably said related time sequence (rTS.x) parameters should be obtained for a population of recordings in order to determine different formula-based relationships for specific types of signals and locations and sensor types. This procedure subsequently creates a reference material that may be applied on new and individual non-invasive pressure measurements. Thereby continuous pressure-related signals from a non-invasive source may be processed in a way that makes the continuous non-invasive pressure signals highly predictable of the pressures inside the body or body cavity. How said established relationships may be used for formula-based adjustments of individual signals such as solely obtained by a non-invasive approach, thus modifying the individual continuous non-invasive pressure-related signals into signals highly predictable of the corresponding invasive pressure-related signals is more specifically described in a second aspect of said third feature of the invention and with further embodiments thereof defined in related sub-claims 2-25. These features are also derivable from the descriptive portion of the specification and the related drawings. Thus, this second aspect of the third feature of the invention is defined, according to attached claim 1 by:

A method for processing continuous pressure-related signals derivable from locations inside or outside a human or animal body or body cavity, comprising the steps of obtaining samples of said signals at specific intervals, and converting thus sampled pressure signals into pressure-related digital data with a time reference, wherein for selectable time sequence windows the method comprises the further steps of:
a) identifying from said digital data single pressure waves related to cardiac beat-induced pressure waves,
b) identifying from said digital data pressure waves related to artifacts or a combination of artifacts and cardiac beat-induced pressure waves,
c) computing time sequence (TS.x)-related parameters of said single pressure waves during individual of said time sequence windows,
d) adjusting said time sequence (TS.x)-related parameters of said single pressure waves during individual of said time sequence windows using formula-based adjustments based on related time sequence (rTS.x) parameters,
e) creating from said formula-based adjustments factorized time sequence (fTS.x) parameters of said individual time sequence windows of said continuous pressure-related signals, and
f) establishing an analysis output selected from one or more of said factorized time sequence (fTS.x)-related parameters of said single pressure waves during individual of said time sequence windows.

It has been found that the significance of said third feature of the invention is great, as related to comparisons of identical pressures from different locations. By using the method described according to the third feature of the invention, continuous pressure signals derived from an epidural location became highly predictable of continuous pressure signals derived from within the brain parenchyma, i.e. intra-dural. Thereby, the invention enables epidural intracranial pressure (ICP) to be as precise as intra-dural pressure measurements from inside the brain parenchyma. This is a major advantage as epidural pressure measurements are less invasive, not requiring penetration of a cannula or sensor into the brain parenchyma. Furthermore, continuous pressure-related signals derived from the outer ear channel became highly predictable of continuous pressure signals derived from within the brain parenchyma itself. Thus, this third feature of the invention gives a technical solution to a major problem of non-invasive pressure recording, namely that absolute pressure relative to atmospheric pressure inside the body or body cavity is unknown during non-invasive pressure recording.

A technical problem related to measuring air pressure within the outer ear channel is to obtain airtight sealing of the outer ear channel. This may be practically difficult as the ear channel is very different from individual to individual.

According to a fourth feature of this invention, a technical solution is given to the problem of airtight sealing of an outer ear channel. A device for closing of said outer ear channel is described. More specifically said fourth feature of the invention relates to: A device for use in sensing continuous pressure-related signals through non-invasive pressure measurements on a human or animal body, comprising
   a pressure sensor with a pressure sensing tube, said tube insertable into a human or animal outer ear channel spaced from a tympanic membrane thereof,
   wherein inflatable means surrounds an outside length of the tube, said inflatable means upon inflation thereof sealingly closing an annular gap between a region of said tube and a wall region of said outer ear channel.

The significance of this device is that said inflatable means is thin-walled and soft, thus making airtight sealing of an outer ear channel possible, independent on the diameter of the outer ear channel. Thereby one size of said sensor may be used independent of the diameter of the outer ear channel.

Further embodiments of this fourth feature of the invention are derivable from the descriptive portion of the specification and the related drawings.

Drainage of fluid from a human brain or spinal fluid cavity can be required in the case of excess fluid within one of said cavities. Fluid flow valves developed for this kind of fluid drainage was introduced to the marked in the 1950's, and later on valves with adjustable fluid flow rate were introduced. Even after about half a century with using such valves for drainage of cerebrospinal fluid (CSF), there are still unsolved technical problems related to such valves: Over-drainage of cerebrospinal fluid (CSF) represents a great and unsolved problem with all kinds of shunts. No shunts allow for adjustment of shunt valve opening and fluid flow rate based on pressure measurements with determination of cerebral compliance.

According to a fifth feature of this invention, technical problems related to current and prior art technology of draining excess fluid are solved. More specifically said fifth feature of the invention relates to: A device for use in draining excess fluid from a brain or spinal fluid cavity unto another body cavity of a human being, comprising:
- a first drainage tube having an inlet thereof located in said brain or spinal fluid cavity, said first drainage tube connected to the inlet of a fluid flow controllable valve,
- a valve-opening regulator with associated control unit being connected to a regulator and processing unit, the control output from which is a function of pressure-sensing signals derived from at least one pressure sensor, a pressure transducer transforming said pressure-sensing signals into signals processed by said processing unit, a power supply, information transferable means, and
- a second drainage tube from an outlet of said valve opening having a distal outlet thereof, said distal outlet opening into said another human body cavity, wherein said first drainage tube, said fluid flow controllable valve, said valve-opening regulator, said control unit, said regulator, said processing unit, said pressure transducer, said power supply, said information transferable means and said second drainage tube being located below a skin surface of said human body.

Further embodiments of this fifth feature of the invention are derivable from the descriptive portion of the specification and the related drawings.

The significance of the new inventive feature of this device relates to incorporation of said processing unit, which enables accurate control of valve opening and fluid flow rate. Said control is based on output of analyzing pressure-related signal from cavity wherein fluid is drained. Shunt valve opening and fluid flow rate may be regulated in a physiological way, i.e. the fluid flow rate is regulated according to intracranial compliance. Drainage of fluid is regulated to obtain optimal cerebral compliance. This inventive aspect represents a technical solution to the problem of over-drainage. In addition, in the case of suspected shunt failure, information about cerebral compliance can be obtained using said information transferable means.

According to a sixth feature of this invention a method is described for processing continuous pressure-related signals, said method being incorporated in said processing unit of said device for use in draining excess fluid from a brain or spinal fluid cavity. More specifically said sixth feature of the invention relates to: A method for processing continuous pressure-related signals derivable from locations inside or outside a human body or body cavity, comprising the steps of obtaining samples of said signals at specific intervals, and converting thus sampled pressure signals into pressure-related digital data with a time reference, wherein for selectable time sequence windows the method comprises the further steps of:
a) identifying from said digital data single pressure waves related to cardiac beat-induced pressure waves,
b) identifying from said digital data pressure waves related to artifacts or a combination of artifacts and cardiac beat-induced pressure waves,
c) computing time sequence (TS.x)-related parameters of said single pressure waves during individual of said time sequence windows,
d) establishing an analysis output of said time sequence (TS.x)-related parameters for a selectable number of said time sequence windows,
e) establishing a deliverable first control signal related to an analysis output in step d) for a selectable number of said time sequence windows, said first control signal being determined according to one or more selectable criteria for said analysis output, and
f) modifying said deliverable first control signal into a second control signal to provide a performance modifying signal.

Further embodiments of this sixth feature of the invention are derivable from the descriptive portion of the specification and the related drawings.

The significance of this method is related to the fact that physiological regulation of shunt valve opening and valve fluid flow rate is found. It has been found that an analysis output related to TS.MeanWavedP (or other parameters such as e.g. TS.MeanWavedT, TS.MeandP, and TS.MeandT) was very useful for adjustment of shunt valve opening. The inventive method enables regulation of a shunt valve in a way that is not available by current, prior art technology. Furthermore, in case of suspected shunt dysfunction, computation of said TS.x parameters provides new information whether suspected shunt malfunction includes over- or under-drainage.

The identifying and computing steps of said process method related to the sixth feature of the invention are comparable to the identifying and computing steps of the process method related to the second feature of the invention.

Said methods of said first, second, third, and sixth features of this invention relate to methods for processing continuous pressure-related signals independent on locations of said continuous pressure-related signals. Examples of human or animal body cavities include: intracranial cavity (independent of whether intra- or extra-ventricular, intra-dural or epidural, spinal or cranial), ocular cavity, inner or outer ear cavities, intra-arterial cavity (independent of whether intra-arterial or intra-cardiac), intra-venous cavities (independent of wherein the various venous cavities), gastro-intestinal body cavities (independent of the specific type of gastrointestinal cavity such as esophageal pressure, duodenal pressure, intraperitoneal pressure), and urinary tract pressure (independent of which part of the urinary tract cavity). Said methods for processing continuous pressure-related signals are as well independent on type of pressure sensor, thus independent on whether said sensors are placed inside or outside a human or animal body or body cavity.

According to a seventh feature of this invention a system is described for processing continuous pressure-related signals, said system being used for controlling drainage of excess fluid from a first body cavity to a second body cavity of a human being. More specifically said seventh feature of the invention relates to: A system for processing continuous pressure-related signals derivable from one or more sensor(s) having location(s) inside or outside a body or body cavity of a human being, said system comprising:
a) means for on basis of said signals receivable from said sensor(s) via pressure transducer means to control drainage fluid flow rate from a first body cavity to a second body cavity in one said human,
b) a processing device in said system having means for processing said signals, said processing means including sampling means for sampling said signals at specific intervals,
c) converter means for converting the sampled signals into pressure related digital data with a time reference,
d) means for during selectable time sequence windows identifying from said digital data single pressure waves related to cardiac beat-induced pressure waves, and related to artifacts or a combination of cardiac beat-induced waves and artifacts,
e) means for computing and analyzing said digital data during said selectable time sequence windows,
f) means for outputting to device terminal means one or more pressure parameter signals related to a selectable number of said time sequence windows:

f1) mean wave amplitude (TS.MeanWavedP),
f2) mean wave latency (TS.MeanWavedT),
f3) mean wave rise time coefficient (TS.MeanWaveRT),
f4) mean amplitude (TS.MeandP),
f5) mean latency (TS.MeandT),
f6) mean rise time coefficient (TS.MeanRT),
f7) mean single wave pressure (TS.Mean$_{SW}$P), and g) a valve device controlling the drainage fluid flow rate and connectable to said body cavities, h) regulator unit means connectable to said terminal means for receiving at least one of said parameter signals, said regulator unit means being capable of establishing a device performance modifying signal by means of one of said pressure parameter signals or a combination effect obtained from using at least two of said pressure parameter signals, wherein said performance modifying signal deliverable from said regulator unit being capable of controlling said drainage fluid flow rate through said valve device by input to a valve-opening regulator.

Further embodiments of this seventh feature of the invention are derivable from the descriptive portion of the specification and the related drawings.

There are several major advantages with this seventh feature of the invention, as compare to current, prior art technology. The system enables assessment of cerebral compliance that may be used to control drainage of excess fluid, thereby ensuring optimal cerebral compliance. Furthermore, the system provides for quality control of the continuous pressure-related signals, thus reducing the risk of computing false or misleading pressure parameters.

According to an eight feature of this invention a device is described for use in sensing continuous pressure-related signals. Said device can be used to display new information from pressure measurements derived from the inventive method of processing continuous pressure-related signals. More specifically said eight feature of the invention relates to: A device for use in sensing continuous pressure-related signals derivable from locations inside or outside a human or animal body or body cavity, comprising a pressure sensor with a pressure sensing element,
    a pressure transducer capable of transforming said pressure-related signals into digital pressure-related signals,
    a processing unit with input means for receiving said pressure-related digital signals, said processing unit providing at output means thereof one or more of the following time sequence parameters during selectable time sequence windows of said pressure-related signals:
    mean wave amplitude (TS.MeanWavedP),
    mean wave latency (TS.MeanWavedT),
    mean wave rise time coefficient (TS.MeanWaveRT),
    mean amplitude (TS.MeandP),
    mean latency (TS.MeandT),
    mean rise time coefficient (TS.MeanRT),
    mean single wave pressure (TS.Mean$_{SW}$P),
    a display unit connected to said output means for selectively displaying said one or more parameters, and
    means for supplying power to power consuming parts of the device.

Further embodiments of this eight feature of the invention are derivable from the descriptive portion of the specification and the related drawings.

The significance of this eight feature of the invention is important as compared to existent and prior art technology. The inventive method of processing continuous pressure-related signals providing for completely new information about pressures can be incorporated in this device. Various modifications of the device are within the scope of the invention. Thereby new information about pressures can be obtained in various settings such as within the home of a patient or within the hospital. Said new information can be derived from the continuous pressure signal itself and be displayed, enabling quick diagnosis and intervention.

According to the ninth feature of this invention a device is described for use in sensing continuous pressure-related signals derivable from locations inside or outside a human or animal body or body cavity. This device is a sensor device or a combined sensor-display device. The inventive method of processing continuous pressure-related signals is a part of said device. More specifically said ninth feature of the invention relates to: A device for use in sensing continuous pressure-related signals derivable from locations inside or outside a human or animal body or body cavity, comprising a pressure sensor with a pressure sensing element,
    a pressure transducer capable of transforming said pressure-related signals into digital pressure-related signals,
    a processing unit with input means for receiving said pressure-related digital signals, said processing unit providing at output means thereof one or more of the following time sequence parameters during selectable time sequence windows of said pressure-related signals:
    mean wave amplitude (TS.MeanWavedP),
    mean wave latency (TS.MeanWavedT),
    mean wave rise time coefficient (TS.MeanWaveRT),
    mean amplitude (TS.MeandP),
    mean latency (TS.MeandT),
    mean rise time coefficient (TS.MeanRT),
    mean single wave pressure (TS.Mean$_{SW}$P),
    information transfer means connected to said output means and enabling transferal of information to an external unit of at least said one or more parameters, and
    means for supplying power to power consuming parts within the device.

Further embodiments of this ninth feature of the invention are derivable from the descriptive portion of the specification and the related drawings.

There are several major advantages with said ninth feature of the invention. By means of the sensor device itself completely new information from pressure measurements can be derived from a sensor device itself. Modifications of said sensor device are within the scope of the invention. One possible modification of said sensor device can be implanted within the patient. For example, said sensor device can be implanted within a human or animal body or body cavity, enabling pressure measurements at any time, using information transfer means of said sensor device. As compared to current and prior art technology, this sensor device provides completely new information about pressures. This new information is not dependent on a zero pressure level against atmospheric pressure, which is crucial for implantable modifications of said sensor device.

The tenth feature of this invention relates to a system for processing continuous pressure-related signals derivable from one or more sensor(s) having location(s) inside or outside a body or body cavity of a human being or animal. This system can be incorporated in various devices. The system incorporates the inventive method of processing continuous pressure-related signals. More specifically said tenth feature of the invention relates to: A system for processing continuous pressure-related signals derivable from one or more sensor(s) having location(s) inside or outside a body or body cavity of a human being or animal, said system comprising:

means for on basis of said signals receivable from said sensor(s) via pressure transducer means to display output of said processing, and a processing unit in said system having means for processing said signals, said processing means including:
a) sampling means for sampling said signals receivable from said pressure transducer means at specific intervals,
b) converter means for converting the sampled signals received from said sampling means into pressure related digital data with a time reference,
c) identifying means for during selectable time sequence windows identifying from said digital data output from said converter means single pressure waves related to cardiac beat-induced pressure waves, related to artifacts, or a combination of cardiac beat-induced waves and artifacts,
d) computing means for computing time sequence parameters from included or selected time sequence windows output from said identifying means,
e) analyzing means for analyzing said time sequence parameters in the form of digital data related to said selectable time sequence windows,
f) output means for outputting to device terminal means one or more pressure parameters related to a selectable number of said time sequence windows:
   f1) mean wave amplitude (TS.MeanWavedP),
   f2) mean wave latency (TS.MeanWavedT),
   f3) mean wave rise time coefficient (TS.MeanWaveRT),
   f4) mean amplitude (TS.MeandP),
   f5) mean latency (TS.MeandT),
   f6) mean rise time coefficient (TS.MeanRT),
   f7) mean single wave pressure (TS.Mean$_{SW}$P),
and
g) means for supplying power to power consuming parts within the system.

Further embodiments of this tenth feature of the invention are derivable from the descriptive portion of the specification and the related drawings.

The important aspect of this tenth feature of the invention is that the inventive method can be incorporated within said system. Said system can further be incorporated in many devices, providing for new diagnostic information, not available by current and prior art technology.

The invention is now to be further described with reference to advantageous, exemplifying embodiments and alternatives thereof, as also supported by the attached drawings.

BRIEF DESCRIPTION OF THE DRAWINGS

FIG. 2 shows a flowchart over a method for processing continuous pressure-related signals including determination of criteria for thresholds and ranges of single wave (SW.x)-, delta single wave (ΔSW.x)-, time sequence (TS.x)- and delta time sequence (ΔTS.x)-related parameters.

FIG. 3a shows two subsequent individual time sequence windows including all identified peaks and valleys related to both cardiac beat-induced single pressure waves and artifact-induced pressure waves or a combination thereof, FIG. 3b shows pressure waves with all detected peaks and valleys, and FIG. 3c shows single pressure waves with included pair combinations of peaks and valleys.

FIG. 12a shows a schematic presentation of a device connecting a first and a second body cavity including a valve for draining excess fluid from a first body cavity, and FIG. 12b shows a putative relationship between valve opening and fluid flow rate of a fluid flow rate controllable valve.

FIG. 13a shows changes in absolute mean intracranial pressure (TS.MeanP) during three measurement periods including three adjustments of a fluid flow rate controllable valve, FIG. 13b shows changes in mean intracranial pressure wave amplitude (TS.MeanWavedP) during three measurement periods including three adjustments of a fluid flow rate controllable valve, and FIG. 13c shows changes in mean intracranial pressure wave latency (TS.MeanWavedT) during three measurement periods including three adjustments of a fluid flow rate controllable valve.

FIG. 15a is a schematic presentation of a sensor and display device with a sensor incorporated within the device, FIG. 15b is a schematic presentation of a display device with a pressure sensor connectable to the device, FIG. 15c is a schematic presentation of a sensor and display device including information transfer means, parameter selection control means, parameter data storage means and with a sensor incorporated within the device, and FIG. 15d is a schematic presentation of a display device including information transfer means, parameter selection control means, parameter data storage means, however, with a pressure sensor connectable to the device.

FIG. 16a is a schematic presentation of a sensor device with a pressure sensor incorporated within the device, FIG.

16b is a schematic presentation of a sensor related device with a sensor connectable to the device, FIG. 16c is a schematic presentation of a sensor device including a display and with a sensor incorporated within the device, and FIG. 16d is a schematic presentation of a device including a display, however, with a pressure sensor connectable to the device.

DETAILED DESCRIPTION OF PREFERRED EMBODIMENTS

Figure 1:
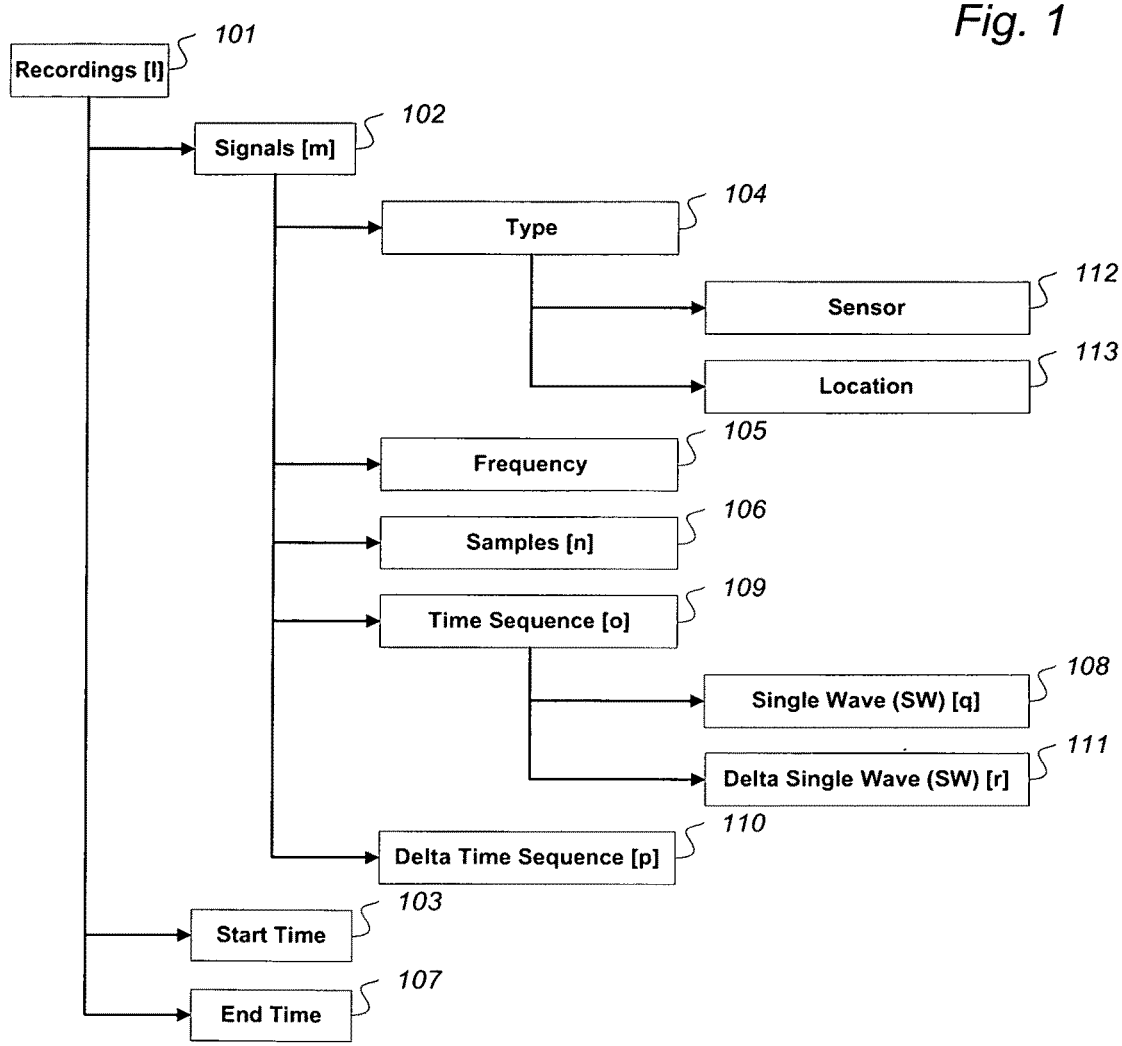
FIG. 1 shows an overview of notations related to important terms of this invention.

In FIG. 1 is shown an overview of notation and relationships related to continuous pressure signals, as used according to this invention. A recording 101 is one or more simultaneous signals 102 derivable from locations inside or outside a human or animal body or body cavity, each of said signals 102 having identical time reference, though it is not a requirement that start time 103 is identical for all signals of a recording. Each signal has the following attributes: type 104, frequency 105, and actual samples 106. Given these values, end time 107 can be calculated. According to this invention a specific sampling frequency 105, is not given. For single pressure wave analysis, it has been found that sampling frequencies of 100 to 200 Hz are useful. The notation List[x] is a reference to an element within an ordered list. With reference to FIG. 1, some examples are given:

The notation Recording [1].Signal [m].Time Sequence [o].Single Wave [q]) denotes a specific Single Wave [q] 108 within a specific Time Sequence [o] 109 within a specific Signal [n] 102, within a specific Recording [1] 101.

The notation Recording [1].Signal [m].Samples [n] denotes a specific Sample [n] 106 within a specific Signal [m] 102 within a specific Recording [1] 101.

Signal.Samples[n] denotes a specific sample within a non-specific signal, a general notation for a signal without specifying a dedicated signal.

The notation Recording [1].Signal [m].Delta Time Sequence [p] denotes a specific Delta Time Sequence [p] 110 within a specific Signal [m] 102 within a specific Recording [1] 101. The notation Recording [1].Signal [m].Time Sequence [o].Delta Single Wave [r] denotes a specific Delta Single Wave [r] 111 within a specific Time Sequence [o] 109 within a specific Signal [m] 102 within a specific Recording [1] 101.

The ordering is always starting with one, e.g. the first available time sequence window within the first available signal within a recording is denoted by Signal[1].Time Sequence[1].

Abbreviations may be used for Single Wave [m] (=SW [m]), Delta Single Wave [r] (=ΔSW[r]), Time Sequence [o] (=TS[o]) and Delta Time Sequence [p] (=ΔTS [p]).

It is important to note that attributes to type 104 are sensor 112 and location 113. Both these attributes are required to give a precise description of pressure signal type 104.

The notation Recording [1].Signal [m].Type.Location denotes a specific Location 113 within a specific Type 104 within a specific Signal [n] 102, within a specific Recording [1] 101. The notation Recording [1].Signal [m].Type.Sensor denotes a specific Sensor 112 within a specific Type 104 within a specific Signal [n] 102, within a specific Recording [1] 101. The present invention relates to a method of all types of human or animal continuous pressure-related signals 102.

The inventive method for processing continuous pressure-related signals 102 is independent on said locations 113, said locations being starting points (or origins) of said continuous pressure-related signals 102. Examples of said locations described in this document are given: Epidural refers to a location outside the dura mater of the brain but within the cranial vault. Intracranial/intra-dural refers to inside the dura mater of the brain. Spinal intra-dural refers to inside the dura mater of the spinal cord. Intra-arterial refers to a location inside an arterial blood vessel.

Said method for processing continuous pressure-related signals 102 is independent on type of pressure sensor 112, said sensor 112 being placed inside or outside a human or animal body or body cavity. There are many types of pressure sensors. A pressure sensor 112 can be a pressure measuring unit or pressure sensing element connected to a pressure conveying probe, e.g. a probe in the form of a fluid catheter and/or cannula. It should be understood that if a pressure sensor 112 is associated with a fluid cavity, e.g. in the brain, the pressure sensor 112 would conveniently be a element communicating with the cavity via the probe, unless the unit is so small in size that it can be safely located within the fluid cavity, e.g. at the proximal tip of a probe or catheter. A pressure sensor 112 can also be placed directly within the body or body cavity. Three examples of pressure sensors are listed: The Baxter (Truwave PX-600F vein/arterial anesthesia pressure monitoring kit) Health Care Corporation type of sensor measures fluid pressure within a catheter introduced via a cannula into a body cavity (e.g. cerebrospinal fluid body cavity, arterial blood cavity or venous blood cavity). Codman ICP MicroSensor™ (Johnson & Johnson, Raynham, Mass., USA) is a solid sensor which can be introduced into the brain parenchyma for intracranial pressure (ICP) monitoring. Spiegelberg ICP Probe 3XL (Spiegelberg, Aesculap, Germany) is a catheter which can be introduced into a brain cerebrospinal fluid (CSF) cavity wherein the pressure sensing element is outside the patient, thus measuring pressure within said Probe 3XL. These sensors are listed to exemplify that measurement of one pressure type (i.e. intracranial pressure) involves different sensor types, and different locations of the sensor elements (i.e. outside or inside the intra-dural space).

A pressure signal 102 refers to a number of sequential and variable pressure samples 106 during a time period. A signal 102 containing a continuous sequential number of samples 106 may be derived from a human or animal body from one or more locations thereof electable from: inside the body, outside the body, inside body cavity, outside body cavity.

As indicated in FIG. 1, a signal 102 is equivalent to: Recording [1].Signal [m].Samples [n].

A sample 106 is defined as: Pressure value at a specific time. Each of said samples contains a pressure value at a specific time. A selectable time sequence window is a selected time frame of said signal 102. Each of said selectable time sequence windows is related to a number of time-related sequential pressure samples 106, each sample 106 referenced by a sample number, and elapsed time that is determined by sample 106 location number and sample frequency 105. A specific duration of said time sequence windows is not given. However, for test purposes there has been used time sequence windows of 6 seconds duration. Said selected time frame lies in the range 5-15 seconds, though this represents no limitation of the scope of the invention.

A major problem with current and prior art technology of processing continuous pressure-related signals is a lack of useful methods for verifying whether pressure signals are based on pressure waves created by the cardiac beats, not resulting from artifact waves or a combination of artifact waves and cardiac beat-induced pressure waves. The first feature of this invention is a method for best possible differentiation between pressure waves caused by either cardiac beat-induced pressure waves, artifact-induced pressure waves or a combination of artifact- and cardiac beat-induced pressure waves. This first inventive feature is of major significance since pressure measurements based on artifacts are misleading, giving wrong diagnostic information. The significance is even greater when continuous pressure-related signals are derived from outside as compared to inside a human or animal body or body cavity due to a larger proportion of artifacts.

Reference is now given to the first feature of the invention. Various aspects related to this first inventive feature are particularly illustrated in FIGS. 2, 3, 4, 5, 6, and 7.

First, reference is given to FIG. 2, providing an overview of the method for processing continuous pressure-related signals 201 derivable from locations inside or outside a human or animal body or body cavity, corresponding to said first feature of the invention. More details about the method are given together with detailed description of FIGS. 3, 4, 5, 6 and 7. The method for processing continuous pressure-related signals 201 derivable from locations inside or outside a human or animal body or body cavity, comprises the steps of sampling said signals at specific intervals, and converting thus sampled pressure signals into pressure-related digital data signal 201 with a time reference. For selectable time sequence windows, the method comprises the further steps of identifying from said digital data the single pressure waves related to cardiac beat-induced pressure waves, and the pressure waves related to artifacts or a combination of artifacts and cardiac beat-induced pressure waves. The process of differentiating between these different types of pressure waves is illustrated in FIG. 2. The process method incorporates different Identifying Steps, Computing Step and Determining Steps.

Said Identifying Steps include identification 202 of all separate peaks and valleys in said sampled signal 201. Each of said peaks is a sample with a pressure value and a time stamp or location, and each of said valleys is a sample with a pressure value and a time stamp or location. The result of applying General Methods Criteria 203 is either included, i.e. accepted, peak/valley pair combinations 204 or excluded, i.e. rejected, peak/valley pair combinations 205. After applying the Single Wave & Delta Single Wave Criteria 206 to said included peak/valley pairs 204, the output is either included, i.e. accepted, single pressure waves 207 or excluded, i.e. rejected, pressure waves 208. Said criteria 206 relate to thresholds and ranges of single pressure wave (SW.x)-related parameters and delta single pressure wave (ΔSW.x)-related parameters during time sequence windows. Included pair combinations 207 of peak/valley 204 pairs in said signal 201 correspond to accepted pair combinations of diastolic minimum pressure ($SW.P_{min1}$) and systolic maximum pressure ($SW.P_{max}$), which characterize single pressure waves created by cardiac beat-induced pressure waves. Said criteria 206 exclude minimum-maximum pressure ($SW.P_{min1}$/$SW.P_{max}$) pairs with said single pressure wave (SW.x)- and delta single pressure wave (ΔSW.x)-related parameters outside selectable thresholds and ranges. Pair combinations of diastolic minimum pressure ($SW.P_{min1}$) and systolic maximum pressure ($SW.P_{max}$) correspond to the diastolic minimum pressures and systolic maximum pressures of individual of pressure waves created by each of said cardiac beats. Time Sequence & Delta Time Sequence Criteria 209 are applied to each of said time sequence windows in a continuous series of said time sequence windows during a recording. Each time sequence window is a selected time frame of said signal. Said criteria 209 for thresholds and ranges of said time sequence (TS.x) and delta time sequence (ΔTS.x)-related parameters determine included, i.e. accepted, time sequence windows 210 and excluded, i.e. rejected, time sequence windows 211, that are used for further analysis. Said criteria 209 exclude time sequence windows 211 with said time sequence (TS.x)- and delta time sequence (ΔTS.x)-related parameters outside selectable thresholds and ranges.

At the Computing Step level, the following parameters are available: Single pressure wave (SW.x)-related parameters 212, delta single pressure wave (ΔSW.x)-related parameters 213, and time sequence (TS.x)-related parameters 214 for each individual of included time sequence windows 210. In addition, delta time sequence (ΔTS.x)-related parameters 215 are computed between subsequent time sequences (n−1; n) of said individual included time sequence windows 210. Said subsequent time sequence windows (n−1;n) represent a current time sequence window (TS[n].x) in time n subtracted from the previous TS[n−1].x in time n−1.

The Identifying Steps are applied to each of said time sequence windows in a continuous series of said time sequence windows during a recording.

The Computing Step is applied to each of said included time sequence windows 210 in a continuous series of said time sequence windows 210 during a recording.

In subsequent Determining Steps, criteria 216 are determined for thresholds and ranges of said SW.x-, ΔSW.x-, TS.x- and ΔTS.x-related parameters. One major application 217 of said criteria is to provide best possible differentiating between single pressure waves caused by cardiac beat-induced pressure waves and pressure waves caused by artifact-induced pressure waves or a combination thereof. By changing the set of criteria it is possible to change the proportion of excluded pressure waves and the proportion of excluded time sequence windows. There are several situations wherein the inventive step of determining criteria for optimal single pressure wave detection is crucial:

Determination of time sequence (TS.x)-related parameters derived from an invasive signal can be based on a minimal influence of artifact-induced pressure waves.

Determination of time sequence (TS.x)-related parameters derived from a non-invasive signal can be based on a minimal influence of artifact-induced pressure waves.

Determination of time sequence (TS.x)-related parameters derived from an invasive signal within a processing unit regulating a controllable shunt can be based on a minimal influence of artifact-induced pressure waves.

A more detailed description of General Methods Criteria (FIG. 2) is now given with reference to FIGS. 3a, 3b and 3c. The process described in this paragraph is intended to illustrate the concept, not to limit the scope of the invention. After the sampled pressure signal has been converted into a pressure-related digital data signal 301, all peaks 302 and valleys 303 in said sampled signal 301 are identified. Each of said peaks is a sample with a pressure value and a time stamp or location, and each of said valleys is a sample with a pressure value and a time stamp or location. Each individual peak 302 and valley 303 is identified with an absolute pressure value and a time stamp location.

First, it may be determined at which pressure levels the peaks 302 are located. The pressure level percentage lines 304 shown in FIG. 3a illustrate that 70.3% of all peaks within the 12 seconds recording period, have absolute pressure values between 20 and 35 mmHg, 22.2% of all peaks 302 have absolute pressure levels between 35 and 50 mmHg, and 7.5% of all peaks 302 have absolute pressure levels between 0 and 20 mmHg. Systolic maximum pressures ($SW.P_{max}$) 305, corresponding to cardiac beat-induced systolic maximum pressures probably should be at the absolute pressure level between 20 and 35 mmHg. A similar process is performed for all identified valleys 303 during this time period of 12 seconds. In the further analysis only those peaks 302 and valleys 303 with absolute pressure values within the majority pressure range are considered.

Another step is further illustrated in FIGS. 3b and 3c whereby nearby peaks 302 and valleys 303 are evaluated by using a so-called time window 306. A time window 306 refers to a selected time period, e.g. of 0.10 seconds duration. One of said General Methods Criteria (FIG. 2) defines that only the peak 302 with greatest absolute pressure value should be selected when several peaks 302 are identified within said time window 306.

Another of said General Methods Criteria (FIG. 2) define that only the valley 303 with the lowest absolute pressure value should be selected when several valleys 303 are identified within the same time window 306. In FIG. 3b is illustrated all the identified peaks 302 and valleys 303 within a short section of a continuous pressure-related signal 301. After application of the time window 306, it is shown in FIG. 3c that only peaks 302 with greatest absolute pressure values and valleys 303 with lowest absolute pressure values are remaining. In this example (FIG. 3c), the peak 302 corresponds to the systolic maximum pressures (SW.$P_{max}$) 305, and the valley 303 corresponds to the starting diastolic minimum pressure (SW.$P_{min1}$) 307. Thus, this process makes possible identification of included pair combinations of peaks 302 and valleys 303 in said signal 301. Other criteria determine that there cannot be two pair combinations of SW.$P_{max}$ 305 and SW.$P_{min1}$ 307 within one single wave duration (SW.WD), and that two different pair combinations of SW.$P_{max}$ 305 and SW.$P_{min1}$ 307 cannot contain either identical peaks 302 or valleys 303. It should be understood that various modifications, additions and improvements of said General Methods Criteria (FIG. 2) are within the scope of the invention.

The General Methods Criteria (FIG. 2) applied to continuous intracranial pressure (ICP) signals are shortly summarized:

Criteria_ICP_PeakValley_Y-WindowSize_MajorDistributionAreaPeaks:
  a) Determine major distribution of peaks 302 to be used for further analysis.
Criteria_ICP_PeakValley_Y-WindowSize_MajorDistributionAreaValleys:
  a) Determine major distribution of valleys 303 to be used for further analysis.
Criteria_ICP_PeakValley_X-WindowSize_GreatestPeakValue:
  a) Determine the size of the window in which only one peak 302 with greatest absolute pressure value remains.
Criteria_ICP_PeakValley_X-WindowSize_LowestValleyValue:
  a) Determine the size of the window in which only one valley 303 with lowest absolute pressure value remains.

It should be noted that the criteria listed here are shown to illustrate the use of said criteria, not to limit the scope of the invention. New and other criteria can be developed for specific types of signals.

As indicated in FIG. 3a, a continuous pressure-related signal 301 involves two dimensions, indicated by a time scale 308 and a pressure scale 309. It is also indicated that all peaks 302 and valleys 303 in said sampled signal 301 are identified during two consecutive time sequence windows, time sequence window no. one 310 and time sequence window no. two 311, each of 6 seconds duration. A time sequence window is a selected time frame of said sampled signal. The duration of said time sequence windows 310, 311 is selectable. For test purposes there were used durations of 6 seconds, though the exact duration of a time sequence represents no limitation of the invention. Preferably the duration of said selectable time sequence lies in the range 5-15 seconds. Each of said selectable time sequence windows is related to a number of time-related sequential pressure samples, each sample referenced by a sample number and elapsed time determined by sample location number and sample frequency. The method is applied to the continuous pressure-related signal for each of said time sequences in a continuous series of said time sequences during a continuous measurement period.

The notation Recording [1].Signals [m].Time sequence [o] denotes a specific Time sequence [o] within a specific Signal [m] within a specific Recording [1].

After determining included pair combinations of peaks 302 and valleys 303 in said signal 301, said Single Wave & Delta Single Wave Criteria (FIG. 2) are used to determine whether said peak 302/valley 303 pairs correspond to pair combinations of diastolic minimum pressure (SW.$P_{min1}$) 307 and systolic maximum pressure (SW.$P_{max}$) 305 that characterize single pressure waves created by the cardiac beat-induced pressure waves. All pair combinations of peaks 302 and valleys 303 correspond to potential pair combinations of SW.StartP$_{min1}$ 307 and SW.$P_{max}$ 305.

For included, i.e. accepted, single pressure waves 312 said peak 302/valley 303 pairs correspond to SW.$P_{max}$ 305/SW.$P_{min1}$ 307 pairs that also correspond to the diastolic minimum pressures and systolic maximum pressures of individual of pressure waves created by each of said cardiac beats. Thereby, each included single pressure wave 312 created by a cardiac beat-induced pressure wave is identified by systolic maximum pressure (SW.$P_{max}$) 305 related to a cardiac beat-induced systolic maximum pressure and a starting diastolic minimum pressure (SW.StartP$_{min1}$) 307 related to a cardiac beat-induced diastolic minimum pressure. The ending diastolic minimum pressure defines an end of a first single pressure wave (SW.$P_{min2}$) 313 which may be the same as the starting diastolic minimum pressure (SW.$P_{min1}$) defining the start of the subsequent second single pressure wave. If there is no subsequent second single pressure wave, the ending diastolic minimum pressure of a first single pressure wave (SW.$P_{min2}$) 313 is not same as the starting diastolic minimum pressure (SW.$P_{min1}$) 307 of another single pressure wave.

Excluded, i.e. rejected, pressure waves 314 contain peak 302/valley 303 pairs that do not meet the Single Wave & Delta Single Wave Criteria (FIG. 2). Said excluded pressure waves 314 are created by artifacts or a combination of cardiac beat- and artifact-induced pressure waves.

The Single Wave & Delta Single Wave Criteria (FIG. 2) applied to the continuous intracranial pressure (ICP) signal is shortly summarized:

Criteria_ICP_Intra-dural_SW.dP:
  a) Amplitude (SW.dP) must be between 1.0 to 35.0 mmHg for pair combinations of SW.$P_{min1}$ 307 and SW.$P_{max}$ 305 to be included for further analysis.
Criteria_ICP_Intra-dural_SW.dT:
  a) Latency (SW.dT) must be between 0.10 to 0.40 seconds for pair combinations of SW.$P_{min1}$ 307 and SW.$P_{max}$ 305 to be included for further analysis.

The specific criteria used in this example are not intended to limit the scope of the invention, but to illustrate application of said criteria. New and other criteria can be developed for specific types of signals, and criteria are determined for all single wave (SW.x)-related parameters and delta single pressure wave (ΔSW.x)-related parameters.

Figure 4A:
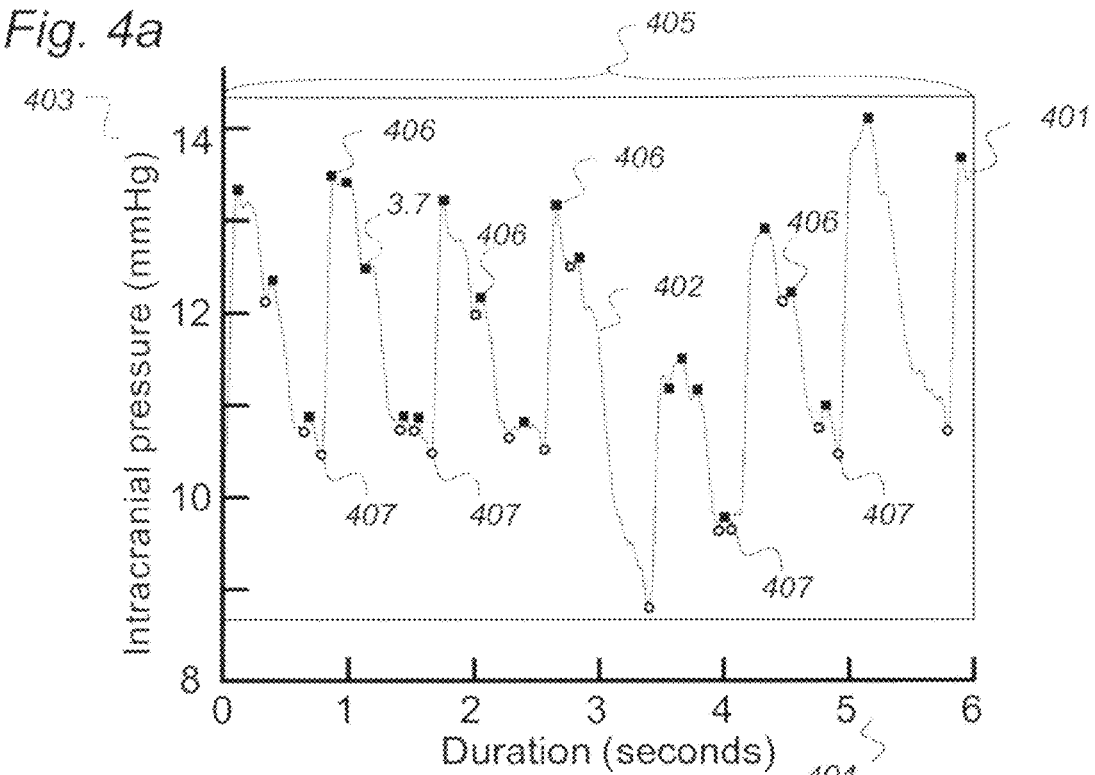
FIG. 4a shows one time sequence window including all identified peaks and valleys.
Figure 4B:
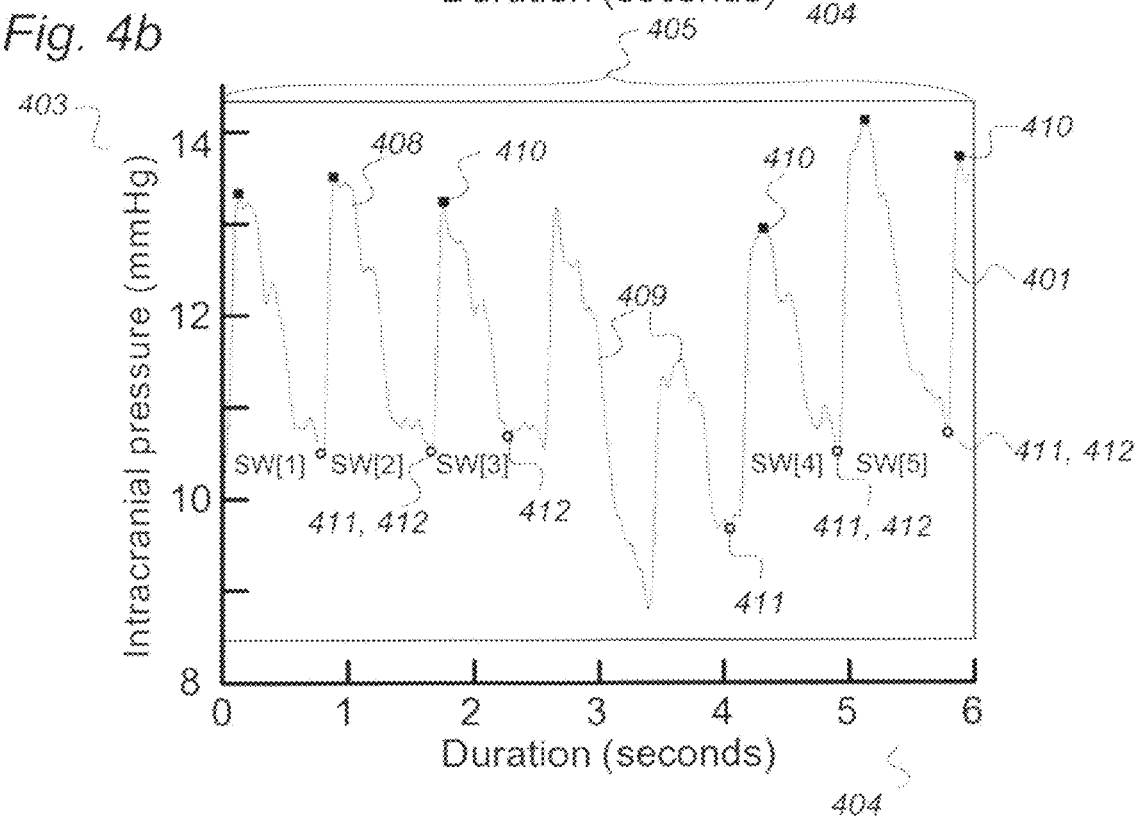
FIG. 4b shows the same time sequence window including only the accepted valley-peak pairs whereby the single pressure wave (SW.x)-related parameters are identified.

The Identifying Steps (FIG. 2) determining included single pressure waves are further illustrated in FIGS. 4a and 4b. In FIG. 4a is shown the step of identifying all separate peaks and valleys, and in FIG. 4b is shown the step of determining included single pressure waves on the basis of included peak/valley pairs. In FIG. 4a is shown a continuous intracranial pressure (ICP) signal 401 including pressure waves 402. The two dimensions of the pressure signal are indicated, namely the pressure scale 403 and the time scale 404. Only one time sequence window 405 of the continuous pressure signal 401 is shown (Recording[46].Signal[1]TimeSequence[360]), including all twenty-two identified peaks 406 (filled squares) and all seventeen identified valleys 407 (open circles). Each of said peaks 406 is a sample with a pressure value and a time stamp or location, and each of said valleys 407 is a sample with a pressure value and a time stamp or location.

Further application of the General Methods Criteria (FIG. 2) determine included pair combinations of peaks 406 and valleys 407 in said signal 401.

Application of the Single Wave & Delta Single Wave Criteria (FIG. 2) to these included peak 406/valley 407 pairs determine included single pressure waves 408 and excluded single pressure waves 409 within said time sequence window 405 (Recording[46].Signal[1]TimeSequence[360]).

Only two sets of Single Wave & Delta Single Wave Criteria were applied to the peak 406/valley 407 pairs shown in FIG. 4a:

Amplitude (SW.dP) must be between 1.0 to 35.0 mmHg for peak 406/valley 407 pairs to be included for further analysis (=Criteria_ICP_Intra-dural_SW.dP); and latency (SW.dT) must be between 0.10 to 0.40 seconds for peak 406/valley 407 pairs to be included for further analysis (=Criteria_ICP_Intra-dural_SW.dT).

Included peak 406/valley 407 pairs correspond to included, i.e. accepted, pair combinations of systolic maximum pressure (SW.P$_{max}$) 410 and starting diastolic minimum pressure (SW.P$_{min1}$) 411, characterizing included single pressure waves 408 that are created by the cardiac beat-induced pressure waves. Said included single pressure waves 408 (identified by included SW.P$_{max}$ 410/SW.P$_{min1}$ 411 pairs) are shown in FIG. 4b (termed SW[1], SW[2], SW[3], SW[4], and SW[5]). The ending diastolic minimum pressure (SW.P$_{min2}$) 412 defining an end of single pressure wave three (SW[3]) is notably not the same as starting diastolic minimum pressure (SW.P$_{min1}$) 411 defining the start of single pressure wave four (SW[4]). On the other hand, the ending diastolic minimum pressure (SW.P$_{min2}$) 412 defining an end of single pressure wave four (SW[4]) is the same as the beginning diastolic minimum pressure (SW.P$_{min1}$) 411 defining the start of single pressure wave five (SW[5]). Said excluded pressure waves 409 (identified as excluded, i.e. rejected, peak 406/valley 407 pairs) are also indicated in FIG. 4b, shown as the two pressure waves between single pressure wave three (SW[3]) and four (SW[4]). A visual inspection of the pressure waves 402 shown in FIGS. 4a and 4b suggest that also the two excluded pressure waves 409 might have been included, given another set of Single Wave & Delta Single Wave Criteria. Thus, the output of the Identifying Steps (FIG. 2) applied to the peaks 406 and valleys 407 shown in FIG. 4a and further shown in FIG. 4b illustrate the fact that the General Methods Criteria and Single Wave & Delta Single Wave Criteria heavily influence the proportion of included single pressure waves 408 and excluded pressure waves 409.

The time sequence window 405 (TimeSequence[360]) shown in FIGS. 4a and 4b is one individual of said time sequence windows 405 in a continuous series of time sequence windows 405 (TimeSequence[1] to TimeSequence [4665]) during this particular recording (Recording[46]): Recording[46].Signal[1].TimeSequence[360].

The method is applied to each of said time sequence windows 405. To further evaluate the included single pressure waves 408 within said time sequence window 405, said Time Sequence & Delta Time Sequence Criteria (FIG. 2) are applied. Only one criterion was applied to the time sequence window 405 shown in FIGS. 4a and 4b (TimeSequence [360]), namely that TS.SWCount must be between 4 and 18 counts (=Criteria_ICP_TS.SWCount_SWCountRange). The output of applying said criteria are either included, i.e. accepted, or excluded, i.e. rejected, time sequence windows (see FIG. 2), wherein the time sequence window shown in FIG. 4b is an included time sequence window.

A subgroup of selected Time Sequence and Delta Time Sequence Criteria define whether single pressure waves 408 which occur between two consecutive of said time sequence windows 405 are to be placed within one or the other of said two consecutive individual time sequence windows. Said selected criteria define that a first of said single pressure waves (e.g. SW[1]; FIG. 4b) 408 within said individual time sequence window 405 must have its ending diastolic minimum pressure value (SW.P$_{min2}$) 412 within said individual time sequence window 405. Said selected criteria also define that a last of said single pressure waves (e.g. SW[5]; FIG. 4b) 408 within said individual time sequence window 405 must have both its starting diastolic minimum pressure value (SW.P$_{min1}$) 411 and its ending diastolic minimum pressure value (SW.P$_{min2}$) 412 within said individual time sequence window 405. On this basis, the SW.P$_{min1}$ 411/SW.P$_{max}$ 410 pair combination subsequent to single pressure wave five (SW[5]) is not included (is disregarded) within this particular time sequence window 405 (TimeSequence[360]). The starting diastolic minimum pressure value (SW.P$_{min1}$) 411 of this SW.P$_{min1}$ 411/SW.P$_{max}$ 410 pair is the same as the ending diastolic minimum pressure value (SW.P$_{min1}$) 412 of single pressure wave five (SW[5]). This SW.P$_{min1}$ 411/SW.P$_{max}$ 410 pair was not included within this time sequence window 405 due to no identified ending diastolic minimum pressure value (SW.P$_{min2}$) 412 within said individual time sequence window 405.

An important issue is how to verify that included single pressure waves 408 determined as SW.P$_{min1}$ 411/SW.P$_{max}$ 410 pair combinations correspond to cardiac beat-induced pressure waves. The verification process may either be manual or automatic. During manual verification, visual inspection of valley 407/peak 406 pair detections (or SW.P$_{min1}$ 411/SW.P$_{max}$ 410 pair detections) is performed for individual signals 401 of individual recordings. It is visually inspected how changes in sets of criteria (i.e. General Methods Criteria, Single Wave & Delta Single Wave Criteria, and/or Time Sequence & Delta Time Sequence Criteria) modify said detections of valley 407/peak 406 pairs and/or SW.P$_{min1}$ 411/SW.P$_{max}$ 410 pairs. During automatic verification, detections of valley 407/peak 406 pairs and/or SW.P$_{min1}$ 411/SW.P$_{max}$ 410 pairs may be compared against a reference material. Such a reference material may be another signal within an identical recording, wherein samples are obtained from each respective one of said pressure related signals, each such sample containing a pressure value at a specific time, and wherein said two or more pressure related signals are all sampled simultaneously.

Examples of such simultaneous pressure-related signals are continuous invasive intracranial pressure (ICP) and arterial blood pressure (ABP) signals. Instead of a continuous pressure related signal a continuous electrocardiogram (ECG) signal may as well be selected. A continuous electrocardiogram (ECG) signal gives a very precise heartbeat corresponding to the cardiac beat-induced heartbeats. Thus, during automatic verification of detections of location of starting diastolic minimum pressure values (SW.$P_{min1}$) 412, comparisons are made against location of diastolic minimum pressure derived from electrocardiogram (ECG) signals. It should be noted, however, that there could be a delay in time (milliseconds) between sampled ECG and ICP signals caused by natural technical causes. The ICP's observed SW.$P_{min1}$.Locations will natural be within a constant delay compared to the ECG's observed SW.$P_{min1}$.Locations. Nevertheless, the heartbeat duration should be identical. Another method for automatic verification is made by recalculating all available manually verified recordings whenever criteria are changed or methodological improvements are made. Such a recalculation can be automatically compared against the reference result.

During the Identification Steps the output is included time sequence windows after application of the Time Sequence & Delta Time Sequence Criteria (see FIG. 2). Based on said included time sequence windows, a number of parameters: single wave (SW.x)-related parameters, delta single pressure wave (ΔSW.x)-related parameters, time sequence (TS.x)-related parameters, and delta time sequence (ΔTS.x)-related parameters are obtainable. In the following paragraphs reference is given to these parameters.

Figure 5A:
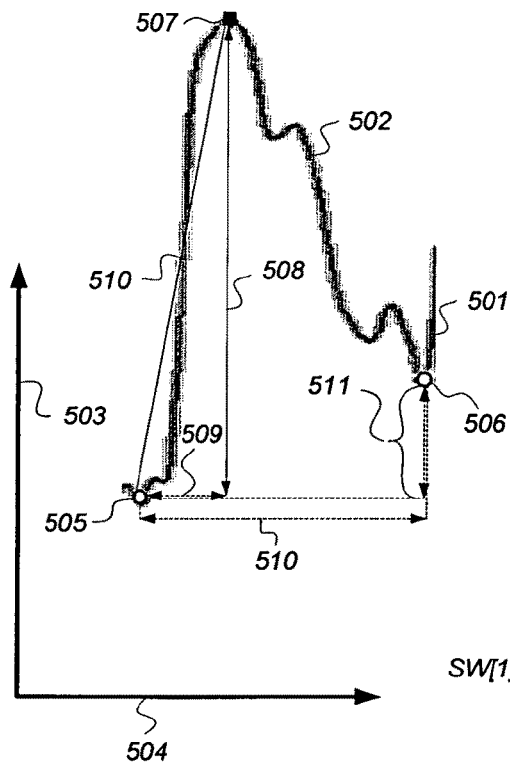
FIG. 5a shows one individual single pressure wave including single pressure wave (SW.x)-related parameters.

Reference is now given to FIG. 5a focusing on single wave (SW.x)-related parameters. Within a continuous pressure-related signal 501, one individual of said included single pressure waves 502 is shown: Recording[46].Signal[1].TimeSequence[360].SingleWave[4]. This single pressure wave is created by one individual cardiac beat. First, it should be noted that a continuous pressure-related signal 501 involves two dimensions, namely a pressure scale 503 and a time scale 504. Both dimensions have to be considered when describing a continuous pressure-related signal 501. Therefore, single pressure wave (SW.x)-related parameters are with reference to time location and pressure level value. For example, the parameter starting diastolic minimum pressure (SW.$P_{min1}$) 505 involves the two values SW.$P_{min1}$.Location (referring to time stamp location) and SW.$P_{min1}$.Value (referring to pressure level value). This aspect must be remembered for the various single pressure wave (SW.x)-related parameters, though reference is not specifically given to time location and pressure level value when referring to these parameters.

The single pressure wave (SW.x)-related parameters computed during said selected time sequence windows are selected from the group of:

starting diastolic minimum pressure defining the start of the single pressure wave (SW.$P_{min1}$) 505, as further detailed in equation (1):

SW[n].$P_{min1}$.Value=Signal.Samples[SW[n].$P_{min1}$.Location]     (1)

ending diastolic minimum pressure defining the end of the single pressure wave (SW.$P_{min2}$) 506, as further detailed in equation (2):

SW[n].$P_{min2}$.Value=Signal.Samples[SW[n].$P_{min2}$.Location]     (2)

single wave sample count defining the number of samples within a single pressure wave, as further detailed in equation (3):

SW[n].SampleCount=SW[n].$P_{min2}$.Location−SW[n].$P_{min1}$.Location     (3)

systolic maximum pressure of the single pressure wave (SW.$P_{max}$) 507, as further detailed in equation (4):

SW[n].$P_{max}$.Value=Signal.Samples[SW[n].$P_{max}$.Location]     (4)

amplitude of the single pressure wave (SW.dP) 508, as further detailed in equation (5):

SW[n].dP=SW[n].$P_{max}$.Value−SW[n].$P_{min1}$.Value     (5)

latency of the single pressure wave (SW.dT) 509, as further detailed in equation (6):

SW[n].dT=SW[n].$P_{max}$.Location−SW[n].$P_{min1}$.Location)/Signal.Frequency     (6)

rise time coefficient of the single pressure wave (SW.RT), as further detailed in equation (7):

SW[n].RT=SW[n].dP/SW[n].dT     (7)

wave duration of the single pressure wave (SW.WD) 510, as further detailed in equation (8):

SW[n].WD=SW[n].SampleCount/Signal.Frequency     (8)

mean single wave pressure of the single pressure wave (SW.$Mean_{SW}P$), as further detailed in equation (9):

$$SW[n].Mean_{SW}P = \frac{\sum_{loc=SW[n].P_{min1}}^{SW[n].P_{min2}-1}(Signal.Samples[loc])}{SW[n].SampleCount} \quad (9)$$

diastolic minimum pressure difference of the single pressure wave (SW.Diff_$P_{min}$) 511, as further detailed in equation (10):

SW[n].Diff_$P_{min}$=SW[n].$P_{min2}$.Value−SW[n].$P_{min1}$.Value     (10)

The ending diastolic minimum pressure (SW.$P_{min2}$) 506 defines an end of a single pressure wave 502, and the starting diastolic minimum pressure (SW.$P_{min1}$) 505 defines the start of a single pressure wave 502. Said single pressure wave amplitude (=SW.dP) 508 equals systolic maximum pressure value (SW.$P_{max}$.Value) 507 minus starting diastolic minimum pressure value (SW.$P_{min1}$.Value) 506. Single pressure wave latency (=SW.dT) 509 equals time duration starting diastolic minimum pressure (SW.$P_{min1}$.Location) 505 to systolic maximum pressure (SW.$P_{max}$.Location) 507. Single pressure rise time coefficient relates to the relationship between amplitude (SW.dP) 508 and latency (SW.dT) 509 (SW.RT=SW.dP/SW.dT). Wave duration (SW.WD) 510 for each individual of said single pressure waves 502 relates to the time duration between starting diastolic minimum pressure (SW.$P_{min1}$) 505 and ending diastolic minimum pressure (SW.$P_{min2}$) 506. Diastolic minimum pressure difference (SW.Diff_$P_{min}$) relates to pressure difference between starting and ending diastolic minimum values (SW.$P_{min1}$ 505 versus SW.$P_{min2}$ 506) of one individual of said single pressure waves 502.

Mean single wave pressure (SW.$Mean_{SW}P$) for each individual of said single pressure waves 502 relates to absolute mean pressure during the time of the wave duration, i.e. from starting diastolic minimum pressure (SW.$P_{min1}$) 505 to ending diastolic minimum pressure (SW.$P_{min2}$) 506. Mean pressure for an individual single pressure wave (SW.$Mean_{SW}P$) is the sum of sample values within said pressure wave divided by numbers of samples.

Except for mean single wave pressure (SW.$Mean_{SW}P$), all single wave (SW.x)-related parameters are relative values in either pressure or time. The relative pressure levels are crucial in the way that these relative values are independent on zero pressure level or drift in zero pressure level.

Figure 5B:
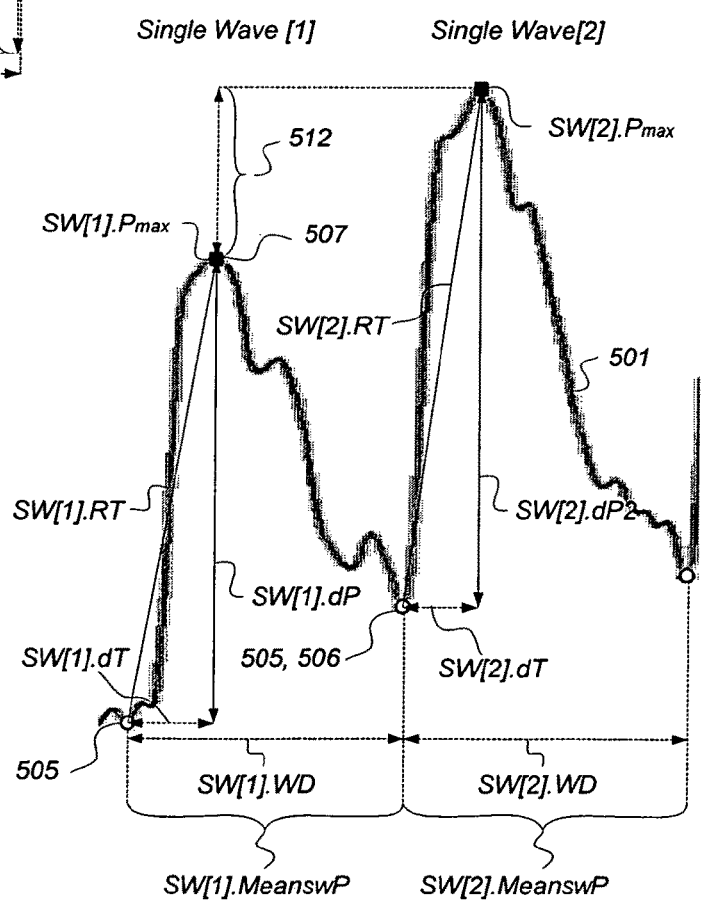
FIG. 5b shows two subsequent single pressure waves (n−1;n) including single pressure wave (SW.x)- and delta single wave (ΔSW.x)- related parameters.

In FIG. 5b the first single pressure wave 502 is termed Single Wave[1] (n−1) and the subsequent and second single pressure wave 502 is termed Single Wave[2] (n). As indicated (FIG. 5b), the ending diastolic minimum pressure (SW.$P_{min2}$) 506 of Single Wave[1] also is starting diastolic minimum pressure (SW.$P_{min1}$) 505 of Single Wave[2]. In another situation, the ending diastolic minimum pressure (SW.$P_{min2}$) 506 of a first single pressure wave is not the same as starting diastolic minimum pressure (SW.$P_{min1}$) 505 of a subsequent second single pressure wave, provided that this second single pressure wave is not following immediately after the first one.

The delta single pressure wave (ΔSW.x)-related parameters during said selected time sequence windows are illustrated in FIG. 5b, wherein the parameters are selected from the group of:

systolic maximum pressure difference between two subsequent (n−1;n) single pressure waves (ΔSW.Diff_$P_{max}$) 512, as further detailed in equation (11):

$$\Delta SW[n].\text{Diff\_}P_{max} = SW[n].P_{max}.\text{Value} - SW[n-1].P_{max}.\text{Value} \quad (11)$$

amplitude difference between two subsequent single pressure waves (ΔSW.Diff_dP), as further detailed in equation (12):

$$\Delta SW[n].\text{Diff\_}dP = SW[n].dP - SW[n-1].dP \quad (12)$$

latency difference between two subsequent single pressure waves (ΔSW.Diff_dT), as further detailed in equation (13):

$$\Delta SW[n].\text{Diff\_}dT = SW[n].dT - SW[n-1].DT \quad (13)$$

rise time coefficient difference between two subsequent single pressure waves (ΔSW.Diff_RT), as further detailed in equation (14):

$$\Delta SW[n].\text{Diff\_}RT = SW[n].RT - SW[n-1].RT \quad (14)$$

wave duration difference between two subsequent single pressure waves (ΔSW.Diff_WD), as further detailed in equation (15):

$$\Delta SW[n].\text{Diff\_}WD = SW[n].WD - SW[n-1].WD \quad (15)$$

mean single wave pressure difference between two subsequent single pressure waves (ΔSW.Diff_Mean$_{SW}$P), as further detailed in equation (16):

$$\Delta SW[n].\text{Diff\_Mean}_{SW}P = SW[n].\text{Mean}_{SW}P - SW[n-1].\text{Mean}_{SW}P \quad (16)$$

Two subsequent single pressure waves (n−1;n) represent a current single pressure wave SW[n].x in time n subtracted from the previous SW[n−1].x in time n−1 of said individual time sequence window.

As indicated in FIG. 5b, systolic maximum pressure difference (SW.Diff_$P_{max}$) 512 relates to pressure difference between systolic maximum pressure (SW.$P_{max}$) 507 values of two subsequent of said single pressure waves (SW[2].$P_{max}$−SW[1].$P_{max}$; FIG. 5b). Amplitude difference (SW.Diff_dP) relates to difference in single pressure wave amplitudes (SW.dP) 508 of two subsequent of said single pressure waves (SW[2].dP−SW[1].dP; FIG. 5b). Latency difference (SW.Diff_dT) relates to difference in single pressure wave latency (SW.dT) 509 of two subsequent of said single pressure waves (SW[2].dT−SW[1].dT; FIG. 5b). Rise time coefficient difference (SW.Diff_RT) relates to difference in single pressure wave rise time coefficient (SW.RT) of two subsequent of said single pressure waves (SW[2].RT−SW[1].RT; FIG. 5b). Wave duration difference (SW.Diff_WD) relates to difference of wave duration (SW.WD) 510 between two subsequent of said single pressure waves (SW[2].WD−SW[1].WD; FIG. 5b). Mean single wave pressure difference (SW.Diff_Mean$_{SW}$P) relates to difference of mean single wave pressure (Mean$_{SW}$P) between two subsequent of said single pressure waves (SW[2].Mean$_{SW}$P−SW[1].Mean$_{SW}$P; FIG. 5b). The delta single pressure wave (ΔSW.x)-related parameters are all relative values.

Test recordings show that delta single pressure wave (ΔSW.x)-related parameters have an important role in the verification process assessing the quality of continuous pressure signals. In the presence of bad signal quality, the delta single pressure wave (ΔSW.x)-related parameters have greater values than in the presence of good signal quality.

Figure 6:
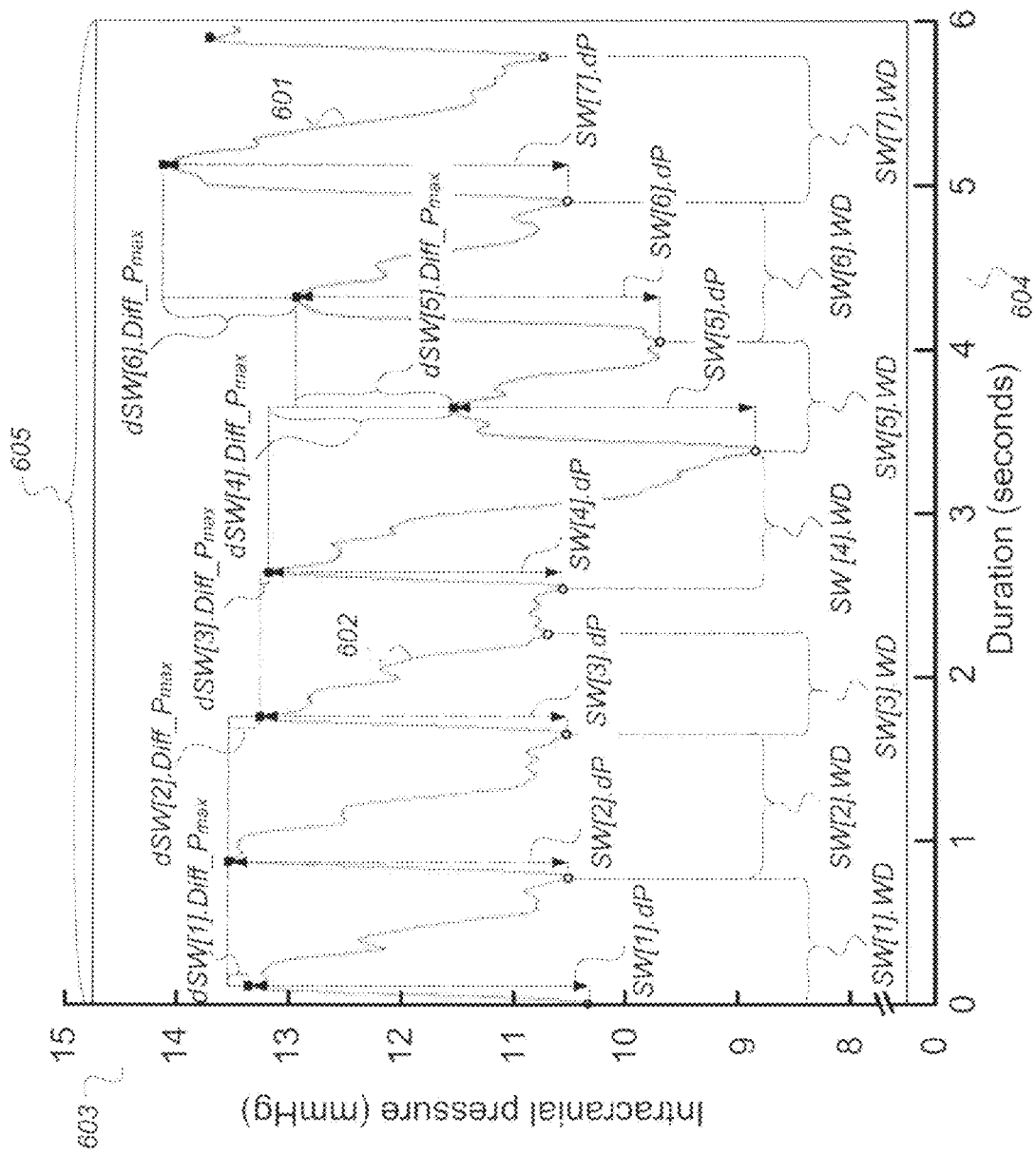
FIG. 6 shows one individual time sequence window including various time-sequences (TS.x)-related parameters.

Reference is now given to computation of time sequence (TS.x)-related parameters. In FIG. 6 is shown a continuous intracranial pressure (ICP) signal 601, including the included (i.e. accepted) single pressure waves 602. The two dimensions of a continuous pressure signal 601 are indicated by the pressure scale 603 and the time scale 604. One individual time sequence window 605 is shown, revealing that the selectable duration was 6 seconds in this case. It is illustrated that said selectable time sequence window 605 is a selected time frame of said sampled signal 601. Time sequence (TS.x)-related parameters are computed for each of said individual time sequence windows 605, based on included single pressure waves 602 within said individual time sequence window 605. For this particular time sequence window 605 there are seven included single pressure waves 602, indicated by the wave durations (WD) of said waves 602 (termed SW[1].WD, SW[2].WD, SW[3].WD, SW[4].WD, SW[5].WD, SW[6].WD, and SW[7].WD). For said included single pressure waves 602 are as well indicated the amplitudes (SW.dP) (termed SW[1].dP, SW[2].dP, SW[3].dP, SW[4].dP, SW[5].dP, SW[6].dP, and SW[7].dP). In addition is shown the systolic maximum pressure difference between two subsequent (n−1;n) single pressure waves (ΔSW.Diff_$P_{max}$) (termed ΔSW[1].Diff_$P_{max}$, ΔSW[2].Diff_$P_{max}$, ΔSW[3].Diff_$P_{max}$, ΔSW[4].Diff_$P_{max}$, ΔSW[5].Diff_$P_{max}$, and ΔSW[6].Diff_$P_{max}$).

According to this invention there is identified a number of said time sequence (TS.x)-related parameters of said single pressure waves 602 during individual of said time sequence windows 605, said parameters selected from the group of:

mean value of starting diastolic minimum pressures of a time sequence window (TS.MeanP$_{min1}$), as further detailed in equation (17):

$$TS[i].\text{MeanP}_{min1} = \frac{\sum_{n=1}^{TS[n].SWCount} SW[n].P_{min1}.\text{Value}}{TS[i].SWCount} \quad (17)$$

standard deviation of mean value of starting diastolic minimum pressures of a time sequence window (TS.MeanP$_{min1}$_STD), as further detailed in equation (18):

$$TS[i].\text{MeanP}_{min1}\_STD = \sqrt{\frac{\sum_{n=1}^{TS[i].SWCount} (SW[n].P_{min1}.\text{Value} - TS[i].\text{MeanP}_{min1})^2}{TS[i].SWCount}} \quad (18)$$

mean value of systolic maximum pressures of a time sequence window (TS.MeanP$_{max}$), as further detailed in equation (19):

$$TS[i].MeanP_{max} = \frac{\sum_{n=1}^{TS[i].SWCount} SW[n].P_{max}.Value}{TS[i].SWCount} \quad (19)$$

standard deviation of mean value of systolic maximum pressures of a time sequence window (TS.MeanP$_{max\_}$STD), as further detailed in equation (20):

$$TS[i].MeanP_{max}\_STD = \quad (20)$$
$$\sqrt{\frac{\sum_{n=1}^{TS[i].SWCount}(SW[n].P_{max}.Value - TS[i].MeanP_{max})^2}{TS[i].SWCount}}$$

mean amplitude of a time sequence window (TS.MeandP), as further detailed in equation (21):

$$TS[i].MeandP = \frac{\sum_{n=1}^{TS[i].SWCount} SW[n].dP}{TS[i].SWCount} \quad (21)$$

standard deviation of mean amplitude of a time sequence window (TS.MeandP_STD), as further detailed in equation (22):

$$TS[i].MeanP\_STD = \sqrt{\frac{\sum_{n=1}^{TS[i].SWCount}(SW[n].dP - TS[i].MeandP)^2}{TS[i].SWCount}} \quad (22)$$

mean latency of a time sequence window (TS.MeandT), as further detailed in equation (23):

$$TS[i].MeandT = \frac{\sum_{n=1}^{TS[i].SWCount} SW[n].dT}{TS[i].SWCount} \quad (23)$$

standard deviation of mean latency of a time sequence window (TS.MeandT_STD), as further detailed in equation (24):

$$TS[i].MeandT\_STD = \sqrt{\frac{\sum_{n=1}^{TS[i].SWCount}(SW[n].dT - TS[i].MeandT)^2}{TS[i].SWCount}} \quad (24)$$

mean rise time coefficient of a time sequence window (TS.MeanRT), as further detailed in equation (25):

$$TS[i].MeanRT = \frac{\sum_{n=1}^{TS[i].SWCount} SW[n].RT}{TS[i].SWCount} \quad (25)$$

standard deviation of mean rise time coefficient of a time sequence window (TS.MeanRT_STD), as further detailed in equation (26):

$$TS[i].MeanRT\_STD = \quad (26)$$
$$\sqrt{\frac{\sum_{n=1}^{TS[i].SWCount}(SW[n].RT - TS[i].MeanRT)^2}{TS[i].SWCount}}$$

mean wave duration of a time sequence window (TS.MeanWD), as further detailed in equation (27):

$$TS[i].MeanWD = \frac{\sum_{n=1}^{TS[i].SWCount} SW[n].WD}{TS[i].SWCount} \quad (27)$$

standard deviation of mean wave duration of a time sequence window (TS.MeanWD_STD), as further detailed in equation (28):

$$TS[i].MeanWD\_STD = \quad (28)$$
$$\sqrt{\frac{\sum_{n=1}^{TS[i].SWCount}(SW[n].WD - TS[i].MeanWD)^2}{TS[i].SWCount}}$$

mean single wave pressure of a time sequence window (TS.Mean$_{SW}$P), as further detailed in equation (29):

$$TS[i].Mean_{SW}P = \frac{\sum_{n=1}^{TS[i].SWCount} SW[n].Mean_{SW}P}{TS[i].SWCount} \quad (29)$$

standard deviation of mean single wave pressure of a time sequence window (TS.Mean$_{SW}$P_STD), as further detailed in equation (30):

$$TS[i].Mean_{SW}P\_STD = \quad (30)$$
$$\sqrt{\frac{\sum_{n=1}^{TS[i].SWCount}(SW[n].Mean_{SW}P - TS[i].Mean_{SW}P)^2}{TS[i].SWCount}}$$

mean of diastolic minimum pressure differences of a time sequence window (TS.MeanDiff_P$_{min}$), as further detailed in equation (31):

$$TS[i].\text{MeanDiff\_P}_{min} = \frac{\sum_{n=1}^{TS[i].SWCount} SW[n].\text{Diff\_P}_{min}}{TS[i].SWCount} \quad (31)$$

standard deviation of mean of diastolic minimum pressure differences of a time sequence window (TS.MeanDiff_$P_{min}$_STD), as further detailed in equation (32):

$$TS[i].\text{MeanDiff\_P}_{min}\_STD = \quad (32)$$
$$\sqrt{\frac{\sum_{n=1}^{TS[i].SWCount}\left(SW[n].\text{Diff\_P}_{min} - TS[i].\text{MeanDiff\_P}_{min}\right)^2}{TS[i].SWCount}}$$

mean of systolic maximum pressure differences of a time sequence window (TS.MeanDiff_$P_{max}$), as further detailed in equation (33):

$$TS[i].\text{MeanDiff\_P}_{max} = \frac{\sum_{n=2}^{TS[i].SWCount} \Delta SW[n].P_{max}.Value}{TS[i].SWCount - 1} \quad (33)$$

standard deviation of mean of systolic maximum pressure differences of a time sequence window (TS.MeanDiff_$P_{max}$_STD), as further detailed in equation (34):

$$TS[i].\text{MeanDiff\_P}_{max}\_STD = \quad (34)$$
$$\sqrt{\frac{\sum_{n=2}^{TS[i].SWCount}(\Delta SW[n].P_{max}.Value - TS[i].\text{MeanDiff\_P}_{max})^2}{TS[i].SWCount - 1}}$$

mean amplitude difference of a time sequence window (TS.MeanDiff_dP), as further detailed in equation (35):

$$TS[i].\text{MeanDiff\_dP} = \frac{\sum_{n=2}^{TS[i].SWCount} \Delta SW[n].dP}{TS[i].SWCount - 1} \quad (35)$$

standard deviation of mean amplitude difference of a time sequence window (TS.MeanDiff_dP_STD), as further detailed in equation (36):

$$TS[i].\text{MeanDiff\_dP\_STD} = \quad (36)$$
$$\sqrt{\frac{\sum_{n=2}^{TS[i].SWCount}(\Delta SW[n].dP - TS[i].\text{MeanDiff\_dP})^2}{TS[i].SWCount - 1}}$$

mean latency difference of a time sequence window (TS.MeanDiff_dT), as further detailed in equation (37):

$$TS[i].\text{MeanDiff\_dT} = \frac{\sum_{n=2}^{TS[i].SWCount} \Delta SW[n].dT}{TS[i].SWCount - 1} \quad (37)$$

standard deviation of mean latency difference of a time sequence window (TS.MeanDiff_dT_STD), as further detailed in equation (38):

$$TS[i].\text{MeanDiff\_dT\_STD} = \quad (38)$$
$$\sqrt{\frac{\sum_{n=2}^{TS[i].SWCount}(\Delta SW[n].dT - TS[i].\text{MeanDiff\_dT})^2}{TS[i].SWCount - 1}}$$

mean rise time coefficient difference of a time sequence window (TS.MeanDiff_RT), as further detailed in equation (39):

$$TS[i].\text{MeanDiff\_RT} = \frac{\sum_{n=2}^{TS[i].SWCount} \Delta SW[n].RT}{TS[i].SWCount - 1} \quad (39)$$

standard deviation of mean rise time coefficient difference of a time sequence window (TS.MeanDiff_RT_STD), as further detailed in equation (40):

$$TS[i].\text{MeanDiff\_RT\_STD} = \quad (40)$$
$$\sqrt{\frac{\sum_{n=2}^{TS[i].SWCount}(\Delta SW[n].RT - TS[i].\text{MeanDiff\_RT})^2}{TS[i].SWCount - 1}}$$

mean wave duration difference of a time sequence window (TS.MeanDiff_WD), as further detailed in equation (41):

$$TS[i].\text{MeanDiff\_WD} = \frac{\sum_{n=2}^{TS[i].SWCount} \Delta SW[n].WD}{TS[i].SWCount - 1} \quad (41)$$

standard deviation of mean wave duration difference of a time sequence window (TS.MeanDiff_WD_STD), as further detailed in equation (42):

$$TS[i].\text{MeanDiff\_WD\_STD} = \quad (42)$$
$$\sqrt{\frac{\sum_{n=2}^{TS[i].SWCount}(\Delta SW[n] \cdot WD - TS[i].\text{MeanDiff\_WD})^2}{TS[i].SWCount - 1}}$$

mean single wave pressure difference of a time sequence window (TS.MeanDiff_Mean$_{SW}$P), as further detailed in equation (43):

$$TS[i].\text{MeanDiff\_Mean}_{SW}P = \frac{\sum_{n=2}^{TS[i].SWCount} \Delta SW[n].\text{Mean}_{SW}P}{TS[i].SWCount - 1} \quad (43)$$

standard deviation of mean single wave pressure difference of a time sequence window (TS.MeanDiff_Mean$_{SW}$P_STD), as further detailed in equation (44):

$$TS[i].\text{MeanDiff\_Mean}_{SW}P\_STD = \sqrt{\frac{\sum_{n=2}^{TS[i].SWCount} (\Delta SW[n].\text{Mean}_{SW}P - TS[i].\text{MeanDiff\_Mean}_{SW}P)^2}{TS[i].SWCount - 1}} \quad (44)$$

numbers of accepted single pressure waves of a time sequence window (TS.SWCount), wherein: TS[i].SWCount=Number of included single pressure waves within a time sequence window, mean wave amplitude of a time sequence window computed according to the first matrix (TS.MeanWavedP) (see separate description with reference to FIG. 8), mean wave latency of a time sequence window computed according to the first matrix (TS.MeanWavedT) (see separate description with reference to FIG. 8), mean wave rise time coefficient of a time sequence window computed according to the second matrix (TS.MeanWaveRT)) (see separate description with reference to FIG. 8).

Mean amplitude during said time sequence window 605 (TS.MeandP) is the sum of amplitude values for all individual single pressure waves 602 during said time sequence window 605 divided by the number of single pressure waves 602 within said time sequence window 605. With reference to FIG. 6, the equation is as follows: TS.MeandP=(SW[1].dP+SW[2].dP+SW[3].dP+SW[4].dP+SW[5].dP+SW[6].dP+SW[7].dP)/7. Mean of systolic maximum pressure differences during a time sequence window (TS.MeanDiff_P$_{max}$) is the sum of systolic maximum pressure differences between two subsequent (n−1;n) single pressure waves (ΔSW.Diff_P$_{max}$) values when considering all individual single pressure waves 602 during said time sequence window 605 divided by the number of single pressure waves minus one 602 within said time sequence window 605. With reference to FIG. 6, the equation is as follows: TS.MeanDiff_P$_{max}$=(ΔSW[1].Diff_P$_{max}$+ΔSW[2].Diff_P$_{max}$+ΔSW[3].Diff_P$_{max}$+ΔSW[4].Diff_P$_{max}$+ΔSW[5].Diff_P$_{max}$+ΔSW[6].Diff_P$_{max}$)/6. It should be noted that with reference to ΔSW.Diff_P$_{max}$, the symbol d is used in FIG. 6 instead of the symbol Δ. Mean wave duration of a time sequence window (TS.MeanWD) is the sum of wave duration (SW.WD) values for all individual single pressure waves 602 during said time sequence window 605 divided by the number of single pressure waves 602 within said time sequence window 605. With reference to FIG. 6, the equation is as follows: TS.MeanWD=(SW[1].WD+SW[2].WD+SW[3].WD+SW[4].WD+SW[5].WD+SW[6].WD+SW[7].WD)/7.

Mean latency during said time sequence window 605 (TS.MeandT) is the sum of latency values for all individual single pressure waves 602 during said time sequence window 605 divided by the number of single pressure waves 602 within said time sequence window 605. Mean rise time coefficient during said time sequence window 605 (TS.MeanRT) is the sum of mean rise time coefficient values for all individual single pressure waves 602 during said time sequence window divided by the numbers of single pressure waves 602 within said time sequence window 605. Mean single wave pressure during said time sequence window 605 (TS.Mean$_{SW}$P) is the sum of absolute mean pressure, i.e. related to wave duration extending from SW.P$_{min1}$.Location to SW.P$_{min2}$.Location-1 for all individual single pressure waves 602 during said time sequence window 605 divided by the number of single pressure waves 602 within said time sequence window 605. It should be noted that mean single wave pressure (TS.Mean$_{SW}$P) relates to absolute pressure relative to atmospheric pressure.

Mean wave amplitude during said time sequence window 605 (TS.MeanWavedP) is computed according to a first matrix as balanced position in said matrix of number of occurrences of amplitude (SW.dP) and latency (SW.dT) values for all individual single pressure waves 602 during said time sequence window 605. Mean wave latency during said time sequence window (TS.MeanWavedT) is computed according to said first matrix as balanced position in said matrix number of occurrences of amplitude (SW.dP) and latency (SW.dT) values for all individual single pressure waves 602 during said time sequence window 605. Mean wave rise time coefficient during said time sequence window 605 (TS.MeanWaveRT) is computed according to a second matrix as balanced position in said second matrix of number of occurrences of rise time coefficient values (SW.RT) for all individual single pressure waves 602 during said time sequence window 605.

Mean wave duration difference during said time sequence window 605 (TS.MeanDiff_WD) is the mean value of all ΔSW.Diff_WD between subsequent single pressure waves 602 during said time sequence window 605 divided by numbers of single pressure waves 602 during said time sequence window 605. With reference to FIG. 6, the equation is as follows: TS.MeanDiff_WD=[(SW[2].WD−SW[1].WD)+(SW[3].WD−SW[2].WD)+(SW[4].WD−SW[3].WD)+(SW[5].WD−SW[4].WD)+(SW[6].WD−SW[5].WD)+(SW[7].WD−SW[6].WD)]/6.

The time sequence (TS.x)-related parameters can be considered as the "building blocks" of the inventive method of processing continuous pressure-related signals, and represents a key element of the invention. Time sequence (TS.x) parameters computed from time sequence windows of good signal quality (i.e. single pressure waves are created by cardiac beat-induced pressure waves) provide for completely new information about pressure measurements, not revealed by current and prior art technology. These important significance areas relate to aspects such as e.g.:

a) Quality control. Whether or not the pressure signal is good or bad is determined by TS.x-related parameters such as e.g. TS.MeanP$_{min1}$_STD, TS.MeanP$_{max}$_STD, TS.MeandP_STD, TS.MeandT_STD, TS.MeanWD, TS.MeanWD_STD, TS.MeanDiff_P$_{min}$ and TS.SWCount.

b) New diagnostic information. Whether or not pressures are abnormally high or not are determined by TS.x-related parameters such as e.g. TS.MeandP, TS.MeanRT, TS.Mean$_{SW}$P, TS.MeanWavedP, TS.MeanWavedT, and TS.MeanWaveRT. Such information is not derived from current and prior art technology.

c) New pressure comparisons method. Two or more simultaneous signals constituting a pressure recording can be compared to determine relationships between said signals using said TS.x parameters such as e.g. TS.MeandP, TS.MeandP_STD, TS.MeanRT, TS.MeanRT_STD, TS.MeanDiff_dP, TS.MeanDiff_dP_STD.

d) Relationship determination. Concerning the topic of processing signals derived from outside or inside a human or animal body cavity, it is crucial to determine relationships between TS.x-related parameters involving absolute or relative pressure values. Examples of TS.x-related parameters including absolute pressure values are such as $TS.MeanP_{min1}$, $TS.MeanP_{max}$, $TS.Mean_{SW}P$. Examples of TS. x-related parameters including relative pressure values are such as TS.MeandP, TS.MeanRT, TS.MeanDiff_dP and TS.MeanWavedP. In this context absolute pressure refers to pressure relative to atmospheric pressure. A challenge not solved by current and prior art technology is how to obtain useful diagnostic information from pressure measurements without a zero pressure level against atmospheric pressure. Computation of relationships between said TS.x-related parameters represents a technical solution to said challenge.

It is now focused on delta time sequence (ΔTS.x)-related parameters, with reference to FIG. 7a. First some remarks should be made concerning FIGS. 7a and 7b. In FIG. 7a is shown a continuous intracranial pressure (ICP) signal (Signal [1]) 701 derived from a sensor within the brain parenchyma (Location: Intra-dural), and in FIG. 7b is shown a continuous intracranial pressure (ICP) signal (Signal[2]) 702 derived from a sensor within the epidural space (Location: Epidural). Both these signals were derived from the same one recording Recording[62]; both signals were sampled simultaneously with identical time reference. The time (x-axis) 703 is identical both for Signal[1] 701 and Signal[2] 702. The pressure scale 704 of Signal[1] 701 (FIG. 7a) and the pressure scale 705 of Signal[2] 702 (FIG. 7b) had identical resolution though the absolute pressure levels were different. For both signals are shown two subsequent time sequence windows, termed Time Sequence[30] 706 (n−1) and Time Sequence [31] 707 (n).

For Signal[1] 701 the amplitudes (SW.dP) of the six included single pressure waves 708 within the first time sequence window (Time Sequence[30] 706) are numbered 709 (SW[1].dP), 710 (SW[2].dP), 711 (SW[3].dP), 712 (SW [4].dP), 713 (SW[5].dP), and 714 (SW[6].dP). For Signal[1] 701 the amplitudes (SW.dP) of the seven included single pressure waves 708 within the second time sequence window (Time Sequence[31] 707) are numbered 715 (SW[1].dP), 716 (SW[2].dP), 717 (SW[3].dP), 718 (SW[4].dP), 719 (SW[5]. dP), 720 (SW[6].dP) and 721 (SW[7].dP). For Signal[2] 702 the amplitudes (SW.dP) of the six included single pressure waves 708' within the first time sequence window (Time Sequence[30] 706) are numbered 722 (SW[1].dP), 723 (SW [2].dP), 724 (SW[3].dP), 725 (SW[4].dP), 726 (SW[5].dP), and 727 (SW[6].dP). For Signal[2] 702 the amplitudes (SW.dP) of the seven included single pressure waves 708' within the second time sequence window (Time Sequence [31] 707) are numbered 728 (SW[1].dP), 729 (SW[2].dP), 730 (SW[3].dP), 731 (SW[4].dP), 732 (SW[5].dP), 733 (SW [6].dP) and 734 (SW[7].dP).

As previously commented on FIGS. 4a and 4b, a subgroup of selected Time Sequence and Delta Time Sequence Criteria define whether single pressure waves 708, 708' which occur between two consecutive of said time sequence windows [Time Sequence[30] 706 (n−1) versus Time Sequence[31] 707 (n)] are to be placed within one or the other of said two consecutive individual time sequence windows (706, 707). Said selected criteria define that a first of said single pressure waves (SW[1] 715; FIG. 7a) 708 within said Time Sequence [31] 707 must have its ending diastolic minimum pressure value ($SW.P_{min2}$) within said Time Sequence[31] 707. Said selected criteria also define that a last of said single pressure waves (SW[7] 721; FIG. 7a) 708 within said Time Sequence [31] 707 must have both its starting diastolic minimum pressure value ($SW.P_{min1}$) and its ending diastolic minimum pressure value ($SW.P_{min2}$) within said Time Sequence[31] 707. These criteria are intended to illustrate the concept of the invention, not to limit the scope thereof, as other criteria may be used as well or as a replacement.

Reference is now given to FIG. 7a to illustrate the concept of computing delta time sequence (ΔTS.x)-related parameters between subsequent time sequences windows (n/n−1), said parameters are selected from the group of:

difference of mean values of starting diastolic minimum pressures between two subsequent time sequence windows ($\Delta TS.MeanP_{min1}$), as further detailed in equation (45):

$$\Delta TS[i].MeanP_{min1}=TS[i].MeanP_{min1}-TS[i-1].MeanP_{min1} \quad (45)$$

standard deviation of difference of mean values of starting diastolic minimum pressures of two subsequent time sequence windows ($\Delta TS.MeanP_{min1}\_STD$), as further detailed in equation (46):

$$\Delta TS[i].MeanP_{min1}\_STD=TS[i].MeanP_{min1}\_STD-TS[i-1].MeanP_{min1}\_STD \quad (46)$$

difference of mean values of systolic maximum pressure between two time sequence windows ($\Delta TS.MeanP_{max}$), as further detailed in equation (47):

$$\Delta TS[i].MeanP_{max}=TS[i].MeanP_{max}-TS[i-1].MeanP_{max} \quad (47)$$

standard deviation of difference of mean values of systolic maximum pressure between two subsequent time sequence windows ($\Delta TS.MeanP_{max}\_STD$), as further detailed in equation (48):

$$\Delta TS[i].MeanP_{max}\_STD=TS[i].MeanP_{max}\_STD-TS[i-1].MeanP_{max}\_STD \quad (48)$$

difference of mean amplitude values between two subsequent time sequence windows (ΔTS.MeandP), as further detailed in equation (49):

$$\Delta TS[i].MeandP=TS[i].MeandP-TS[i-1].MeandP \quad (49)$$

standard deviation of difference of mean amplitudes between two subsequent time sequence windows (ΔTS. MeandP_STD), as further detailed in equation (50):

$$\Delta TS[i].MeandP\_STD=TS[i].MeandP\_STD-TS[i-1].MeandP\_STD \quad (50)$$

difference of mean latency between two subsequent time sequence windows (ΔTS.MeandT), as further detailed in equation (51):

$$\Delta TS[i].MeandT=TS[i].MeandT-TS[i-1].MeandT \quad (51)$$

standard deviation of difference of mean latency between two subsequent time sequence windows (ΔTS.MeandT_ STD), as further detailed in equation (52):

$$\Delta TS[i].MeandT\_STD=TS[i].MeandT\_STD-TS[i-1].MeandT\_STD \quad (52)$$

difference of mean rise time coefficient between two subsequent time sequence windows (ΔTS.MeanRT), as further detailed in equation (53):

$$\Delta TS[i].MeanRT=TS[i].MeanRT-TS[i-1].MeanRT \quad (53)$$

standard deviation of difference of mean rise time coefficient between two subsequent time sequence windows (ΔTS.MeanRT_STD), as further detailed in equation (54):

$$\Delta TS[i].MeanRT\_STD=TS[i].MeanRT\_STD-TS[i-1].MeanRT\_STD \quad (54)$$

difference of mean wave duration between two subsequent time sequence windows (ΔTS.MeanWD), as further detailed in equation (55):

$$\Delta TS[i].\text{MeanWD} = TS[i].\text{MeanWD} - TS[i-1].\text{MeanWD} \quad (55)$$

standard deviation of difference of mean wave duration between two subsequent time sequence windows (ΔTS.MeanWD_STD), as further detailed in equation (56):

$$\Delta TS[i].\text{MeanWD\_STD} = TS[i].\text{MeanWD\_STD} - TS[i-1].\text{MeanWD\_STD} \quad (56)$$

difference of mean single wave pressure between two subsequent time sequence windows (ΔTS.Mean$_{SW}$P), as further detailed in equation (57):

$$\Delta TS[i].\text{Mean}_{SW}P = TS[i].\text{Mean}_{SW}P - TS[i-1].\text{Mean}_{SW}P \quad (57)$$

standard deviation of difference of mean single wave pressure of two subsequent time sequence windows (ΔTS.Mean$_{SW}$P_STD), as further detailed in equation (58):

$$\Delta TS[i].\text{Mean}_{SW}P\_STD = TS[i].\text{Mean}_{SW}P\_STD - TS[i-1].\text{Mean}_{SW}P\_STD \quad (58)$$

difference of mean diastolic minimum pressure difference between two subsequent time sequence windows (ΔTS.MeanDiff_P$_{min}$), as further detailed in equation (59):

$$\Delta TS[i].\text{MeanDiff\_P}_{min} = TS[i].\text{MeanDiff\_P}_{min} - TS[i-1].\text{MeanDiff\_P}_{min} \quad (59)$$

standard deviation of difference of mean diastolic minimum pressure difference between two subsequent sequence windows (ΔTS.MeanDiff_P$_{min}$_STD), as further detailed in equation (60):

$$\Delta TS[i].\text{MeanDiff\_P}_{min}\_STD = TS[i].\text{MeanDiff\_P}_{min}\_STD - TS[i-1].\text{MeanDiffP}_{min}\_STD \quad (60)$$

difference of mean systolic maximum pressure difference between two subsequent time sequence windows (ΔTS.MeanDiff_P$_{max}$), as further detailed in equation (61):

$$\Delta TS[i].\text{MeanDiff\_P}_{max} = TS[i].\text{MeanDiff\_P}_{max} - TS[i-1].\text{MeanDiff\_P}_{max} \quad (61)$$

standard deviation of difference of mean systolic maximum pressure difference between two subsequent time sequence windows (ΔTS.MeanDiff_P$_{max}$_STD), as further detailed in equation (62):

$$\Delta TS[i].\text{MeanDiffP}_{max}\_STD = TS[i].\text{MeanDiffP}_{max}\_STD - TS[i-1].\text{MeanDiffP}_{min}\_STD \quad (62)$$

difference of mean amplitude difference between two subsequent time sequence windows (ΔTS.MeanDiff_dP), as further detailed in equation (63):

$$\Delta TS[i].\text{MeanDiff\_dP} = TS[i].\text{MeanDiff\_dP} - TS[i-1].\text{MeanDiff\_dP} \quad (63)$$

standard deviation of difference of mean amplitude difference between two subsequent time sequence windows (ΔTS.MeanDiff_dP_STD), as further detailed in equation (64):

$$\Delta TS[i].\text{MeanDiffdP\_STD} = TS[i].\text{MeanDiffdP\_STD} - TS[i-1].\text{MeanDiffdP\_STD} \quad (64)$$

difference of mean latency difference between two subsequent time sequence windows (ΔTS.MeanDiff_dT), as further detailed in equation (65):

$$\Delta TS[i].\text{MeanDiff\_dT} = TS[i].\text{MeanDiff\_dT} - TS[i-1].\text{MeanDiff\_dT} \quad (65)$$

standard deviation of difference of mean latency difference between two subsequent time sequence windows (ΔTS.MeanDiff_dT_STD), as further detailed in equation (66):

$$\Delta TS[i].\text{MeanDiff\_dT\_STD} = TS[i].\text{MeanDiff\_dT\_STD} - TS[i-1].\text{MeanDiff\_dT\_STD} \quad (66)$$

difference of mean rise time coefficient difference between two subsequent time sequence windows (ΔTS.MeanDiff_RT), as further detailed in equation (67):

$$\Delta TS[i].\text{MeanDiff\_RT} = TS[i].\text{MeanDiff\_RT} - TS[i-1].\text{MeanDiff\_RT} \quad (67)$$

standard deviation of difference of mean rise time coefficient difference between two subsequent time sequence windows (ΔTS.MeanDiff_RT_STD), as further detailed in equation (68):

$$\Delta TS[i].\text{MeanDiff\_RT\_STD} = TS[i].\text{MeanDiff\_RT\_STD} - TS[i-1].\text{MeanDiff\_RT\_STD} \quad (68)$$

difference of mean wave duration difference between two subsequent time sequence windows (ΔTS.MeanDiff_WD), as further detailed in equation (69):

$$\Delta TS[i].\text{MeanDiff\_WD} = TS[i].\text{MeanDiff}_{WD} - TS[i-1].\text{MeanDiff}_{WD} \quad (69)$$

standard deviation of difference of mean wave duration difference between two subsequent time sequence windows (ΔTS.MeanDiff_WD_STD), as further detailed in equation (70):

$$\Delta TS[i].\text{MeanDiffWD\_STD} = TS[i].\text{MeanDiffWD\_STD} - TS[i-1].\text{MeanDiffWD\_STD} \quad (70)$$

difference of mean single wave pressure difference between two subsequent time sequence windows (ΔTS.MeanDiff_Mean$_{SW}$P), as further detailed in equation (71):

$$\Delta TS[i].\text{MeanDiff\_Mean}_{SW}P = TS[i].\text{MeanDiff\_Mean}_{SW}P - TS[i-1].\text{MeanDiff\_Mean}_{SW}P \quad (71)$$

standard deviation of difference of mean SW pressure difference between two subsequent time sequence windows (ΔTS.MeanDiff_Mean$_{SW}$P_STD), as further detailed in equation (72):

$$\Delta TS[i].\text{MeanDiff\_Mean}_{SW}P\_STD = TS[i].\text{MeanDiff\_Mean}_{SW}P\_STD - TS[i-1].\text{MeanDiff\_Mean}_{SW}P\_STD \quad (72)$$

difference of single wave count between two subsequent time sequence windows (ΔTS.SWCount), as further detailed in equation (73):

$$\Delta TS[i].\text{SWCount} = TS[i].\text{SWCount} - TS[i-1].\text{SWCount} \quad (73)$$

difference of mean wave amplitude between two subsequent time sequence windows (ΔTS.MeanWavedP), as further detailed in equation (74):

$$\Delta TS[i].\text{MeanWavedP} = TS[i].\text{MeanWavedP} - TS[i-1].\text{MeanWavedP} \quad (74)$$

difference of mean wave latency between two subsequent time sequence windows (ΔTS.MeanWavedT), as further detailed in equation (75):

$$\Delta TS[i].\text{MeanWavedT} = TS[i].\text{MeanWavedT} - TS[i-1].\text{MeanWavedT} \quad (75)$$

difference of mean wave rise time coefficient between two subsequent time sequence windows (ΔTS.MeanWaveRT), as further detailed in equation (76):

$$\Delta TS[i].\text{MeanWaveRT} = TS[i].\text{MeanWaveRT} - TS[i-1].\text{MeanWaveRT} \quad (76)$$

To further illustrate the concept it is shown the computation of difference of mean amplitude values between two subsequent time sequences (ΔTS.MeandP).

With reference to Signal[1] 701 the equation is as follows: ΔTS.MeandP=TS[31].MeandP−TS[30].MeandP. Again, TS[31].x refers to Time Sequence[31] 707 and TS[1].x refers to Time Sequence[30] 706. With reference to FIG. 7a, the equation for TS[30].MeandP within Time Sequence[30] 706 is as follows: TS[30].MeandP=(SW[1].dP+SW[2].dP+SW[3].dP+SW[4].dP+SW[5].dP+SW[6].dP)/6 (wherein SW[1].dP=709; SW[2].dP=710; SW[3].dP=711; SW[4].dP=712; SW[5].dP=713; SW[6].dP=714). With reference to FIG. 7a, the equation for TS[31].MeandP within Time Sequence[31] 707 is as follows: TS[31].MeandP=(SW[1].dP+SW[2].dP+SW[3].dP+SW[4].dP+SW[5].dP+SW[6].dP+SW[7].dP)/7 (wherein SW[1].dP=715; SW[2].dP=716; SW[3].dP=717; SW[4].dP=718; SW[5].dP=719; SW[6].dP=720; SW[7].dP=721).

Concerning the inventive step of computing said delta time sequence (ΔTS.x)-related parameters, the major significance relates to quality control of signal quality. The thresholds and ranges of said ΔTS.x parameters are different in the presence of good signal quality (i.e. single pressure waves are created by cardiac beat-induced pressure waves) as compared to bad signal quality (i.e. pressure waves are created by artifacts or a combination of artifacts or cardiac beat induced pressure waves). Said delta time sequence (ΔTS.x)-related parameters have a key role in excluding (i.e. not accepting) time sequence windows with said bad signal quality.

The strategy for best possible determination of single pressure waves created by cardiac beat-induced pressure waves, relates to the inventive step of determining criteria for the parameters (SW.x, ΔSW.x, TS.x, ΔTS.x) related to time sequence windows of said continuous pressure-related signal. So-called criteria related to said parameters relate to thresholds and ranges of said parameters. By this inventive step now commented on in the subsequent paragraphs, a tool is created for best possible identification of single pressure waves created by cardiac beat-induced pressure waves Reference is now given to said Determining Steps commented on for FIG. 2. With reference to the single wave (SW.x)-, delta single wave (ΔSW.x)-, time sequence (TS.x)- and delta time sequence (ΔTS.x)-related parameters, criteria are determined, referred to as Single Wave & Delta Single Wave Criteria and Time Sequence & Delta Time Sequence Criteria (see FIG. 2).

Single wave criteria relate to criteria for thresholds and ranges of said single pressure wave (SW.x)-related parameters of said single pressure waves during said time sequence windows, said parameters selected from the group of:
starting diastolic minimum pressure defining the start of the single pressure wave ($SW.P_{min1}$),
ending diastolic minimum pressure defining the end of the single pressure wave ($SW.P_{min2}$),
systolic maximum pressure of the single pressure wave ($SW.P_{max}$),
amplitude of the single pressure wave (SW.dP),
latency of the single pressure wave (SW.dT),
rise time coefficient of the single pressure wave (SW.RT),
wave duration of the single pressure wave (SW.WD),
mean single wave pressure of the single pressure wave ($SW.Mean_{SW}P$), and
diastolic minimum pressure difference of the single pressure wave ($SW.Diff\_P_{min}$).

In general, the notation related to criteria is: Criteria_Type_ Location_Parameter. Some examples of Single Wave Criteria are given, which are specifically related to continuous intracranial pressure (ICP) signals as indicated in the notation:
Criteria_ICP_Intra-dural_$SW.P_{max}$:
  a) Systolic maximum pressure of a single pressure wave must be between −5 to 100 mmHg for pair combinations of $SW.P_{min1}$ and $SW.P_{max}$ to be included for further analysis.
Criteria_ICP_Intra-dural_SW.dP:
  a) Amplitude (SW.dP) must be between 1.0 to 35.0 mmHg for pair combinations of $SW.P_{min1}$ and $SW.P_{max}$ to be included for further analysis.
Criteria_ICP_Intra-dural_SW.dT:
  a) Latency (SW.dT) must be between 0.10 to 0.40 seconds for pair combinations of $SW.P_{min1}$ and $SW.P_{max}$ to be included for further analysis.
Criteria_ICP_Intra-dural_SW.WD:
  a) Wave duration (SW.WD) must be between 0.30 to 1.5 seconds for pair combinations of $SW.P_{min1}$ and $SW.P_{max}$ to be included for further analysis.

These examples are not intended to limit the scope of the invention; but to illustrate the substance of said Single Wave Criteria. As indicated, the criteria are related to thresholds and ranges of said single pressure wave (SW.x)-related parameters during said time sequence windows. Said criteria determine inclusion, i.e. acceptance, or exclusion, i.e. rejection, of single pressure waves for further analysis; for example minimum-maximum pressure ($SW.P_{min1}/SW.P_{max}$) pairs with said single pressure wave (SW.x)-related parameters outside selectable thresholds and ranges are excluded (see FIG. 2).

Determining criteria for thresholds and ranges of delta single pressure wave (ΔSW.x)-related parameters between subsequent of said single pressure waves during said time sequence windows refers to Delta Single Wave Criteria, said criteria are derived from the group of ΔSW.x-related parameters of:
systolic maximum pressure difference between two subsequent single pressure waves ($ΔSW.Diff\_P_{max}$),
amplitude difference between two subsequent single pressure waves (ΔSW.Diff_dP),
latency difference between two subsequent single pressure waves (SW.Diff_dT),
rise time coefficient difference between two subsequent single pressure waves (ΔSW.Diff_RT),
wave duration difference between two subsequent single pressure waves (ΔSW.Diff_WD), and
mean single wave pressure difference between two subsequent single pressure waves ($ΔSW.Diff\_Mean_{SW}P$).

Some examples of Delta Single Wave Criteria are given, which are specifically related to continuous intracranial pressure (ICP) signals as indicated in the notation:
Criteria_ICP_Intra-dural_$ΔSW.P_{max}$:
  a) Systolic maximum pressure difference between two subsequent single pressure waves must be ≤10 mmHg for combinations of $SW.P_{min1}$ and $SW.P_{max}$ to be included for further analysis.
Criteria_ICP_Intra-dural_ΔSW.WD:
  a) Wave duration difference between two subsequent single pressure waves must be ≤0.10 seconds for pair combinations of $SW.P_{min1}$ and $SW.P_{max}$ to be included for further analysis.

These examples are not intended to limit the scope of the invention; but to illustrate the substance of said Delta Single Wave Criteria. Said criteria for thresholds and ranges of said delta single pressure wave (ΔSW.x)-related parameters between subsequent of said single pressure waves during said time sequence windows determines inclusion or exclusion of said single pressure waves for further analysis. Said criteria exclude minimum-maximum pressure ($SW.P_{min1}/SW.P_{max}$) pairs with said delta single pressure wave (ΔSW.x)-related parameters outside selectable thresholds and ranges.

Determining criteria for thresholds and ranges of time sequence (TS.x)-related parameters of said single pressure waves during said time sequence windows refers to Time Sequence Criteria; said criteria are derived from the group of TS.x-related parameters of:
   mean value of starting diastolic minimum pressures of a time sequence window (TS.MeanP$_{min1}$),
   standard deviation of mean value of starting diastolic minimum pressures of a time sequence window (TS.MeanP$_{min1}$_STD),
   mean value of systolic maximum pressures of a time sequence window (TS.MeanP$_{max}$),
   standard deviation of mean value of systolic maximum pressures of a time sequence window (TS.MeanP$_{max}$_STD),
   mean amplitude of a time sequence window (TS.MeandP),
   standard deviation of mean amplitude of a time sequence window (TS.MeandP_STD),
   mean latency of a time sequence window (TS.MeandT),
   standard deviation of mean latency of a time sequence window (TS.MeandT_STD),
   mean rise time coefficient of a time sequence window (TS.MeanRT),
   standard deviation of mean rise time coefficient of a time sequence window (TS.MeanRT_STD),
   mean wave duration of a time sequence window (TS.MeanWD),
   standard deviation of mean wave duration of a time sequence window (TS.MeanWD_STD),
   mean single wave pressure of a time sequence window (TS.Mean$_{SW}$P),
   standard deviation of mean single wave pressure of a time sequence window (TS.Mean$_{SW}$P_STD),
   mean of diastolic minimum pressure differences of a time sequence window (TS.MeanDiff_P$_{min}$),
   standard deviation of mean of diastolic minimum pressure differences of a time sequence window (TS.MeanDiff_P$_{min}$_STD),
   mean of systolic maximum pressure differences of a time sequence window (TS.MeanDiff_P$_{max}$),
   standard deviation of mean of systolic maximum pressure differences of a time sequence window (TS.MeanDiff_P$_{max}$_STD),
   mean amplitude difference of a time sequence window (TS.MeanDiff_dP),
   standard deviation of mean amplitude difference of a time sequence window (TS.MeanDiff_dP_STD),
   mean latency difference of a time sequence window (TS.MeanDiff_dT),
   standard deviation of mean latency difference of a time sequence window (TS.MeanDiff_dT_STD),
   mean rise time coefficient difference of a time sequence window (TS.MeanDiff_RT),
   standard deviation of mean rise time coefficient difference of a time sequence window (TS.MeanDiff_RT_STD),
   mean wave duration difference of a time sequence window (TS.MeanDiff_WD),
   standard deviation of mean wave duration difference of a time sequence window (TS.MeanDiff_WD_STD),
   mean single wave pressure difference of a time sequence window (TS.MeanDiff_Mean$_{SW}$P),
   standard deviation of mean single wave pressure difference of a time sequence window (TS.MeanDiff_Mean$_{SW}$P_STD),
   numbers of included single pressure waves of a time sequence window (TS.SWCount),
   mean wave amplitude of a time sequence window (TS.MeanWavedP),
   mean wave latency of a time sequence window (TS.MeanWavedT), and
   mean wave rise time coefficient of a time sequence window (TS.MeanWaveRT).

Some examples of Time Sequence Criteria are given, which are specifically related to continuous intracranial pressure (ICP) signals as indicated in the notation:
   Criteria_ICP_Intra-dural_TS.SWCount:
      a) Number of included single pressure waves of a time sequence window must be between 4 and 18 for said time sequence window to be included (accepted) for further analysis.
   Criteria_ICP_Intra-dural_TS.MeanP$_{max}$:
      a) Mean value of systolic maximum pressures of a time sequence window must be between 2 and 100 mmHg for said time sequence window to be included for further analysis.

The intention of these examples of Time Sequence Criteria are to illustrate the substance of said criteria, though the specific values are not intended to limit the scope of the invention. Time Sequence Criteria for thresholds and ranges of time sequence (TS.x)-related parameters of single pressure waves during time sequence windows determines inclusion, i.e. acceptance, or exclusion, i.e. rejection, of said time sequences for further analysis. The criteria exclude for further analysis time sequences with time sequence (TS.x)-related parameters outside selectable thresholds and ranges.

Determining criteria for thresholds and ranges of delta time sequence ($\Delta$TS.x)-related parameters between subsequent time sequences refers to Delta Time Sequence Criteria; said criteria are derived from the group of $\Delta$TS.x-related parameters of:
   difference of mean values of starting diastolic minimum pressures between two subsequent time sequence windows ($\Delta$TS.MeanP$_{min1}$),
   standard deviation of difference of mean values of starting diastolic minimum pressures of two subsequent time sequence windows ($\Delta$TS.MeanP$_{min1}$_STD),
   difference of mean values of systolic maximum pressure between two subsequent time sequence windows ($\Delta$TS.MeanP$_{max}$),
   standard deviation of difference of mean values of systolic maximum pressure between two subsequent time sequence windows ($\Delta$TS.MeanP$_{max}$_STD),
   difference of mean amplitude values between two subsequent time sequence windows ($\Delta$TS.MeandP),
   standard deviation of difference of mean amplitudes between two subsequent time sequence windows ($\Delta$TS.MeandP_STD),
   difference of mean latency between two subsequent time sequence windows ($\Delta$TS.MeandT),
   standard deviation of difference of mean latency between two subsequent time sequence windows ($\Delta$TS.MeandT_STD),
   difference of mean rise time coefficient between two subsequent time sequence windows ($\Delta$TS.MeanRT),
   standard deviation of difference of mean rise time coefficient between two subsequent time sequence windows ($\Delta$TS.MeanRT_STD),
   difference of mean wave duration between two subsequent time sequence windows ($\Delta$TS.MeanWD),
   standard deviation of difference of mean wave duration between two subsequent time sequence windows ($\Delta$TS.MeanWD_STD), difference of mean single wave pressure between two subsequent time sequence windows (ΔTS.Mean$_{SW}$P), standard deviation of difference of mean single wave pressure of two subsequent time sequence windows (ΔTS.Mean$_{SW}$P_STD), difference of mean diastolic minimum pressure difference between two subsequent time sequence windows (ΔTS.MeanDiff_P$_{min}$), standard deviation of difference of mean diastolic minimum pressure difference between two subsequent time sequence windows (ΔTS.MeanDiff_P$_{min}$_STD), difference of mean systolic maximum pressure difference between two subsequent time sequence windows (ΔTS.MeanDiff_P$_{max}$), standard deviation of difference of mean systolic maximum pressure difference between two subsequent time sequence windows (ΔTS.MeanDiff_P$_{max}$_STD), difference of mean amplitude difference between two subsequent time sequence windows (ΔTS.MeanDiff_dP), standard deviation of difference of mean amplitude difference between two subsequent time sequence windows (ΔTS.MeanDiff_dP_STD), difference of mean latency difference between two subsequent time sequence windows (ΔTS.MeanDiff_dT), standard deviation of difference of mean latency difference between two subsequent time sequence windows (ΔTS.MeanDiff_dT_STD), difference of mean rise time coefficient difference between two subsequent time sequence windows (ΔTS.MeanDiff_RT), standard deviation of difference of mean rise time coefficient difference between two subsequent time sequence windows (ΔTS.MeanDiff_RT_STD), difference of mean wave duration difference between two subsequent time sequence windows (ΔTS.MeanDiff_WD), standard deviation of difference of mean wave duration difference between two subsequent time sequence windows (ΔTS.MeanDiff_WD_STD), difference of mean single wave pressure difference between two subsequent time sequence windows (ΔTS.MeanDiff_Mean$_{SW}$P), standard deviation of difference of mean SW pressure difference between two subsequent time sequence windows (ΔTS.MeanDiff_Mean$_{SW}$P_STD), difference of single wave count between two subsequent time sequence windows (ΔTS.SWCount), difference of mean wave amplitude between two subsequent time sequence windows (ΔTS.MeanWavedP), difference of mean wave latency between two subsequent time sequence windows (ΔTS.MeanWavedT), and difference of mean wave rise time coefficient between two subsequent time sequence windows (ΔTS.MeanWaveRT).

Some examples of Delta Time Sequence Criteria are given, which are specifically related to continuous intracranial pressure (ICP) signals as indicated in the notation:

Criteria_ICP_Intra-dural_ΔTS.SWCount:
  a) Difference of single wave count between two subsequent time sequences must be ≤2 for said time sequence window to be included for further analysis.

Criteria_ICP_Intra-dural_ΔTS.MeanDiff_dP:
  a) Difference of mean amplitude between two subsequent time sequences must be ≤5 mmHg for said time sequence window to be included for further analysis.

The intention of these examples of Delta Time Sequence Criteria are to illustrate the substance of said criteria, though the specific values are not intended to limit the scope of the invention. Delta Time Sequence Criteria for thresholds and ranges of time sequence (ΔTS.x)-related parameters between subsequent time sequence windows determine inclusion or exclusion of said time sequences for further analysis. The criteria exclude time sequence windows with said delta time sequence (ΔTS.x)-related parameters outside selectable thresholds and ranges.

It is differentiated between static and dynamic criteria. Static criteria for thresholds and ranges of said SW.x-, ΔSW.x-, TS.x- and ΔTS.x-related parameters are unchangeable during a recording. Dynamic criteria for said thresholds and ranges of said SW.x-, ΔSW.x-, TS.x- and ΔTS.x-related parameters are changeable during a recording.

The major application of determination of Single Wave & Delta Single Wave Criteria and Time Sequence & Delta Time Sequence Criteria are optimal identification of single pressure waves related to cardiac beat-induced pressure waves and identification of pressure waves related to artifacts or a combination of artifacts and cardiac beat-induced pressure waves. This represents an optimal differentiating between single pressure waves caused by cardiac beat-induced pressure waves and pressure waves caused by artifact-induced pressure waves or a combination thereof.

The determination of Single Wave & Delta Single Wave Criteria and Time Sequence & Delta Time Sequence Criteria should be considered an iterative process. This is explained with reference to the experience of the inventor. When analyzing continuous intracranial pressure (ICP) signals during the first years, the inventor used only the following criteria (i.e. Single Wave Criteria and Time Sequence Criteria):

Criteria_ICP_Intra-dural_SW.dP:
  a) Amplitude (SW.dP) must be between 1.0 to 35.0 mmHg for pair combinations of SW.P$_{min1}$ and SW.P$_{max}$ to be included for further analysis.

Criteria_ICP_Intra-dural SW.dT:
  a) Latency (SW.dT) must be between 0.10 to 0.40 seconds for pair combinations of SW.P$_{min1}$ and SW.P$_{max}$ to be included for further analysis.

Criteria_ICP_Intra-dural TS.SWCount:
  a) Number of included single pressure waves of a time sequence window must be between 4 and 18 for said time sequence window to be included for further analysis.

Thus, with reference to the Identifying Steps shown in FIG. 2., included single pressure waves were identified by SW.P$_{max}$/SW.P$_{min1}$ pair combinations wherein the calculated amplitude (SW.dP) values were between 1.0 and 35.0 mmHg, and the calculated latency (SW.dT) values were between 0.10 and 0.40 seconds. Furthermore, the included time sequence windows contained between 4 and 18 included single pressure waves. Several hundreds of continuous intracranial pressure (ICP) recordings were obtained and stored in the database as raw data files by this approach. For each of these continuous intracranial pressure (ICP) recordings, the different SW.x-, ΔSW.x-, TS.x- and ΔTS.x-related parameters were computed. The method of computing said parameters is applied to each of said time sequence windows in a continuous series of said time sequence windows during a recording. By this approach a reference material is established concerning the normal distribution of said SW.x-, ΔSW.x-, TS.x- and ΔTS.x-related parameters. Based on this normal distribution, new and improved criteria are determined for thresholds and ranges of said SW.x-, ΔSW.x-, TS.x- and ΔTS.x-related parameters during said time sequence windows (or more correctly between said time sequence windows for ΔTS.x-related parameters). The new thresholds and ranges of said Single Wave & Delta Single Wave Criteria and Time Sequence & Delta Time Sequence Criteria are applied when analyzing new continuous intracranial pressure (ICP) signals. In addition, the raw data files of continuous intracranial pressure (ICP) signals stored in said database may be run through the Identifying Steps and Computing Steps shown in FIG. 2 once again, and both manual and automatic verification of the output being performed.

The Identifying Steps, Computing Steps and Determining Steps described in FIG. 2 provide a new and inventive method for processing continuous pressure-related signals derived from locations inside or outside a human or animal body or body cavity. Said inventive method (referred to as a first feature of this invention) has great significance as shortly summarized below:

Time sequence (TS.x)-related parameters can be computed from included time sequence windows wherein said time sequence windows are included the best possible way. Said time sequence windows contain single pressures waves related to cardiac beat-induced pressure waves, with less impact of pressure waves caused by artifacts or a combination of artifacts and cardiac beat-induced pressure waves. Thereby the risk of computing false or misleading time sequence (TS.x)-related parameters is made minimal.

Related time sequence (rTS.x) parameters can be determined from included time sequence windows wherein said time sequence windows are included the best possible way. Time sequence windows from simultaneous signals within a recording contain single pressure waves related to cardiac beat-induced pressure waves, with less impact of pressure waves created by artifacts or a combination of artifacts and cardiac beat-induced pressure waves. Obviously, it has no meaning to compute related time sequence (rTS.x) parameters from time sequence windows containing a high proportion of artifacts. This aspect is crucial for the inventive method further detailed in independent claim 1 and subsequent sub-claims 2-25.

According to the present invention there is provided for a device and a system, which enable inter alia more controlled drainage of excess fluid from a brain or spinal fluid cavity to another body cavity of a human being or animal. However, there are also aspects linked to the use of said device and system. As appreciated, said device and system include components making use of one or more of the inventive methods according to the invention to yield intended output from the device or system. A key element concerning these features of the invention is the computation of time sequence (TS.x)-related parameters. Obviously, it is crucial that time sequence (TS.x)-related parameters are computed from time sequence windows that are included the best possible way (i.e. time sequence windows containing single pressures waves related to cardiac beat-induced pressure waves, not to artifacts or a combination of artifacts and cardiac beat-induced pressure waves). Computation of false or misleading time sequence (TS.x)-related parameters would cause wrong regulation of drainage of fluid from said brain or spinal fluid cavity.

The method of computing time sequence (TS.x)-related parameters has a key role in other described devices and system according to this invention. The invention describes a display device(s), a sensor device (s) and combined sensor-display device(s) for use in sensing continuous pressure-related signals derivable from locations inside or outside a human or animal body or body cavity. The invention also describes a system for processing continuous pressure-related signals derivable from one or more sensor(s) having location(s) inside or outside a body or body cavity of a human being. As related to these features of the invention, it is crucial that time sequence (TS.x)-related parameters are computed from time sequence windows that are included the best possible way (i.e. time sequence windows containing single pressures waves related to cardiac beat-induced pressure waves, not to artifacts or a combination of artifacts and cardiac beat-induced pressure waves). Computation of false or misleading time sequence (TS.x)-related parameters would cause wrong measurements from said sensor device(s) and display wrong information from said display device (s) or combined sensor-display device(s).

Figure 7:
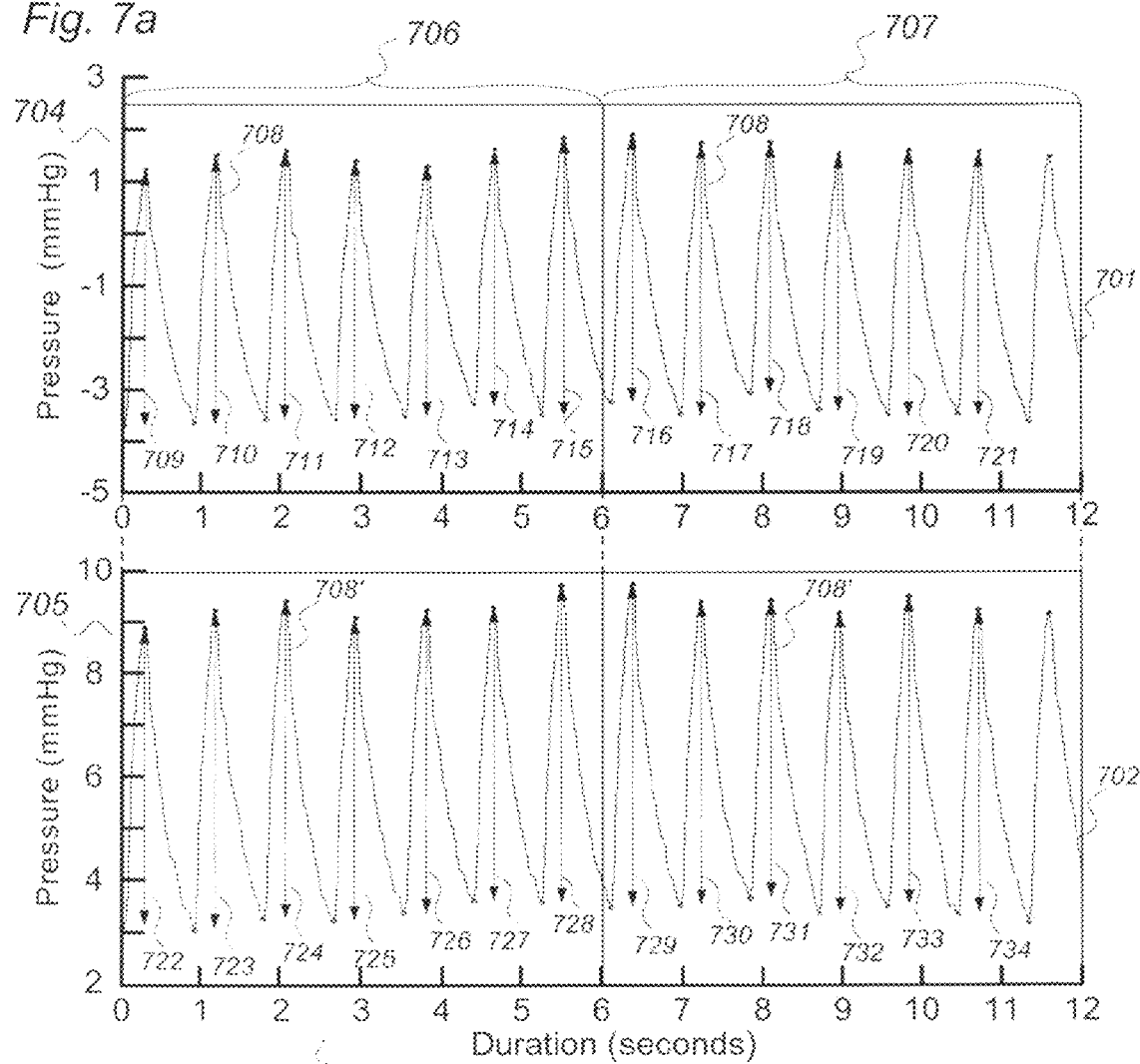
FIG. 7a shows two subsequent time sequence windows of a continuous pressure signal derived from a sensor within the brain parenchyma (Signal [1])
FIG. 7b shows two subsequent time sequence windows of a continuous pressure signal derived from a sensor within the intracranial epidural space (Signal[2]).
Figure 8:
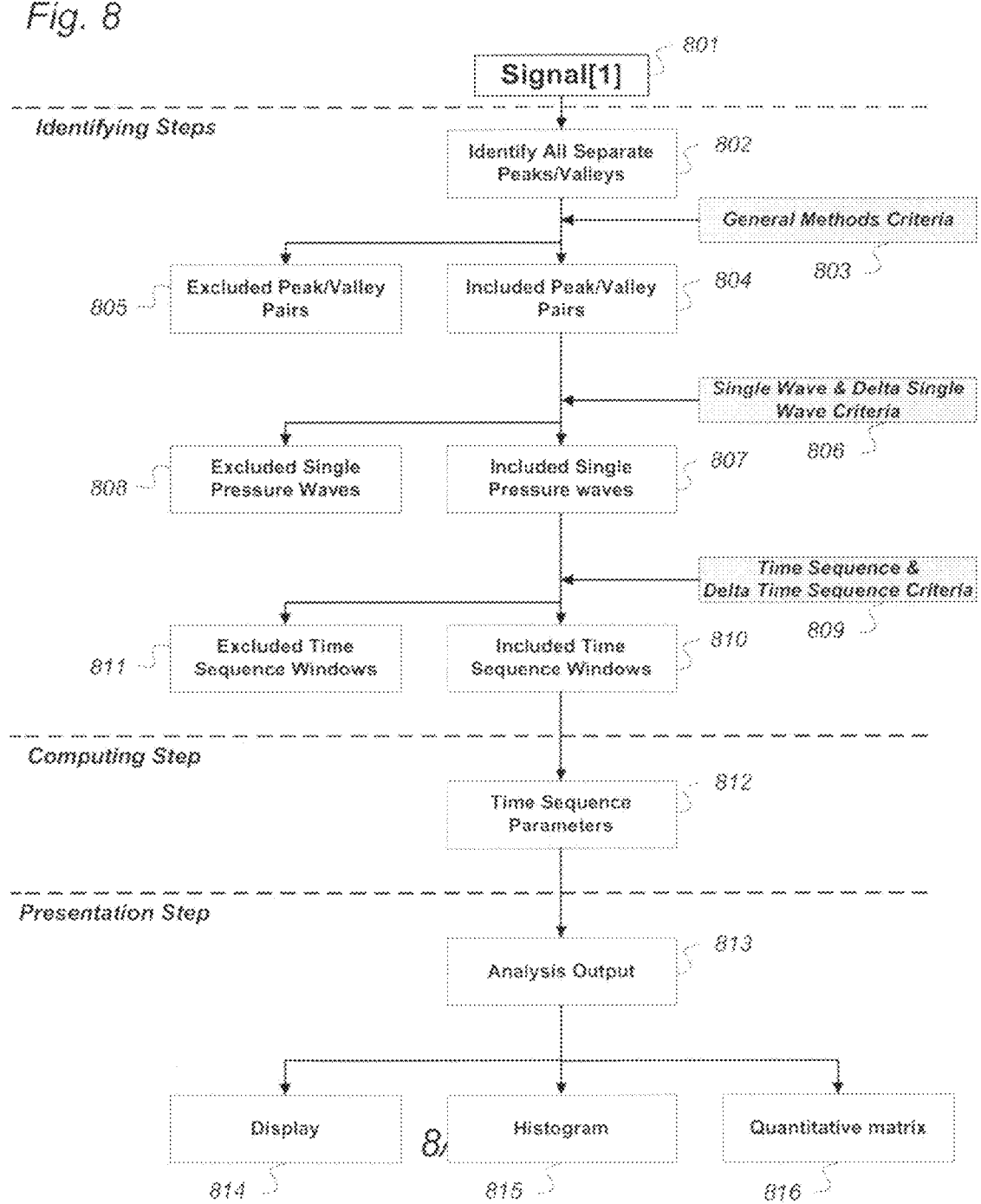
FIG. 8 shows a flow chart over a method for processing continuous pressure-related signals including determination of time sequence (TS.x)-related parameters.

Reference is now given to the second feature of this invention. In particular, characteristics of said second feature are illustrated in FIG. 8, and also in FIGS. 4 and 7.

Said second feature of the invention is related to a method for processing continuous pressure-related signals derivable from locations inside or outside a human or animal body or body cavity, comprising the steps of obtaining samples of said signals at specific intervals, and converting thus sampled pressure signals into pressure-related digital data with a time reference. For selectable time sequence windows the method comprises the further steps of identifying from said digital data signal single pressure waves related to cardiac beat-induced pressure waves, and identifying from said digital data signal pressure waves related to artifacts or a combination of artifacts and cardiac beat-induced pressure waves. The method also relates to computing time sequence (TS.x)-related parameters of said single pressure waves during individual of said time sequence windows, and establishing an analysis output selected from one or more of said time sequence (TS.x)-related parameters of said single pressure waves during individual of said time sequence windows, said one or more parameters selectable from: Mean wave amplitude (TS.MeanWavedP), mean wave latency (TS.MeanWavedT), mean wave rise time coefficient (TS.MeanWaveRT), mean amplitude (TS.MeandP), mean latency (TS.MeandT), mean rise time coefficient (TS.MeanRT), and mean single wave pressure (TS.Mean$_{SW}$P).

Test recordings have shown that said time sequence (TS.x)-related parameters provide completely new information from continuous pressure-related signals, not revealed by current and prior art technology. Said new information is shortly summarized:

Time sequence (TS.x)-related parameters (e.g. such as TS.MeanWavedP, TS.MeanWavedT, TS.MeanWaveRT, TS.MeandP, TS.MeandT, TS.MeanRT, TS.Mean$_{SW}$P) provide completely new information whether pressures are abnormally high or not. For example, reduced cerebral compliance, i.e. abnormally high intracranial pressure (ICP), is not revealed by known technology, but is revealed by said TS.x parameters.

Time sequence (TS.x)-related parameters (e.g. such as TS.MeanWavedP, TS.MeanWavedT, TS.MeanWaveRT, TS.MeandP, TS.MeandT, TS.MeanRT, TS.Mean$_{SW}$P) provide completely new information whether a pressure measurement is of good or bad quality. For example, sensor error or wrong sensor placement may not always be detected by known technology, but are revealed by said TS.x parameters.

Time sequence (TS.x)-related parameters (e.g. such as TS.MeanWavedP, TS.MeanWavedT, TS.MeanWaveRT, TS.MeandP, TS.MeandT, TS.MeanRT, TS.Mean$_{SW}$P) provide completely new information whether pressures are changing during treatment (surgical or medical). A change in pressure may be impossible to reveal according to known and prior art technology. For example, a change in intracranial pressure (ICP) following medical or surgical treatment may be impossible to reveal by current technology, though pressure changes are shown by said TS.x parameters.

Time sequence (TS.x)-related parameters (e.g. such as TS.MeanWavedP, TS.MeanWavedT, TS.MeanWaveRT, TS.MeandP, TS.MeandT, TS.MeanRT) involving relative values are not influenced by a zero pressure level relative to atmospheric pressure or drift of sensor zero pressure level. This fact represents a technical solution as compared to current technology, in which such problems are important concerning calibration against a zero pressure level or drift of sensor pressure level.

An overview of said method for analyzing continuous pressure-related signals 801 derived from within or outside a human or animal body or body cavity is given in FIG. 8, and reference is now given to FIG. 8.

In short, the method incorporates different Identifying Steps, Computing Step and Presentation Step. Said Identifying Steps include identification of all separate peaks and valleys 802 in said sampled signal 801. Each of said peaks is a sample with a pressure value and a time stamp or location, and each of said valleys is a sample with a pressure value and a time stamp or location. The result of applying General Methods Criteria 803 is either included, i.e. accepted, peak/valley pair combinations 804 or excluded, i.e. reject, peak/valley pair combinations 805.

After applying the Single Wave & Delta Single Wave Criteria 806 to said included peak/valley pairs 804, the output is either included single pressure waves 807 or excluded pressure waves 808. Said criteria 806 relate to thresholds and ranges of single pressure wave (SW.x)-related parameters and delta single pressure wave (ΔSW.x)-related parameters during time sequence windows.

After applying the Single Wave & Delta Single Wave Criteria 806, included pair combinations of peak/valley pairs 804 in said signal 801 correspond to included single pressure waves 807. Pair combinations of diastolic minimum pressure (SW.P$_{min1}$) and systolic maximum pressure (SW.P$_{max}$) characterize single pressure waves created by cardiac beat-induced pressure waves. Said criteria 806 exclude for further analysis pressure waves (i.e. minimum-maximum pressure (SW.P$_{min1}$/SW.P$_{max}$) pairs) during said time sequence windows with said single pressure wave (SW.x)- and delta single pressure wave (ΔSW.x)-related parameters outside selected criteria for thresholds and ranges of said parameters. Said criteria 806 include for further analysis single pressure waves 807 having single pressure wave (SW.x)- and delta single pressure wave (ΔSW.x)-related parameters within selected criteria for thresholds and ranges of said single pressure wave (SW.x)-related parameters. Pair combinations of diastolic minimum pressure (SW.P$_{min1}$) and systolic maximum pressure (SW.P$_{max}$) correspond to diastolic minimum pressures and systolic maximum pressures of individual of pressure waves created by each of said cardiac beats.

In order to further evaluate the included single pressure waves 807, Time Sequence & Delta Time Sequence Criteria 809 are applied to each of said time sequence windows in a continuous series of said time sequence windows during a recording. Each time sequence window is a selected time frame of said signal. Said criteria 809 for thresholds and ranges of said time sequence (TS.x) and delta time sequence (ΔTS.x)-related parameters determine included time sequence windows 810 and excluded time sequence windows 811. Said criteria 809 exclude for further analysis time sequence windows 811 with time sequence (TS.x)- and delta time sequence (ΔTS.x)-related parameters outside selected criteria for thresholds and ranges of said parameters. Said criteria 809 include for further analysis time sequence windows 810 having time sequence (TS.x) and delta time sequence (ΔTS.x)-related parameters within selected criteria for thresholds and ranges of said time sequence (TS.x) and delta time sequence (ΔTS.x)-related parameters.

In a next Computing Step is computed time sequence (TS.x)-related parameters 812 for each individual of said included time sequence windows 810. The Identifying Steps are applied to each of said time sequence windows in a continuous series of said time sequence windows during a recording. The Computing Step is applied to each of said included time sequence windows 810 in a continuous series of said time sequence windows during a recording. In a final Presentation Step, an analysis output is established selected from one or more of said time sequence (TS.x)-related parameters: Mean wave amplitude (TS.MeanWavedP), mean wave latency (TS.MeanWavedT), mean wave rise time coefficient (TS.MeanWaveRT), mean amplitude (TS.MeandP), mean latency (TS.MeandT), mean rise time coefficient (TS.MeanRT), and mean single wave pressure (TS.Mean$_{SW}$P). Said analysis output for selected ones of said time sequence (TS.x)-related parameters includes different types of data presentation, such as repetitive numerical presentation, trend plot presentation, histogram presentation, and quantitative matrix presentation.

Concerning the Identifying Steps, the process method is identical as the process described for FIGS. 2, 3*a*, 3*b*, 3*c*, 4*a*, 4*b*, 5*a*, 5*b*, 6, and 7*a*. Details about General Methods Criteria 803, Single Wave & Delta Wave Criteria 806 and Time Sequence & Delta Time Sequence Criteria 809 are already commented on in detail with reference to FIG. 2, and therefore these aspects are not commented on further in this context.

The output of the Identifying Steps is included, i.e. accepted, time sequence windows wherein said time sequence windows 810 are included the best possible way. This means that these time sequence windows 810 contain single pressure waves related to cardiac beat-induced pressure waves, not to artifacts or a combination of artifacts and cardiac beat-induced pressure waves. Thereby the risk of computing false or misleading time sequence (TS.x)-related parameters is made minimal.

In the Computing Step, time sequence (TS.x)-related parameters 812 from included time sequences windows 810 are computed, said parameters selected from the group of:

mean value of starting diastolic minimum pressures of a time sequence window (TS.MeanP$_{min1}$), standard deviation of mean value of starting diastolic minimum pressures of a time sequence window (TS.MeanP$_{min1}$_STD), mean value of systolic maximum pressures of a time sequence window (TS.MeanP$_{max}$), standard deviation of mean value of systolic maximum pressures of a time sequence window (TS.MeanP$_{max\_}$STD), mean amplitude of a time sequence window (TS.MeandP), standard deviation of mean amplitude of a time sequence window (TS.MeandP_STD), mean latency of a time sequence window (TS.MeandT), standard deviation of mean latency of a time sequence window (TS.MeandT_STD), mean rise time coefficient of a time sequence window (TS.MeanRT), standard deviation of mean rise time coefficient of a time sequence window (TS.MeanRT_STD), mean wave duration of a time sequence window (TS.MeanWD), standard deviation of mean wave duration of a time sequence window (TS.MeanWD_STD), mean single wave pressure of a time sequence window (TS.Mean$_{SW}$P), standard deviation of mean single wave pressure of a time sequence window (TS.Mean$_{SW}$P_STD), mean of diastolic minimum pressure differences of a time sequence window (TS.MeanDiff_P$_{min}$), standard deviation of mean of diastolic minimum pressure differences of a time sequence window (TS.MeanDiff_P$_{min}$_STD), mean of systolic maximum pressure differences of a time sequence window (TS.MeanDiff_P$_{max}$), standard deviation of mean of systolic maximum pressure differences of a time sequence window (TS.MeanDiff_P$_{max}$_STD), mean amplitude difference of a time sequence window (TS.MeanDiff_dP), standard deviation of mean amplitude difference of a time sequence window (TS.MeanDiff_dP_STD), mean latency difference of a time sequence window (TS.MeanDiff_dT), standard deviation of mean latency difference of a time sequence window (TS.MeanDiff_dT_STD), mean rise time coefficient difference of a time sequence window (TS.MeanDiff_RT), standard deviation of mean rise time coefficient difference of a time sequence window (TS.MeanDiff_RT_STD), mean wave duration difference of a time sequence window (TS.MeanDiff_WD), standard deviation of mean wave duration difference of a time sequence window (TS.MeanDiff_WD_STD), mean single wave pressure difference of a time sequence window (TS.MeanDiff_Mean$_{SW}$P), standard deviation of mean single wave pressure difference of a time sequence window (TS.MeanDiff_Mean$_{SW}$P_STD), numbers of accepted single pressure waves of a time sequence window (TS.SWCount), mean wave amplitude of a time sequence window computed according to the first matrix (TS.MeanWavedP), mean wave latency of a time sequence window computed according to the first matrix (TS.MeanWavedT), mean wave rise time coefficient of a time sequence window computed according to the second matrix (TS.MeanWaveRT).

In particular, an analysis output is established selected from one or more of said time sequence (TS.x)-related parameters 812: Mean wave amplitude (TS.MeanWavedP), mean wave latency (TS.MeanWavedT), mean wave rise time coefficient (TS.MeanWaveRT), mean amplitude (TS.MeandP), mean latency (TS.MeandT), mean rise time coefficient (TS.MeanRT), and mean single wave pressure (TS.Mean$_{SW}$P). The computation of these time sequence (TS.x)-related parameters is now commented on.

The computation of mean wave amplitude (TS.MeanWavedP) and mean wave latency (TS.MeanWavedT) is now described. This analysis comprises the steps of creating a first matrix (Table 1) based on determining numbers of single pressure waves with pre-selected values related to amplitude (SW.dP) and latency (SW.dT), one axis of the matrix being related to an array of pre-selected values of pressure amplitude (SW.dP) and the other axis of the matrix being related to an array of pre-selected values of latencies (SW.dT), and indicating for each matrix cell at respective intersections in said first matrix a number of occurrence of matches between a specific pressure amplitude (SW.dP) and a specific latency (SW.dT) related to successive measurements of single pressure waves over said individual time sequence windows. The occurrence of matches in said matrix is indicated through actual number of matches during individual of said time sequence windows. The single pressure wave parameters of amplitude (SW.dP) and latency (SW.dT) are categorized into groups, said groups reflecting ranges of said single wave (SW.x)-related parameter values. The method comprises the further step of computing balanced position for a number of occurrences of said single pressure wave (SW.x)-related parameters amplitude (SW.dP) and latency (SW.dT) values during individual of said time sequence windows in said first matrix. The balanced position of said first matrix of numbers of amplitude (SW.dP) and latency (SW.dT) combinations corresponds to mean wave amplitude (TS.MeanWavedP) and mean wave latency (TS.MeanWavedT) during said individual time sequence windows.

A detailed example of computing the mean wave amplitude (TS.MeanWavedP) and mean wave latency (TS.MeanWavedT) is now given with reference to FIG. 4b. The mathematical process is intended to illustrate the concept, not to limit the scope of the invention. The process of determining the included single pressure waves 408 within the time sequence window 405 was described in connection with FIGS. 4a and 4b. The included, i.e. accepted, single pressure waves 408 (identified by included SW.P$_{max}$ 410/SW.P$_{min1}$ 411 pairs) during the time sequence window shown 405 shown in FIG. 4b (Time Sequence[360]) are termed SW[1], SW[2], SW[3], SW[4], and SW[5]. For each of these single pressure waves 408 both the amplitude (SW.dP) and latency (SW.dT) values were computed. The number of occurrences of single pressure waves 408 with certain amplitude (SW.dP) and latency (SW.dT) combinations are plotted into a first matrix that is two-dimensional. A part of such a matrix is presented in Table 1, illustrating the distribution of amplitude (SW.dP)/latency (SW.dT) combinations of the five included single pressure waves 408 (SW[1], SW[2], SW[3], SW[4], and SW[5]) presented in FIG. 4b. For example, single pressure waves 408 with amplitude (SW.dP) values greater or equal to 2.5 mmHg but less than 3.0 mmHg and latency (SW.dT) values greater or equal to 0.10 seconds, but less than 0.11 seconds occurred once during the time sequence window 405 of 6 seconds shown in said first matrix (Time Sequence [360]). The amplitude (SW.dP) values are presented in the columns and the latency (SW.dT) values in the rows. The matrix shown in Table 1 represents only a small fraction of a matrix of 1800 cells. A total of 60 amplitude (SW.dP) groups were created using a range of amplitudes (SW.dP) equal to 0 to 30.0 mmHg, with intervals of 0.5 mmHg, giving a total of 60 columns. A total of 30 latency (SW.dT) groups were created using a range of latencies (SW.dT) from 0.10 to 0.40 seconds with intervals 0.01 seconds, giving a total of 30 rows. For example, the first column corresponds to the first amplitude (SW.dP) group, named 0.5 (corresponding to 0.5 mmHg); this group includes amplitude (SW.dP) values greater or equal to 0.5 mmHg, but less than 1.0 mmHg (indicated by the group range 0.5≤SW.dP<1). The midpoint (or mean) of the group is 0.75 [(0.5+1.0)/2]. Since the observation is categorized or grouped, the midpoint of the group is used. Similarly, the first latency (SW.dT) group is termed 0.1, corresponding to a latency of 0.1 seconds. This latency group includes latencies with duration greater or equal to 0.10 seconds, but less than 0.11 seconds (indicated by the group range 0.10≤SW.dT<0.11). The group midpoint is 0.105 [(0.10+0.11)/2]. The matrix distribution is computed during each individual of said time sequence windows 405 in a continuous series of said time sequence windows 405 during a recording. In this particular example duration of 6 seconds was used. The duration of each selectable time sequence window should lie in a time range of 5-15 seconds, though these durations represent no limitation of the scope of the invention.

with respect to columns equal to 0.169 seconds (2.746/16.25). The calculations are shown in more detail in Table 2.

TABLE 1

A small part of a first matrix showing the single pressure wave distribution of Time Sequence[360] presented in FIG. 4b.

| | | | Group name | | | | | |
|---|---|---|---|---|---|---|---|---|
| | | | 0.5 | 1 | 1.5 | 2 | 2.5 | 3 | 3.5 |
| | | | | | | Group range | | | |
| | | | 0.5 ≤ SW.dP < 1.0 | 1.0 ≤ SW.dP < 1.5 | 1.5 ≤ SW.dP < 2.0 | 2.0 ≤ SW.dP < 2.5 | 2.5 ≤ SW.dP < 3.0 | 3.0 ≤ SW.dP < 3.5 | 3.5 ≤ SW.dP < 4.0 |
| | | | | | | Group midpoint | | | |
| | | | 0.75 | 1.25 | 1.75 | 2.25 | 2.75 | 3.25 | 3.75 |
| 0.1 | 0.10 ≤ SW.dT < 0.11 | 0.105 | | | | | 1 | 1 | |
| 0.11 | 0.11 ≤ SW.dT < 0.12 | 0.115 | | | | | | 1 | |
| 0.12 | 0.12 ≤ SW.dT < 0.13 | 0.125 | | | | | | | |
| 0.13 | 0.13 ≤ SW.dT < 0.14 | 0.135 | | | | | | | |
| 0.14 | 0.14 ≤ SW.dT < 0.15 | 0.145 | | | | | | | |
| 0.15 | 0.15 ≤ SW.dT < 0.16 | 0.155 | | | | | | | |
| 0.16 | 0.16 ≤ SW.dT < 0.17 | 0.165 | | | | | | | |
| 0.17 | 0.17 ≤ SW.dT < 0.18 | 0.175 | | | | | | | |
| 0.18 | 0.18 ≤ SW.dT < 0.19 | 0.185 | | | | | | | |
| 0.19 | 0.19 ≤ SW.dT < 0.20 | 0.195 | | | | | | | |
| 0.2 | 0.20 ≤ SW.dT < 0.21 | 0.205 | | | | | | | |
| 0.21 | 0.21 ≤ SW.dT < 0.22 | 0.215 | | | | | | | |
| 0.22 | 0.22 ≤ SW.dT < 0.23 | 0.225 | | | | | | | |
| 0.23 | 0.23 ≤ SW.dT < 0.24 | 0.235 | | | | | | | 1 |
| 0.24 | 0.24 ≤ SW.dT < 0.25 | 0.245 | | | | | | | |
| 0.25 | 0.25 ≤ SW.dT < 0.26 | 0.255 | | | | | | | |
| 0.26 | 0.26 ≤ SW.dT < 0.27 | 0.265 | | | | | 1 | | |
| 0.27 | 0.27 ≤ SW.dT < 0.28 | 0.275 | | | | | | | |
| 0.28 | 0.28 ≤ SW.dT < 0.29 | 0.285 | | | | | | | |

When computing the mean frequency of a two-dimensional distribution with i rows and j columns, both dimensions must be considered (c=columns; r=rows). The result is the mean value of the distribution when the values from both the row and column mean are considered. First, the latency (SW.dT) mean value (or row mean), with respect to the amplitude (SW.dP) values (columns) is determined ($m_i$). The $m_i$ for each latency ($\Delta T$) row is determined, by using the equation 77.

$$m_i = \sum_{j=1}^{c} A_j w_{ij} \quad (77)$$

$A_j$ is the $j^{th}$ column midpoint, referring to an amplitude (SW.dP) group value; and $w_{ij}$ is the frequency (count) of the $i^{th}$ SW.dT row and $j^{th}$ SW.dP column cells.

$$\text{Row mean} = \text{Mean}(dt) = \frac{\sum_{i=1}^{r} m_i B_i}{\sum_{i=1}^{r} mi} \quad (78)$$

$B_i$ is the $i^{th}$ row SW.dT midpoint value (r=row). The term "$i^{th}$ SW.dT row and $j^{th}$ SW.dP column cell" refers to a matrix cell with the coordinates "$i^{th}$ row and $j^{th}$ column cell". Such a cell is found in the crossing point of a horizontal line drawn through the midpoint of row i, and a vertical line drawn through the midpoint of column j. To illustrate the process, the data of Table I are used to calculate the mean row value. Application of the equations (77) and (78) gives a row mean

TABLE 2

Computation of row [latency (SW.dT)] mean with respect to columns [amplitude (SW.dP)].

| $m_i$ | SW.dT$_i$ | $m_i$ × SW.dT$_i$ |
|---|---|---|
| 1 × 2.75 + 1 × 3.25 = 6.0 | 0.105 | 0.630 |
| 1 × 3.25 = 3.25 | 0.115 | 0.374 |
| 1 × 3.75 = 3.75 | 0.235 | 0.881 |
| 1 × 3.25 = 3.25 | 0.265 | 0.861 |
| Sum = 16.25 | | 2.746 |

Row mean: 2.746/16.25 = 0.169 seconds

Second, the mean (SW.dP) value (columns), with respect to the latency (SW.dT) value (rows), is determined ($m_j$). The column amplitude (SW.dP) mean value are found using the same approach as used for finding the mean row latency (SW.dT) value. First, the $m_j$ for each SW.dP column is found, as given in equation (79).

$$m_j = \sum_{i=1}^{r} B_i w_{ij} \quad (79)$$

$B_i$ is the $i^{th}$ row SW.dT midpoint, referring to a SW.dT group value and $w_{ij}$ is the frequency for the $i^{th}$ row and $j^{th}$ column.

$$\text{Column mean} = \text{Mean}(dP) = \frac{\sum_{j=1}^{c} m_j A_j}{\sum_{j=1}^{c} mi} \quad (80)$$

$A_j$ is the $j^{th}$ column SW.dP value midpoint (c=column). The calculations are shown in Table 3, using the equations (79) and (80), the column mean with respect to rows will be equal to 3.329 mmHg (2.746/0.825).

TABLE 3

Computation of column [amplitude (SW.dP)] mean with respect to rows [latency (SW.dT)].

| $m_j$ | | SW.dP$_j$ | $m_j \times$ SW.dP$_j$ |
|---|---|---|---|
| 1 × 0.105 = 0.105 | | 2.75 | 0.289 |
| 1 × 0.105 + 1 × 0.115 + 1 × 0.265 = 0.485 | | 3.25 | 1.576 |
| 1 × 0.235 = 0.235 | | 3.75 | 0.881 |
| Sum = 0.825 | | | 2.746 |

Column mean: 2.746/0.825 = 3.329 mmHg

Thus, the mean wave for the particular time sequence 405 shown in FIG. 4b (Time Sequence[360]) was 0.17 seconds/3.33 mmHg, the mean intracranial pressure (ICP) wave of this time sequence window 405 had a mean wave latency (TS.MeanWavedT) of 0.17 seconds (TS[360].MeanWavedT=0.17 sec) and an mean wave amplitude (TS.MeanWavedP) of 3.33 mmHg (TS[360].MeanWavedT=3.33 mmHg).

It is now described the process of computing mean wave rise time coefficient (TS.MeanWaveRT). This analysis comprises the steps of creating a second matrix that is one-dimensional, based on determining number of single pressure waves with pre-selected values related to rise time coefficient (SW.RT), the axis being related to an array of pre-selected values of rise time coefficient (SW.RT), and wherein indicating for each matrix cell in said second one-dimensional matrix a number of occurrences of pre-selected rise time coefficients (SW.RT) related to successive measurements of single pressure waves during said individual time sequence window. The single pressure wave parameter rise time coefficient (SW.RT) is categorized into groups, said groups reflecting ranges of said single wave (SW.x)-related parameter values. It is computed balanced position for a number of occurrences of said single pressure wave (SW.x)-related parameter rise time coefficient (SW.RT) in said second matrix, to yield an analysis output. Said balanced position of said second matrix of numbers of rise time coefficient (SW.RT) combinations corresponds to the mean wave rise time coefficient (TS.MeanWaveRT) of said time sequence window. TS.MeanWaveRT is computed according to equation (81). There are two variables $x_i$, and $w_i$ where $x_i$ is equal to the Group midpoint of each observed SW.RT and $w_i$ is equal to the frequency or number of occurrences within a Group range. The Observation value $x_i$ is the group midpoint of the observed SW.RT.

$$\bar{X} = \frac{\sum_{i=1}^{k} x_i w_i}{\sum_{i=1}^{k} w_i}, k = \text{number of observations} \quad (81)$$

An example of a second matrix is now shown in Table 4 (the observations are example values for the purpose of illustrating the concept).

TABLE 4

A second matrix showing a single pressure wave distribution.

| | Group name | | | |
|---|---|---|---|---|
| | 4.5 | 5.0 | 5.5 | 6.0 |
| Group range | 4.5 ≤ SW.dP < 5.0 | 5.0 ≤ SW.dP < 5.5 | 5.5 ≤ SW.dP < 6.0 | 6.0 ≤ SW.dP < 6.5 |
| Group midpoint | 4.75 | 5.25 | 5.75 | 6.25 |
| Observation | 2 | 1 | 4 | |

According to equation (81), balanced position of single pressure wave distribution of rise time coefficient in Table 4 equals:

(2×4.75 mmHg/sec+1×5.25 mHg/sec+4×5.75 mmHg/sec)/7=5.39 mmHg/sec.

Mean amplitude pressure of a time sequence window (TS.MeandP) corresponds to the sum of amplitude (SW.dP) values divided by the number of individual single pressure waves during said individual time sequence window. The mathematical process is further described in equation (21).

Mean latency of a time sequence window (TS.MeandT) corresponds to the sum of latency (SW.dT) values divided by number of individual single pressure waves during said individual time sequence window. The mathematical process is further described in equation (23).

Mean rise time coefficient of a time sequence window (TS.MeanRT) corresponds to the sum of rise time coefficient (SW.RT) values divided by the number of individual single pressure waves during said individual time sequence window. The mathematical process is further described in equation (25).

Absolute mean single wave pressure of a time sequence window (TS.Mean$_{SW}$P) corresponds to the sum of mean pressure (SW.Mean$_{SW}$P) values divided by number of individual single pressure waves during said individual time sequence window. Mean pressure value for an individual of said single pressure waves (SW.Mean$_{SW}$P) is the sum of sample values during the time of a wave duration, i.e. from starting diastolic minimum pressure (SW.P$_{min1}$) to ending diastolic minimum pressure (SW.P$_{min2}$)−1 divided by numbers of samples. For example, mean single wave pressure (TS.Mean$_{SW}$P) for the time sequence window 405 shown in FIG. 4b is the average of mean pressure for each of the five included single pressure waves 408 (termed SW[1], SW[2], SW[3], SW[4], and SW[5]), as further detailed in equation (29). Mean pressure for each included single pressure wave (SW.Mean$_{SW}$P) 408 is computed according to equation (9). Mean single wave pressure (TS.Mean$_{SW}$P) for the time sequence window 405 is the average of mean pressure of the five accepted single pressure waves [TS[360]. Mean$_{SW}$P=(11.87+11.89+11.65+11.56+12.36)/5=11.87 mmHg]. Mean pressure was 11.87 mmHg for SW[1] (913.99 mmHg/77 samples), 11.89 for SW[2] (1034.4 mmHg/87 samples), 11.65 mmHg for SW[3] (1036.85 mmHg/89 samples), 11.56 mmHg for SW[4] (971 mmHg/84 samples), and 12.36 for SW[5] (1087.68/88 samples).

Reference is now again given to FIG. 8. During said Computing Step the time sequence (TS.x)-related parameters 812 are determined on the basis of included time sequence windows 810, which were determined through the Identifying Steps. Based on the determined time sequence (TS.x)-related parameters 812, an analysis output 813 is determined in said Presentation Step (FIG. 8). Said analysis output 813 can be presented in different ways, for example including one or more of said parameters: Mean wave amplitude (TS.MeanWavedP), mean wave latency (TS.MeanWavedT), mean wave rise time coefficient (TS.MeanWaveRT), mean amplitude (TS.MeandP), mean latency (TS.MeandT), mean rise time coefficient (TS.MeanRT), and mean single wave pressure (TS.Mean$_{SW}$P).

During an ongoing sampling and digitalization of pressure-related signals 801, said analysis output 813 can be presented as numerical values of time sequence (TS.x)-related parameters 812 on a display 814 for each of said included time sequence windows 810. Given duration of said individual time sequence windows 810 of 6 seconds, the parameter value is displayed each 6 seconds on said display 814. For example, mean wave amplitude (TS.MeanWavedP) and mean wave latency (TS.MeanWavedT) can be displayed as the values 6.5 mmHg/0.23 seconds during Time Sequence[n] and as e.g. values 6.7 mmHg/0.24 seconds during Time Sequence[n+1] (the values 6.5 mmHg/0.23 seconds and 6.7 mmHg/0.24 seconds are only example values). Thereby, the parameter values are updated each 6 seconds, given this particular time window duration.

Another way of presenting the analysis output 813 of one or more of said time sequence parameters 812 is creation of histogram 815 distribution of values of said parameters 812. Typically such a histogram 815 includes a selectable number of time sequence windows of a signal 801. During an ongoing sampling and digitalization of pressure-related signals 801, said histogram 815 may include all included time sequence windows 810 that have been included so far. Given that e.g. 700 time sequence windows 810 have been included (i.e. Time Sequence[1] to Time Sequence[700]), the histogram 815 distribution is created based on time sequence (TS.x)-related parameters 812 of 700 included time sequence windows 810. Given that histogram 815 is created after the end of sampling of said pressure-related signals 801, the histogram 815 distribution is typically created based on time sequence (TS.x)-related parameters 812 of the included time sequence windows 810 of said signal 801.

Still another way of presenting the analysis output 813 of one or more of said time sequence parameters 812 is creation of a quantitative matrix 816 of values of said parameters 812. Typically such a quantitative matrix 816 includes a selectable number of time sequence windows of a signal 801. Said quantitative matrix 816 is created based on determining numbers of one of said time sequence parameters 812 with pre-selected values of said parameters 812, wherein one axis of the quantitative matrix 816 is related to an array of pre-selected values of said parameter 812, wherein the other axis is related to an array of pre-selected numbers of consecutive included time sequence windows 810, and wherein indicating for each matrix cell at respective intersections in said quantitative matrix 816 a number of occurrence of matches between a specific parameter 812 value and a specific number of included time sequence windows 810. The parameter 812 values are categorized into groups, said groups reflecting ranges of said parameter 812 values. Furthermore, the occurrence of matches in said quantitative matrix 816 is indicated through actual number or standardisation based number of matches during a specific measurement period, said standardisation based number of matches being a function of the length of the specific measurement period. A measurement period refers to given duration of said signal 801. A pressure signal 801 refers to a number of sequential and available pressure-related samples during a time period, wherein each of said time-related sequential samples can be referenced by a sample number and elapsed time determined by sample location number and sample frequency.

To further illustrate the creation of a quantitative matrix 816, a specific example is now presented, though this example is not intended to limit the scope of the invention.

Given a continuous intracranial pressure (ICP) signal 801 of 6 hours duration including a total of 3000 included, i.e. accepted, time sequence windows 810, there is allowed computation of time sequence (TS.x)-related parameters 812 of said 3000 included time sequence windows 810 (Time Sequence[1] to Time Sequence[3000]). In this example it is focused on mean wave amplitude (TS.MeanWavedP). The quantitative matrix shown in Table 5 is based on all the 3000 included time sequence windows 810 and corresponding 3000 (TS.MeanWavedP) parameter values. As indicated in Table 5, said quantitative matrix is created based on determining numbers of parameters 812 with pre-selected values of TS.MeanWavedP 812. The one axis of the quantitative matrix is related to an array of pre-selected values of TS.MeanWavedP 812 (in this example the pre-selected values were 4.0 mmHg, 5.0 mmHg, and 6.0 mmHg, referred to as group ranges). The parameter 812 values are categorized into groups, said groups reflecting ranges of said parameter 812 values: Amplitude Group 4: 4.0 mmHg≤TS.MeanWavedP<5.0 mmHg. Amplitude Group 5: 5.0 mmHg ≤TS.MeanWavedP<6.0 mmHg. Amplitude Group 6: 6.0 mmHg≤TS.MeanWavedP<7.0 mmHg. The other axis is related to an array of pre-selected numbers of included time sequence windows 810 (in this example the pre-selected numbers were 5, 10 and 20). Since the duration of each of said individual time sequence windows is known (6 seconds in this example), this other axis also is related to pre-selected durations (in this example 30 seconds, 60 seconds, and 120 seconds): Time Sequence Number Group 5: 0<N≤5 (corresponding to Time Group 0<Time≤30). Time Sequence Number Group 10: 5<N≤10 (corresponding to Time Group 30<Time≤60). Time Sequence Group 20: 10<N≤20 (corresponding to Time Group 60<Time ≤120). For each matrix cell is indicated at respective intersections in said quantitative matrix a number of occurrence of matches between a specific parameter (TS.MeanWavedP) 812 value and a specific number of included time sequence windows 810. The occurrence of matches in this matrix (Table 5) is indicated through actual number of matches during the specific measurement period of 6 hours. For example, according to this matrix distribution, mean wave amplitude (TS.MeanWavedP) values 812 equal to or larger than 5.0 mmHg but less than 6.0 mmHg occurring in five up to ten consecutive included time sequence windows 810 (5<N≤10) occurred two times during the recording of 6 hours including a total of 3000 included time sequence windows 810. In Table 6 is presented an identical quantitative matrix as in Table 5, though in this quantitative matrix (Table 6) the occurrence of matches is indicated through standardisation-based number of matches being a function of the length of the specific measurement period. The occurrence was standardised to a length of a recording period of 1 hour. Thereby each number is said matrix cell was multiplied with a factor equal to ⅙ in this specific example.

TABLE 5

A quantitative matrix of pre-selected combinations of TS.MeanWavedP
812 parameter values and number of included time sequence windows
810 (actual numbers presented in each matrix cell).

|  |  |  | Group name | |
|---|---|---|---|---|
|  | Group ranges | 4<br>$4.0 \leq DP < 5.0$ | 5<br>$5.0 \leq DP < 6.0$ | 6<br>$6.0 \leq DP < 7.0$ |
| 5 | $0 < N \leq 5$ | $0 < Time \leq 30$ | 8 | 5 | 2 |
| 10 | $5 < N \leq 10$ | $30 < Time \leq 60$ | 6 | 2 | 1 |
| 20 | $10 < N \leq 20$ | $60 < Time \leq 120$ | 3 | 1 |  |

DP refers to TS.MeanWavedP group range; N refers to number of included time sequence windows; and Time refers to the time of corresponding time sequences windows.

According to this quantitative matrix (Table 5), within said signal containing 3000 included time sequence windows there were five occurrences for which up to five consecutive time sequence windows had a time sequence parameter TS.MeanWavedP between 5.0 and up to 6.0 mmHg ($5.0 \leq DP < 6.0$; the number 5 is highlighted in bold type; Table 5).

TABLE 6

A quantitative matrix of pre-selected combinations of TS.MeanWavedP
812 parameter values and number of included time sequence windows 810
(standardization based numbers presented in each matrix cell).

|  |  |  | Group name | |
|---|---|---|---|---|
|  | Group ranges | 4<br>$4.0 \leq DP < 5.0$ | 5<br>$5.0 \leq DP < 6.0$ | 6<br>$6.0 \leq DP < 7.0$ |
| 5 | $0 < N \leq 5$ | $0 < Time \leq 30$ | 1.3 (=8 × ⅙) | 0.8 (=5 × ⅙) | 0.3 (=2 × ⅙) |
| 10 | $5 < N \leq 10$ | $30 < Time \leq 60$ | 1 (=6 × ⅙) | 0.3 (=2 × ⅙) | 0.2 (=1 × ⅙) |
| 20 | $10 < N \leq 0$ | $60 < Time \leq 120$ | 0.5 (=3 × ⅙) | 0.2 (=1 × ⅙) |  |

DP refers to TS.MeanWavedP group range; N refers to number of included time sequence windows; and Time refers to the time of corresponding time sequences windows.

In test recordings the quantitative matrix has been shown to be of great clinical significance, as related to several causes. It may be somewhat difficult to assess a continuous pressure recording of several hours duration since time sequence (TS.x)-related parameters may sometimes change over time. Said quantitative matrix may be used to get a useful summary of the recording. In particular, said quantitative matrix is useful for comparisons of continuous pressure recordings between different individuals. Test recordings including computation of quantitative matrixes of TS.MeanWavedP and TS.MeandP have been found to be of great value. The opportunity to standardize the quantitative matrix is particularly useful for comparisons of pressure recordings between individuals. Thereby, this inventive aspect further enhance the diagnostic value of pressure monitoring, Finally, the analysis output 813 of one or more of said time sequence parameters 812 may be presented in various other ways though specific examples are not presented in this context.

Concerning the method for processing continuous pressure-related signals derivable from locations inside or outside a human or animal body or body cavity as summarized in FIG. 8, some examples are given concerning the usefulness of the method.

For continuous intracranial pressure (ICP) signals 801, the method of computing time sequence (TS.x)-related parameters 812 such as mean wave amplitude (TS.MeanWavedP), mean amplitude (TS.MeandP), mean wave latency (TS.MeanWavedT), and mean latency (TS.MeandT) is useful for determining intracranial compliance (i.e. the inverse of intracranial elastanse). Determination of intracranial compliance is one of the major reasons for intracranial pressure (ICP) monitoring, though existing and currently used methods in no reliable way reveal intracranial compliance. Thus, the inventive method provides information within the pressure signal 801 that is not revealed by existing and currently used methods.

Using currently used, prior art technology of pressure monitoring, wrong calibration against atmospheric zero pressure level may give misleading results. Drift of zero pressure level is another great problem related to existing and currently used pressure monitoring. During long-term pressure monitoring, drift of zero pressure level may give misleading pressure measurements. Since the time sequence (TS.x)-related parameters 812 are relative values, errors related to wrong zero pressure level or drift in zero pressure level is eliminated by this invention.

By existing and currently used pressure monitoring technology, there is limited ways of controlling the quality of the pressure-related signals. A misleading pressure measurement may be made given wrong placement of the pressure sensor. There is minimal opportunity to control whether the pressure measurements are related to the cardiac beat induced pressures. By this invention the time sequence (TS.x)-related parameters 812 are only computed for included time sequence windows 810, including included single pressure waves 807. This approach gives an opportunity to control the quality of the pressure measurements.

Reference is now given to the third feature of this invention. This third feature of the invention is particularly illustrated in FIG. 9, as well as in FIGS. 7, 10 and 11.

Said third feature of the invention relates to a method for processing two or more simultaneous continuous pressure-related signals derivable from a human or animal body from one or more locations thereof electable from: inside the body, outside the body, inside body cavity, outside body cavity, comprising the steps of obtaining samples of said signals at specific intervals, and converting thus sampled pressure signals into pressure-related digital data with identical time reference, wherein for selectable and simultaneous time sequence windows the method comprises the further steps of identifying from said digital data signal single pressure waves related to cardiac beat-induced pressure waves within said two or more simultaneous signals constituting a pressure recording, and identifying from said digital data signal pressure waves related to artifacts or a combination of artifacts and cardiac beat-induced pressure waves within said two or more simultaneous signals constituting a pressure recording, and computing time sequence (TS.x)-related parameters of said single pressure waves during said identical time sequence windows within said two or more simultaneous signals constituting a pressure recording. The method comprises the further steps of determining relationships between time sequence (TS.x)-related parameters of said identical time sequence windows within said two or more simultaneous signals constituting a pressure recording, said relationships calculated as related time sequence (rTS.x) parameters, and determining said related time sequence (rTS.x) parameters for individual recordings or a population of recordings. Said related time sequence (rTS.x) parameters are further used for formula-based adjustment of time sequence windows of individual pressure-related signals, and for creating factorized time sequence (fTS.x) parameters of said individual time sequence windows of said individual continuous pressure-related signal.

Some remarks are required concerning simultaneously sampled pressure-related signals. With reference to FIG. 1, the notation: "Recording[1].Signal[m].Type.Location" denotes a specific Location 113 within a specific Type 104 within a specific Signal [n] 102, within a specific Recording [1] 101. The notation "Recording [1].Signal [m].Type.Sensor" denotes a specific Sensor 112 within a specific Type 104 within a specific Signal [n] 102, within a specific Recording [1] 101.

The present invention relates to a method for processing most types of continuous pressure-related signals derivable from human beings or animals, independent of pressure measurement locations and/or sensor type, and whether said sensor is placed inside or outside a human or animal body or a body cavity. Said method for processing continuous pressure-related signals is also independent of starting points of said continuous pressure-related signals. Furthermore, said method for processing continuous pressure-related signals is independent on type of pressure sensor, said sensor being placed inside or outside a human or animal body and/or body cavity.

Figure 9:
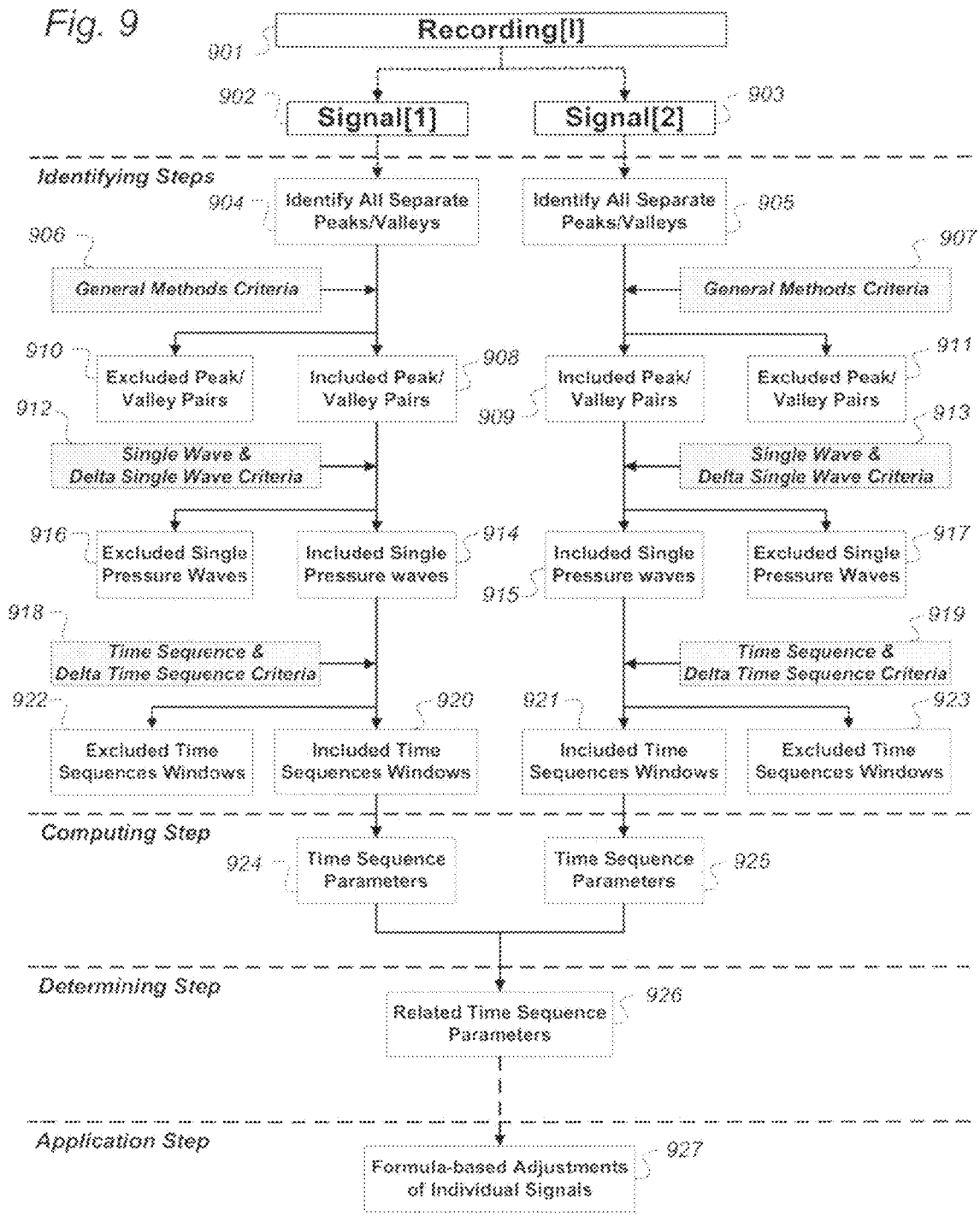
FIG. 9 shows a flow chart over a method for processing two simultaneous continuous pressure-related signals including determination of related time sequence (rTS.x) parameters, which are used for formula-based adjustments of individual signals.

Reference is now given to FIG. 9, wherein an overview of said method for analyzing two or more simultaneous continuous pressure-related signals is shown. From a recording 901 (Recording[1]) is analyzed two simultaneous signals, Signal [1] 902 and Signal[2] 903. Samples are obtained from each respective one of said pressure related signals Signal[1] 902 and Signal[2] 903, each such sample containing a pressure value at a specific time, and wherein said two or more pressure-related signals 902, 903 are all sampled simultaneously. Each of said sampled pressure signals 902, 903 refers to a number of sequential and available pressure samples during a time period. Selectable and simultaneous time sequence windows are a selected time frame of a sampled signal. Each of such simultaneous selectable time sequence windows is a function of a number of time-related sequential samples, each individual sample referenced by a sample number and elapsed time determined by sample location number and sample frequency. Concerning notation related to recording 901 and signals 902 and 903, it is referred to FIG. 1. In short, a recording 901 is one or more simultaneous signals (e.g. Signal[1] 902 and Signal[2] 903) derivable from locations inside or outside a human or animal body or body cavity, each of said signals having identical time reference, though it is not a requirement that the start time is identical for all signals of a recording. Attributes of each signal include type, frequency, and actual samples. As indicated with reference to FIG. 1, a signal is equivalent to: Recording [1].Signal [m].Samples [n], wherein each of said samples contains a pressure value at a specific time.

As indicated in FIG. 9, the process method incorporates different Identifying Steps, Computing Step, Determining and Application Step. Said Identifying Steps include identification of all separate peaks and valleys 904, 905 in said simultaneously sampled signals (Signal[1] 902 and Signal[2] 903) that constitute a pressure recording (Recording[1] 901). Each of said peaks is a sample with a pressure value and a time stamp or location, and each of said valleys is a sample with a pressure value and a time stamp or location.

The result of applying signal specific General Methods Criteria 906, 907 is either included peak/valley pair combinations 908, 909 or excluded peak/valley pair combinations 910, 911 in said simultaneous signals (Signal[1] 902, Signal [2] 903) constituting a pressure recording (Recording[1] 901).

After applying signal specific Single Wave & Delta Single Wave Criteria 912, 913 to said included peak/valley pairs 908, 909, the output is either included single pressure waves 914, 915 or excluded pressure waves 916, 917 in said simultaneous signals (Signal[1] 902, Signal[2] 903), constituting a pressure recording (Recording[1] 901). Said criteria 912, 913 relate to thresholds and ranges of single pressure wave (SW.x)-related parameters and delta single pressure wave (ΔSW.x)-related parameters during time sequence windows. After applying the Single Wave & Delta Single Wave Criteria 912, 913 to included pair combinations of peak/valley pairs 908, 909 in said simultaneous signals (Signal[1] 902, Signal[2] 903), said pairs 908, 909 correspond to included single pressure waves 914, 915 in said simultaneous signals (Signal[1] 902, Signal [2] 903) constituting a pressure recording (Recording[1] 901). Pair combinations of diastolic minimum pressure (SW.$P_{min1}$) and systolic maximum pressure (SW.$P_{max}$) characterize single pressure waves created by cardiac beat-induced pressure waves. Said criteria 912, 913 exclude for further analysis pressure waves 916, 917 (i.e. minimum-maximum pressure (SW.$P_{min1}$/SW.$P_{max}$) pairs) during said time sequence windows with said single pressure wave (SW.x)- and delta single pressure wave (ΔSW.x)-related parameters outside selected criteria 912, 913 for thresholds and ranges of said parameters. Said criteria 912, 913 include for further analysis single pressure waves 914, 915 having single pressure wave (SW.x)- and delta single pressure wave (ΔSW.x)-related parameters within selected criteria 912, 913 for thresholds and ranges of said single pressure wave (SW.x)-related parameters. Pair combinations of diastolic minimum pressure (SW.$P_{min1}$) and systolic maximum pressure (SW.$P_{max}$) correspond to the diastolic minimum pressures and systolic maximum pressures of individual of pressure waves created by each of said cardiac beats.

Signal-specific Time Sequence & Delta Time Sequence Criteria 918, 919 are applied to each of said time sequence windows in a continuous series of time sequence windows of said simultaneous signals (Signal[1] 902, Signal[2] 903) constituting a pressure recording (Recording[1] 901). Said criteria 918, 919 for thresholds and ranges of said time sequence (TS.x) and delta time sequence (ΔTS.x)-related parameters determine included time sequence windows 920, 921 and excluded time sequence windows 922, 923 of said simultaneous signals (Signal[1] 902, Signal[2] 903) constituting a pressure recording (Recording[1] 901). Said criteria 918, 919 exclude for further analysis time sequence windows 922, 923 with time sequence (TS.x)- and delta time sequence (ΔTS.x)-related parameters outside selected criteria 918, 919 for thresholds and ranges of said parameters. Said criteria 918, 919 include for further analysis time sequence windows 920, 921 having time sequence (TS.x) and delta time sequence (ΔTS.x)-related parameters within selected criteria 918, 919 for thresholds and ranges of said time sequence (TS.x) and delta time sequence (ΔTS.x)-related parameters.

It should be understood that said General Methods Criteria 906, 907, Single Wave & Delta Single Wave Criteria 912, 913 and Time Sequence & Delta Time Sequence Criteria 918, 919 are signal-specific and location-specific, meaning that said criteria are different for different types of signals and locations in said signals. In a next Computing Step (FIG. 9) is computed time sequence (TS.x)-related parameters 924, 925 for each individual of said included time sequence windows 920, 921 of said simultaneous signals (Signal[1] 902, Signal[2] 903) constituting a pressure recording (Recording[1] 901).

The Identifying Steps are applied to each of said time sequence windows in a continuous series of said time sequence windows during a recording.

The Computing Step is applied to each of said included time sequence windows 920, 921 in a continuous series of said time sequence windows during a recording.

In a final Determining Step, there is determined relationships between time sequence (TS.x)-related parameters 924, 925 of said identical included time sequence windows 920, 921 within said simultaneous signals (Signal[1] 902, Signal[2] 903) constituting a pressure recording (Recording[1] 901). Said relationships are calculated as related time sequence (rTS.x) parameters 926, determined for individual recordings, as well as for a population of recordings. Said related time sequence (rTS.x) parameters 926 can be constant relationships and/or formula-based relationships between identical time sequence (TS.x)-related parameters 924, 925 of different pressure signals (Signal[1] 902, Signal[2] 903) with identical time reference. Said related time sequence (rTS.x) parameters are computed for each individual of said included time sequence windows 920, 921 in a continuous series of time sequence windows of said signals (Signal[1] 902, Signal[2] 903). In addition, for all included time sequence windows 920, 921 in said signals (Signal[1] 902, Signal[2] 903), the mean value of such parameters 926 is determined. For a population of recordings, population-based formulas for said related time sequence (rTS.x)-related parameters 926 are determined. Based on said related time sequence (rTS.x) parameters 926, formula-based adjustments of time sequences of individual pressure-related signals 927 are made possible. Thereby, factorized time sequence (fTS.x) parameters of individual time sequence windows of individual continuous pressure-related signal are created from said formula-based adjustments 927. Factorized time sequence (fTS.x) parameters are derived from related time sequence (rTS.x) 926 values together with time sequences of the signal being factorized.

Concerning the Identifying Steps, the method is comparable to the process described for FIGS. 2, 3a, 3b, 3c, 4a, 4b, 5a, 5b, 6, and 7a, but with reference to FIG. 9 the method is applied to several simultaneous signals.

Details about General Methods Criteria 906, 907, Single Wave & Delta Wave Criteria 912, 913 and Time Sequence & Delta Time Sequence Criteria 918, 919 are already commented on with reference to FIGS. 2 and 8, and these aspects are therefore not commented on further in the context of FIG. 9.

With reference to FIG. 9 it is made clear that said criteria are signal-specific and location specific being different for different signal types and locations of a signal.

Computation of related time sequence (rTS.x) parameters can be selected from the group of relationship of mean values of starting diastolic minimum pressure of two or more perfect time sequence windows from two or more different pressure signals (rTS.$P_{min1}$), relationship of standard deviation of mean values of starting diastolic minimum pressure of two or more perfect time sequence windows from two or more different pressure signals (rTS.MeanP$_{min1}$_STD), relationship of mean values of systolic maximum pressure of two or more perfect time sequence windows from two or more different pressure signals (rTS.MeanP$_{max}$), relationship of standard deviation of mean values of systolic maximum pressure of two or more perfect time sequence windows from two or more different pressure signals (rTS.MeanP$_{max}$_STD), relationship of mean amplitude values of two or more perfect time sequence windows from two or more different pressure signals (rTS.MeandP), relationship of standard deviation of mean amplitude of two or more perfect time sequence windows from two or more different pressure signals (rTS.MeandP_STD), relationship of mean latency of two or more perfect time sequence windows from two or more different pressure signals (rTS.MeandT), relationship of standard deviation of mean latency of two or more perfect time sequence windows from two or more two different pressure signals (rTS.MeandT_STD), relationship of mean rise time coefficient of two or more perfect time sequence windows from two or more different pressure signals (rTS.MeanRT), relationship of standard deviation of mean rise time coefficient of two or more perfect time sequence windows from two or more different pressure signals (rTS.MeanRT_STD), relationship of mean wave duration of two or more perfect time sequence windows from two or more different pressure signals (rTS.MeanWD), relationship of standard deviation of mean wave duration of two or more perfect time sequence windows from two or more different pressure signals (rTS.MeanWD_STD), relationship of mean single wave pressure of two or more perfect time sequence windows from two or more different pressure signals (rTS.Mean$_{SW}$P), relationship of standard deviation of mean single wave pressure of two or more perfect time sequence windows from two or more different pressure signals (rTS.Mean$_{SW}$P_STD), relationship of mean diastolic minimum pressure difference of two or more perfect time sequence windows from two or more different pressure signals (rTS.MeanDiff_P$_{min}$), relationship of standard deviation of mean diastolic minimum pressure difference of two or more perfect time sequence windows from two or more different pressure signals (rTS.MeanDiff_$P_{min}$_STD), relationship of mean systolic maximum pressure difference of two or more perfect time sequence windows from two or more different pressure signals (rTS.MeanDiff_$P_{max}$), relationship of standard deviation of mean systolic maximum pressure difference of two or more perfect time sequence windows from two or more different pressure signals (rTS.MeanDiff_$P_{max}$_STD), relationship of mean amplitude difference of two or more perfect time sequence windows from two or more different pressure signals (rTS.MeanDiff_dP), relationship of standard deviation of mean amplitude difference of two or more perfect time sequence windows from two or more different pressure signals (rTS.MeanDiff_dP_STD), relationship of mean latency difference of two or more perfect time sequence windows from two or more different pressure signals (rTS.MeanDiff_dT), relationship of standard deviation of mean latency difference of two or more perfect time sequence windows from two or more different pressure signals (rTS.MeanDiff_dT_STD), relationship of mean rise time coefficient difference of two or more perfect time sequence windows from two or more different pressure signals (rTS.MeanDiff_RT), relationship of standard deviation of mean rise time coefficient difference of two or more perfect time sequence windows from two or more different pressure signals (rTS.MeanDiff_RT_STD), relationship of mean wave duration difference of two or more perfect time sequence windows from two or more different pressure signals (rTS.MeanDiff_WD), relationship of standard deviation of mean wave duration difference of two or more perfect time sequence windows from two or more two different pressure signals (rTS.MeanDiff_WD_STD), relationship of mean single wave pressure difference of two or more perfect time sequence windows from two or more different pressure signals (rTS.MeanDiff_$Mean_{SW}P$), relationship of standard deviation of mean single wave pressure difference of two or more perfect time sequence windows from two or more two different pressure signals (rTS.MeanDiff_$Mean_{SW}P$_STD), relationship of single wave count of two or more perfect time sequence windows from two or more different pressure signals (rTS.SWCount), relationship of mean wave amplitude of two or more perfect time sequence windows from two or more different pressure signals (rTS.MeanWavedP), relationship of mean wave latency of two or more perfect time sequence windows from two or more different pressure signals (rTS.MeanWavedT), and relationship of mean wave rise time coefficient of two or more perfect time sequence windows from two or more different pressure signals (rTS.MeanWaveRT).

The term "perfect" in this context implies the term "accepted" after application of very strict criteria.

It should be noted that said simultaneous continuous pressure-related signals (Signal[1] and Signal[2]) include two dimensions, a pressure scale and a time scale. The related time sequence (rTS.x) parameters which describe the relationships between two signals are based on observations between identical time sequences from said signals (Signal[1].TS[x] and Signal[2].TS[x]), where x denotes a specific location and time within the same recording (Recording[1]). Thus, the related time sequence (rTS.x) parameters establish relationships for both the pressure and time dimensions of a continuous signal.

In test recordings, related time sequence (rTS.x) parameters found useful for comparing pressure-related characteristics between simultaneous signals include such as, e.g.: rTS.MeandP, rTS.MeandP_STD, rTS.MeanRT, and rTS.MeanWavedP. Parameters found useful for comparisons of time related characteristics include such as, e.g.: rTS.MeandT, rTS.MeanWD, rTS.MeanWD_STD, rTS.MeanDiff_dT, and rTS.MeanDiff_WD. Comparisons of rTS.x values between different time sequence parameters may be even more powerful in determining relationships.

In general, it should be noted that the sensor element itself wherefrom the pressure signals are derived, could be located both within and outside the body cavity. The type of sensor does not represent a limitation of the scope of the present invention. For example, intra-dural pressure signals may be derived from a fluid catheter placed via a cannula within the intra-dural compartment, wherein the sensor element can be placed outside the body thus deriving pressure signals from the catheter fluid outside the body and in distance from the location per se (i.e. the intra-dural compartment). In another situation, a sensor element itself is located on the catheter tip that is placed within the intra-dural compartment. The situation is similar for arterial blood pressure (ABP) monitoring, when a catheter is placed via an intra-arterial cannula, and the sensor element is either outside the body measuring pressures within the distal part of the catheter or the sensor element is placed on the proximal tip of the catheter placed within the intra-arterial compartment. Therefore, the sensor type and sensor location represents no limitation of the scope of the invention.

Continuous simultaneous signals within a recording may be derivable from a human or animal body from one or more locations thereof electable from: inside the body, outside the body, inside body cavity, outside body cavity. Reference is now given to FIG. 9 showing two different signals (Signal[1] 902, Signal[2] 903), and examples are now given concerning simultaneous pressure-related signals from different locations or pressure sources. Said simultaneously sampled signals can be obtained from two simultaneous continuous intracranial intra-dural and epidural pressure-related signals. In this situation the simultaneous signals constituting a recording are derived simultaneously from two different locations: Inside the dura mater (i.e. intra-dural) and outside the dura mater (i.e. epidural). For example, the corresponding notations can be: Recording[60].Signal[1].ICP.Intra-dural; and Recording[60].Signal[2].ICP.Epidural. These different extra- and intra-dural compartments can in a way be considered as different body cavities though both the extra- and intra-dural body cavities are located within the intracranial compartment and are measuring from the same pressure origin.

Continuous signals can be obtained from at least two simultaneous continuous intracranial intra-dural and intraspinal intra-dural cerebrospinal fluid pressure signals. For example, said intradural pressure-related signals may be derived from a catheter placed within the cerebral ventricles, or a sensor placed within the brain parenchyma or within the subdural extra-cerebral compartment. The sensor element may be within the intra-dural compartment or outside the body measuring fluid pressure within said catheter. Said intraspinal intra-dural cerebrospinal fluid pressure signals may as well be derived from a fluid-filled catheter with the sensor on the outside of the body or via a sensor element introduced to the intra-spinal and intra-dural compartment. Intraspinal intra-dural cerebrospinal fluid pressure signals are obtained during so-called infusion tests.

In another situation, said sampled signals are obtained from at least two simultaneous continuous intracranial intra-dural and extra-cranial pressure signals indicative of intracranial pressure signals. Said extra-cranial pressure signals indicative of intracranial pressure signals can be derived from various sources. Some examples are given though these examples are not intended to limit the scope of the invention:
a) Firstly, said extra-cranial pressure signals can be related to air pressure signals derivable from within a human or animal outlet-sealed outer ear channel. An open and air-filled catheter is placed within the outer ear channel after airtight closing of the outer ear channel, thus allowing sampling of pressure-related signals from the outer airtight outer ear channel. A detailed description of this concept is given separately.
b) Secondly, said extra-cranial pressure signals can also be transcranial Doppler signals, that are transformable into pressure-related signals indicative of intracranial pressure signals. Transcranial Doppler measures arterial blood flow signals that are transformable into pressure-related signals indicative of intracranial pressure signals.
c) Thirdly, said extra-cranial pressure signals can be cranial impedance-related signals, being transformable into pressure-related signals indicative of intracranial pressure signals.
d) Fourthly, said extra-cranial pressure signals are fontanel applanation pressure signals, being transformable into pressure-related signals indicative of intracranial pressure signals. This strategy is particularly useful in children below 1-2 years of age with a non-closed fontanel.
e) Fifthly, said extra-cranial pressure signals are ocular applanation pressure signals.

Said simultaneous pressure samples derived from intracranial intra-dural and extra-cranial pressure signals indicative of intracranial pressure signals may as well be combined with outer simultaneous signals constituting a pressure recording. Such signal may be arterial blood pressure (ABP) signals or electrocardiogram (ECG) signals.

Simultaneous pressure-related signals may be sampled from at least two simultaneous continuous intra-arterial and extra-arterial pressure signals indicative of intra-arterial pressure signals. Said extra-arterial pressure signals indicative of intra-arterial pressure signals can be derived from various sources. Some examples can be given though these examples are not intended to limit the scope of the invention: Firstly, said extra-arterial pressure signals are arterial applanation pressure signals, being transformable into pressure-related signals indicative of intra-arterial pressure signals. Secondly, said extra-arterial pressure signals are pulse oxymetry signals, being transformable into pressure-related signals indicative of intra-arterial pressure signals. Thirdly, said extra-arterial pressure signals are any physiological signals, being transformable into pressure-related signals indicative of intra-arterial pressure signals.

The significance of the procedure described in FIG. 9 has been shown for different types of test recordings. By using the method described in FIG. 9 it became possible to obtain nearly identical time sequence (TS.x) parameters (e.g. TS.MeandP, TS.MeanWavedP), independent whether the pressure sensor was placed within the epidural space or intra-dural. Thus, this feature of the invention makes it possible to measure intracranial pressure (ICP) by placing a sensor within the epidural space instead of within the brain tissue itself (intra-dural). This represents a major advantage since epidural placement of a sensor is less invasive with minimal opportunity of damaging the brain. This aspect of the invention is further commented on with reference to FIGS. 7a and 7b.

In test recordings using the method described in FIG. 9, it also was possible to compute nearly identical time sequence (TS.x) parameters whether location of intracranial pressure (ICP) signals was intra-dural within the brain parenchyma or within the spinal (lumbar) cerebrospinal fluid (CSF) cavity. Thus, it was possible to precisely measure intracranial pressure (ICP) by placing a cannula within the lumbar cerebrospinal fluid (CSF) cavity. This represents a great advantage, since the procedure is less invasive.

In test recordings it was also possible to obtain nearly identical time sequence (TS.x) parameters by a sensor placed within the outer ear channel as by placing the sensor intradurally within the brain parenchyma. Aspects of this procedure are further described in FIGS. 10 and 11. Obviously it will be a great advantage to be able to measure intracranial pressure (ICP) by placing a sensor within the outer ear channel rather than by placing a sensor within the brain parenchyma or within the epidural space.

These examples are not intended to limit the scope of the invention. A major application is within the field of arterial blood pressure (ABP) monitoring, without placing a sensor within the blood vessel itself. Nevertheless, test recordings show that the method described in connection with FIG. 9 provides for a strategy of measuring pressures inside a body or body cavity by placing the sensor outside said body or body cavity.

Reference is now given to FIGS. 7a and 7b, to further illustrate the concept of computing related time sequence (rTS.x) parameters on the basis of time sequence (TS.x)-related parameters of simultaneous signals (corresponding to related time sequence parameters 926 and time sequence parameters 924, 925 of Signal[1] 902 and Signal[2] 903; FIG. 9). In FIG. 7a is shown a continuous intracranial intra-dural pressure (ICP) signal 701 derived from a sensor within the brain parenchyma (Signal[1] 701) (Recording[62].Signal[1]. ICP.Intra-dural), and in FIG. 7b is shown a continuous intracranial epidural pressure (ICP) signal 702 derived from a sensor within the epidural space (Signal[2] 702) (Recording[62]. Signal[2].ICP.Epidural). Thus, both signals Signal[1] 902 and Signal[2] 903 were from the same recording (Recording [62]), and were sampled simultaneously with identical time reference, thus with identical time scale 703 for both Signal [1] 701 and Signal[2] 702. The pressure scale 704 of Signal[1] 701 (FIG. 7a) and the pressure scale 705 of Signal[2] 702 (FIG. 7b) had identical resolution though the absolute pressure levels were different. For both signals are shown two subsequent time sequence windows, termed Time Sequence [30] 706 (n−1) and Time Sequence[31] 707 (n). These were included time sequence windows (see FIG. 9). For Signal[1] 701 the amplitudes (SW.dP) of the included single pressure waves 708 within the first time sequence window (Time Sequence[30] 706) are numbered 709 (SW[1].dP), 710 (SW [2].dP), 711 (SW[3].dP), 712 (SW[4].dP), 713 (SW[5].dP), and 714 (SW[6].dP). For Signal[1] 701 the amplitudes (SW.dP) of the seven included single pressure waves 708 within the second time sequence window (Time Sequence [31] 707) are numbered 715 (SW[1].dP), 716 (SW[2].dP), 717 (SW[3].dP), 718 (SW[4].dP), 719 (SW[5].dP), 720 (SW [6].dP) and 721 (SW[7].dP). For Signal[2] 702 the amplitudes (SW.dP) of the six included single pressure waves 708 within the first time sequence window (Time Sequence[30] 706) are numbered 722 (SW[1].dP), 723 (SW[2].dP), 724 (SW[3].dP), 725 (SW[4].dP), 726 (SW[5].dP), and 727 (SW

[6].dP). For Signal[2] 702 the amplitudes (SW.dP) of the seven included single pressure waves 708 within the second time sequence window (Time Sequence[31] 707) are numbered 728 (SW[1].dP), 729 (SW[2].dP), 730 (SW[3].dP), 731 (SW[4].dP), 732 (SW[5].dP), 733 (SW[6].dP) and 734 (SW[7].dP).

FIGS. 7*a* and 7*b* show two simultaneous continuous pressure-related signals 701, 702 derived from different locations that are converted into pressure-related digital data with identical time reference 703. For each of said simultaneous time sequence windows (either Time Sequence[30] 706 or Time Sequence[31] 707) are identified the single pressure waves related to cardiac beat-induced pressure waves within said two or more simultaneous signals (Signal[1] 701 and Signal[2] 702) of a pressure recording. Some of said time sequence (TS.x)-related parameters of said single pressure waves 708 during said identical time sequence windows (either Time Sequence[30] 706 or Time Sequence[31] 707) within said two simultaneous signals (Signal[1] 701 and Signal[2] 702) of a pressure recording, are listed in Table 7.

chart of FIG. 9. The recording shown in FIGS. 7*a* and 7*b* Recording[62] (901) included two signals: Recording[62].Signal[1].ICP.Intra-dural (902); Recording[62].Signal[2].ICP.Epidural (903). Within each of said signals (902, 903) were a total of 3600 time sequence windows. After the Identifying Steps indicated in FIG. 9, a total of 3100 included time sequence windows (920, 921) were determined within each of said signals (902, 903) [i.e. within each signal (902, 903) a total of 500 excluded time sequence windows 922, 923 were determined]. For each of said 3100 included, i.e. accepted, time sequence windows Time Sequence[1] to Time Sequence[3100] (920, 921), the time sequence (TS.x)-related parameters (924, 925) TS.MeanWavedT and TS.MeandT were determined, and the related time sequence (rTS.x) parameters (926) rTS.MeanWavedT and rTS.MeandT were computed for each individual of said 3100 time sequence windows (920, 921). Subsequently, the mean value of these parameters (926) were determined for all included time sequence windows (920, 921) of said pressure recording Recording[62] (901). For both the related time sequence (rTS.x) parameters (926)

TABLE 7

Data related to time sequence windows shown in FIGs. 7a and 7b.

| | Time sequence (TS.x)-related parameters | | | |
|---|---|---|---|---|
| | TS.MeanWavedP | TS.MeanWavedT | TS.MeandP | TS.MeandT |
| | Time Sequence[30] | | | |
| Signal[1] | 5.0 mmHg | 0.265 sec | 5.5 mmHg | 0.265 sec |
| Signal[2] | 5.9 mmHg | 0.275 sec | 5.7 mmHg | 0.275 sec |
| | Time Sequence[31] | | | |
| Signal[1] | 5.1 mmHg | 0.268 sec | 5.2 mmHg | 0.268 sec |
| Signal[2] | 5.9 mmHg | 0.276 sec | 6.0 mmHg | 0.276 sec |
| | Related time sequence (rTS.x) parameter values | | | |
| | rTS.MeanWavedP | rTS.MeanWavedT | rTS.MeandP | rTS.MeandT |
| | Time Sequence[30] | | | |
| | 0.85 (=5.0/5.9) | 0.96 (=0.265/0.275) | 0.96 (=5.5/5.7) | 0.96 (=0.265/0.275) |
| | Time Sequence[31] | | | |
| | 0.86 (=5.1/5.9) | 0.97 (=0.268/0.276) | 0.87 (=5.2/6.0) | 0.97 (=0.268/0.276) |

With reference to Table 7, some comments should be made: Firstly, it should be noted that the time sequence (TS.x)-related parameters TS.MeanWavedP and TS.MeandP were almost identical, and also the time sequence (TS.x)-related parameters TS.MeanWavedT and TS.MeandT were identical. Secondly, the various time sequence (TS.x)-related parameters changed marginally between Time Sequence[30] and Time Sequence[31]. Thirdly, the related time sequence (rTS.x) parameters were constant relationships between said time sequence (TS.x)-related parameters. These two simultaneous time sequence windows (Time Sequence[30] 706 or Time Sequence[31] 707) were selected from a group of 3100 included time sequence windows (Time Sequence[1] to Time Sequence[3100]) of a recording with originally 3600 time sequence windows within each of said two signals (Signal[1] and Signal[2]) constituting the recording (Recording[62]).

To explain in more detail the results shown in Table 7 and FIG. 7, this specific example is now explained with reference to FIG. 9 wherein reference numbers to FIG. 9 is given in parenthesis. This is done in order to further clarify the flow rTS.MeanWavedP and rTS.MeandP, the mean value was 0.86. Furthermore, eight test recordings were made (Recording[61], Recording[62] . . . . Recording[68]) with similar simultaneous intra-dural and epidural signals as in Recording[62]: Recording[62].Signal[1].ICP.Intra-dural; Recording[62].Signal[2].ICP.Epidural. Said population of recordings was categorized according to signal type since only simultaneous intra-dural and epidural signals were included in said recordings (901). For this population of recordings, the related time sequence (rTS.x) parameters (926) rTS.MeanWavedP and rTS.MeandP were determined according to equation (84).

Further aspects of determination of these related time sequence (rTS.x) parameters will now be explained. Some general comments are made concerning related time sequences (rTS.x) and factorized time sequences (fTS.x) with focus on notation. Through the invention it has been found useful to include separate notation related to said related time sequences (rTS.x) and factorized time sequences (fTS.x). Simultaneously included time sequences from two or more simultaneous signals are termed Perfect Time Sequences (i.e. PerfectTS). Perfect time sequences (PerfectTS) only include identical included time sequences from two or more signals wherein time reference is identical between all included time sequences. So-called Perfect Recording includes said Perfect Time Sequences, giving this notation: PerfectRecording[s]. Signal[m].PerfectTS[u].

The term PopulationCount (PopCount) relates to a defined group of Perfect Time Sequences (PerfectTS[u]), wherein said defined group is determined by attributes such as signal type, location and sensor type.

In general, a related time sequence (rTS) is defined by equation (82):

$$rTS = f(x) \tag{82}$$

According to this equation, rTS is a function ($f$) of input x, wherein x is Perfect time sequences (PerfectTS) in general.

One example of input (x) is shown and expressed in equation (83):

$$f(x) = f1(PerfectTS.MeanWavedP) + f2(PerfectTS.MeanWavedP\_STD) + fn(PerfectTS.x) + \tag{83}$$

The example shown in equation (83) indicates that input (x) can be a function of several Perfect time sequence (PerfectTS)-parameters.

In another example only the parameter PerfectTS.MeanWavedP is used as input, among all possible PerfectTS.x parameters, as detailed in equation (84).

$$rTS.MeandP = \left( \sum_{n=1}^{PopCount} \frac{ICP.Epidural.PerfectTS[u].MeandP}{ICP.Intra-dural.PerfectTS[u].MeandP} \right) / PopCount \tag{84}$$

The specific example given with reference to FIGS. 7a and 7b used this specific formula for determining the related time sequence parameter rTS.MeandP.

It should be noted as well that rTS[=$f(x)$] can also be described with a much more advanced mathematical method and formula-based relationships between the individual Perfect time sequence (PerfectTS.x) parameters. The specific examples shown here are intended to illustrate the concept, not to limit the scope of the invention.

Some general comments are also given with reference to the factorized time sequences. In general a factorized time sequence (fTS) can be expressed according to equation (85):

$$fTS[o] = f(x) \tag{85}$$

A factorized time sequence (fTS[o]) is a function of input x, wherein x is an input signal, as specified in equation (86):

$$fTS[o] = f(Recording.Signal[m]) \tag{86}$$

In this example, the input signal x is Recording.Signal[m], which is a specified signal (Signal[m]) in a non-specified recording.

In another example, the input signal x is Signal.TS[o], which is a specific perfect time sequence (PerfectTS[u]) in a non-specific signal, as shown in equation (87):

$$fTS[o] = f(Signal.PerfectTS[u]) \tag{87}$$

These equations illustrate the concept that a factorized time sequence (fTS) is a result of a function that contains a method and/or formula based on related time sequence (rTS) observations. Said method (formula) can be based on one or more of said PerfectTS.x-related parameters. Said factorized time sequences (fTS) thus can be considered as predicted time sequences as well.

Reference is again given to the population of test recordings (Recording[61] to Recording[68]) with similar simultaneous intra-dural and epidural signals as in Recording[62]: Recording[62].Signal[1].ICP.Intra-dural; Recording[62].Signal[2].ICP.Epidural. As already commented on, the related time sequence (rTS.x) parameters (926) rTS.MeanWavedP and rTS.MeandP were determined according to equation (84) for this population of recordings. The mean value for said population of recordings of related time sequence (rTS.x) parameters (926) rTS.MeanWavedP and rTS.MeandP were 0.83 and 0.87, respectively. Said population of recordings could also enable determination of population-based formulas for said related time sequence (rTS.x)-related parameters (926). It should be noted that the related time sequence (rTS.x) parameters rTS.MeanWavedP and rTS.MeandP only establish relationships for the pressure scale of said pressure recordings. In this context is as well explained the process of determining factorized time sequence (fTS.x) parameters, derived from related time sequence (rTS.x) values (926) of continuous pressure-related signals of individual pressure recordings. According to this example, factorized time sequence (fTS.x) parameters could be derived from related time sequence (rTS.x) values (926) of continuous pressure-related signals of a population of pressure recordings (Recording[61] to Recording[68]). For this population, rTS.MeanWavedP was equal to 0.83 and rTS.MeandP equal to 0.87. Since the epidural continuous signals are so-called non-gold standard signals, it may be useful factorize the time sequence parameters of these epidural signals. Factorization of such a specific signal is performed as follows: For said signal (903) all the included time sequence windows (921) are determined according to the Identifying Steps shown in FIG. 9, and time sequence parameters (925) determined for said included time sequence windows (921). For example, a factorized time sequence (fTS.x) parameter fTS.MeandP is created by multiplying the time sequence TS[x].MeandP parameter of each of said included time sequence windows with the value 0.87 (see equation 87). This is only one example of creating factorized time sequence (fTS.x)-related parameters, and this specific example is not intended to limit the scope of the invention. The fTS.MeandP could as another example be calculated upon a multiple parameter relation such as rTS.x[1], rTS.x[2] . . . , wherein x[1] is the first related parameter and x[2] is the second related parameter. It is referred to equations 85 and 86.

Said creation of factorized time sequence (fTS.x) parameters relate to formula-based adjustment of time sequence (TS.x)-related parameters of individual time sequence windows of continuous pressure-related signals, said factorized time sequence (fTS.x) parameters can be selected from the group of:

factorized mean value of starting diastolic minimum pressure of a time sequence window (fTS.MeanP$_{min1}$), factorized standard deviation of mean value of starting diastolic minimum pressure of a time sequence window (fTS.MeanP$_{min1}$\_STD), factorized mean value of systolic maximum pressure of a time sequence window (fTS.MeanP$_{max}$), factorized standard deviation of mean value of systolic maximum pressure of a time sequence window (fTS.MeanP$_{max}$\_STD), factorized mean amplitude of a time sequence window (fTS.MeandP), factorized standard deviation of mean amplitude of a time sequence window (fTS.MeandP_STD),
factorized mean latency of a time sequence window (fTS.MeandT),
factorized standard deviation of mean latency of a time sequence window (fTS.MeandT_STD),
factorized mean rise time coefficient of a time sequence window (fTS.MeanRT),
factorized standard deviation of mean rise time coefficient of a time sequence window (fTS.MeanRT_STD),
factorized mean wave duration of a time sequence window (fTS.MeanWD),
factorized standard deviation of mean wave duration of a time sequence window (fTS.MeanWD_STD),
factorized mean single wave pressure of a time sequence window (fTS.Mean$_{SW}$P),
factorized standard deviation of mean single wave pressure of a time sequence window (fTS.Mean$_{SW}$P_STD),
factorized mean value of diastolic minimum pressure difference of a time sequence window (fTS.MeanDiff_P$_{min}$),
factorized standard deviation of mean value of diastolic minimum pressure difference of a time sequence window (fTS.MeanDiff_P$_{min}$_STD),
factorized mean value of systolic maximum pressure difference of a time sequence window (fTS.MeanDiff_P$_{max}$),
factorized standard deviation of mean value of systolic maximum pressure difference of a time sequence window (fTS.MeanDiff_P$_{max}$_STD),
factorized mean amplitude difference of a time sequence window (fTS.MeanDiff_dP),
factorized standard deviation of mean amplitude difference of a time sequence window (fTS.MeanDiff_dP_STD),
factorized mean latency difference of a time sequence window (fTS.MeanDiff_dT),
factorized standard deviation of mean latency difference of a time sequence window (fTS.MeanDiff_dT_STD),
factorized mean rise time coefficient difference of a time sequence window (fTS.MeanDiff_RT),
factorized standard deviation of mean rise time coefficient difference of a time sequence window (fTS.MeanDiff_RT_STD),
factorized mean wave duration difference of a time sequence window (fTS.MeanDiff_WD),
factorized standard deviation of mean wave duration difference of a time sequence window (fTS.MeanDiff_WD_STD),
factorized standard deviation of mean single wave pressure difference of a time sequence window (fTS.MeanDiff_Mean$_{SW}$P_STD),
factorized amplitude of the mean wave of a time sequence window (fTS.MeanWavedP),
factorized latency of the mean wave of a time sequence window (fTS.MeanWavedT), and
factorized rise time coefficient of the mean wave of a time sequence window (fTS.MeanWaveRT).

Said formula-based adjustment of time sequence (TS.x)-related parameters can be related to multiplication of the pressure scale of said individual time sequence windows of said pressure-related signal with a given constant factor value derived from the related time sequence (rTS.x) parameters. Said formula-based adjustment of time sequence (TS.x)-related parameters can also be related to adjustment of the pressure scale of said individual time sequence windows of said pressure-related signal according to a formula relationship derived from the related time sequence (rTS.x) parameters.

Reference is now given to FIGS. 10a, 10b, 10c, and 10d in order to further give details about analyzing simultaneous continuous pressure-related signals derived from different locations inside and/or outside of a body and/or body cavity, with determination of related time sequence (rTS.x) parameters, and using said related time sequence (rTS.x) parameters for creating factorized time sequence (fTS.x) parameters. FIG. 10 relates to simultaneous sampling of pressure-related signals derived from within the brain parenchyma (Signal[1]) and from the outer ear channel (Signal[2]) after air tight sealing of said outer ear channel.

Figure 10A:
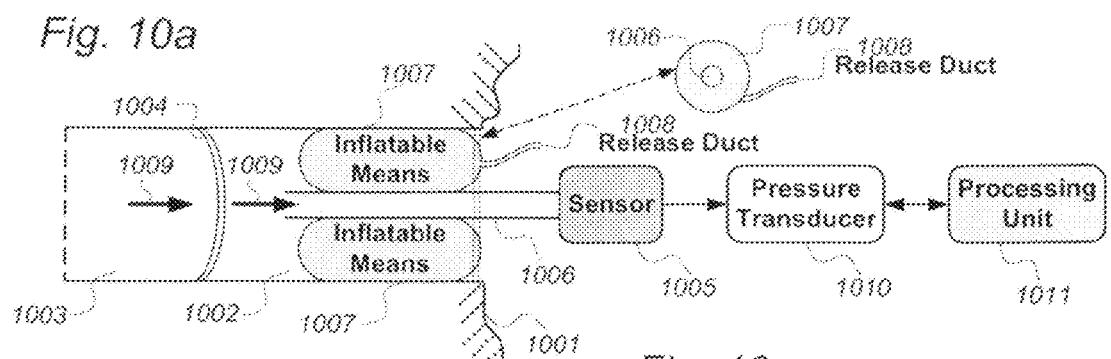
FIG. 10a shows a schematic drawing of a sensor detecting air pressure within the outer ear channel after airtight sealing by an inflatable balloon.

In paragraphs [270] to [272] is given reference to a fourth feature of this invention. Said fourth feature of the invention relates to a device for use in sensing continuous pressure-related signals through non-invasive pressure measurements on a human body, comprising a pressure sensor with a pressure sensing tube, said tube insertable into a human or animal outer ear channel spaced from a tympanic membrane thereof, and inflatable means surrounding an outside length of the tube, said inflatable means upon inflation thereof sealingly closing an annular gap between a region of said tube and a wall region of said outer ear channel. Reference is now given to FIG. 10a, showing in detail such a device for obtaining air pressure signals from within an airtight sealed outer ear channel. In FIG. 10a is shown a schematic presentation of an ear 1001, wherein ear skin surface forms the outer wall of the outer ear channel 1002 and the middle ear 1003, separated by the tympanic membrane 1004. Continuous pressure-related signals indicative of intracranial pressure are obtained by a sensor 1005 measuring air pressure within the outer ear channel 1002. A pressure sensing tube 1006 enables the sensor 1005 to be in contact with the closed air chamber within the outer ear channel 1002. This outer ear channel 1002 is closed by an inflatable means 1007 that is an inflatable thin walled balloon within the ear 1001 and the outer ear channel 1002, surrounding the pressure sensing tube 1006. Said inflatable balloon 1007 gives air tight sealing of the outer ear channel 1002 by being filled with fluid using a release duct 1008. Fluid could be e.g. air or water. Fluid filling of said inflatable balloon 1007 enables closing of the outer ear channel 1002. Thereby the air within the outer ear channel 1002 is separated from the atmospheric pressure. Pressure fluctuations are created by movement of the tympanic membrane 1004, since the tympanic membrane 1004 moves along with the pressure fluctuations within the middle ear 1003. The pressure gradient 1009 for each pressure wave is indicated with an arrow. Said inflatable means 1007 is deflatable by opening the release duct 1008, or by puncturing the inflatable means 1007. The non-invasive ear channel related sensor 1005 is connected via a signal transducer 1010 to a processing unit 1011, said processing unit 1011 being capable of delivering continuous pressure-related signals. It must be understood that said pressure sensor 1005 could be located anywhere along said pressure sensing tube 1006, said sensor 1005 location being within the ear channel 1002 or outside the ear channel 1002.

The significance of this device is that said inflatable means 1007 is thin-walled and soft, thus making airtight sealing of an outer ear channel 1002 possible, independent on the diameter of the outer ear channel 1002. Thereby one size of said sensor may be used independent of the diameter of the outer ear channel.

The opportunity to measure air pressure within the outer ear channel 1002 after airtight sealing of said channel 1002 is known in the prior art, based on the knowledge that is described in this paragraph. The intracranial pressure waves are transmitted via fluid pathways from the subarachnoid space to the perilymphatic duct (cochlear aqueduct). This pathway is the primary conduit between the subarachnoid space and the perilymphatic spaces, and is connected to the inner ear where the pressure waves cause motion of the oval (and round) window and the ossicles, leading to motion of the tympanic membrane 1004. If the outer ear channel 1002 is sealed in an airtight fashion, these motions of the tympanic membrane 1004 cause air-pressure fluctuations 1009 that can be recorded using a special sensor 1005.

Figure 10B:
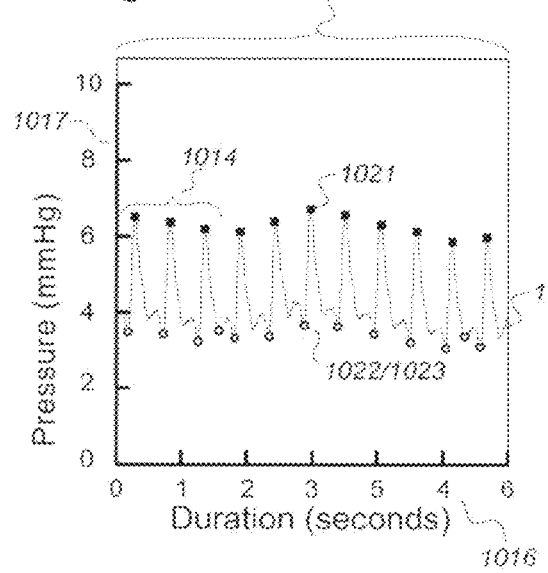
FIG. 10b shows one individual time sequence of a continuous pressure-related signal derived from the sensor placed within the brain parenchyma (Signal [1])
Figure 10C:
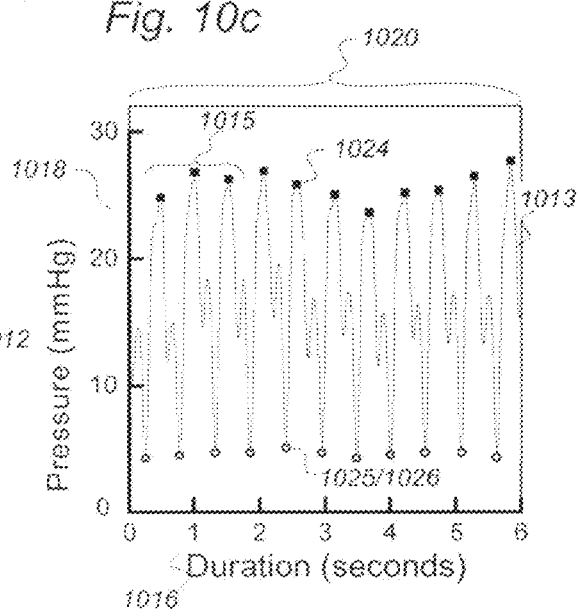
FIG. 10c shows the identical time sequence from a continuous pressure related signals derived from a sensor measuring air pressure within the closed outer air channel (Signal[2])

Reference is now given to FIGS. 10*b* and 10*c*, in order to illustrate processing of two simultaneous continuous pressure-related signals, in this case derived from within the brain parenchyma (Signal[1] 1012) and from the outer ear channel 1002 (Signal[2] 1013), as described in detail with reference to FIG. 10*a*. This particular example is taken from a test recording Recording[241]. It is shown single pressure waves 1014 of Signal[1] and single pressure waves of Signal[2] 1015. Both signals 1012, 1013 have identical time reference, indicated by identical time scale 1016 for both signals 1012, 1013. It is evident that the pressure scales of Signal[1] 1017 and Signal[2] 1018 are different with different scaling, related to the fact that said signals 1012, 1013 are measured with different sensors, having different characteristics. The time sequence window 1019 of Signal[1] and the time sequence window 1020 of Signal[2] are identical according to time and is referred to as Recording[241].Signal[1].Time Sequence[12] and Recording[241].Signal[2].Time Sequence[12]. Within said time sequence windows 1019, 1020 (Time Sequence[12] or TS[12]), single pressure waves 1014, 1015 related to cardiac beat-induced pressure waves within said two simultaneous signals 1012, 1013 are identified. With reference to FIG. 10*b*, it is indicated that included pair combinations of valleys and peaks in said signal 1012 are identified, corresponding to included pair combinations of a systolic maximum pressure value ($SW.P_{max}$) 1021 a diastolic minimum pressure value ($SW.P_{min1}$) 1022, characterizing single pressure waves 1014 created by the cardiac beat-induced pressure waves. Within this signal 1012 the ending diastolic minimum pressure ($SW.P_{min2}$) 1023 of a first single pressure wave was the same as starting diastolic minimum pressure ($SW.P_{min1}$) 1022 of the subsequent second single pressure wave. The systolic maximum pressures ($SW.P_{max}$) 1021 are indicated as filled squares, and the diastolic minimum pressures ($P_{min1}/P_{min2}$) 1022, 1023 are shown as open circles. With reference to FIG. 10*c*, it is as well indicated for Signal[2] 1013 the included pair combinations of a systolic maximum pressure value ($SW.P_{max}$) 1024 a diastolic minimum pressure value ($SW.P_{min1}$) 1025. Also for this fragment of the signal 1013, the ending diastolic minimum pressure ($SW.P_{min2}$) 1026 of a first single pressure wave was the same as starting diastolic minimum pressure ($SW.P_{min1}$) 1025 of the subsequent second single pressure wave. For each of said time sequence windows 1019, 1020 (Time Sequence[12]), were computed the time sequence (TS.x)-related parameters TS.MeandP and TS.MeanWavedP, as well as the related time sequence (rTS.x) parameters rTS.MeandP and rTS.MeanWavedP, as shown in Table 8.

TABLE 8

Data related to time sequence windows shown in FIGs. 10b and 10c.

Time sequence (TS.x)-related parameters

|  | TS.MeanWavedP | TS.MeandP |
|---|---|---|
| Signal[1] | 2.75 mmHg | 2.82 mmHg |
| Signal[2] | 20.7 mmHg | 21.46 mmHg |

TABLE 8-continued

Data related to time sequence windows shown in FIGs. 10b and 10c.

Related time sequence (rTS.x) values

| rTS.MeanWavedP | rTS.MeandP |
|---|---|
| 0.133 (=2.75/20.7) | 0.131 (=2.82/21.46) |

The recording incorporating Signal[1] 1012 and Signal[2] 1013 included a total of 500 time sequence windows (Time Sequence[1] to Time Sequence[500]) within each of said signals 1012, 1013 (Signal[1] and Signal[2]). The method for processing said signal 1012, 1013 illustrated by the Identifying Steps in FIG. 9 were applied said 500 time sequence windows, and only 40 time sequence windows [referred to as PerfectTimeSequences (PerfectTS)] were included since strict Single Wave & Delta Single Wave Criteria and Time Sequence & Delta Time Sequence Criteria were used. For these 40 included time sequence windows (PerfectTS) both the related time sequence (rTS.x) parameters rTS.MeanWavedP and rTS.MeandP were computed. The mean value of rTS.MeandP of said 40 time sequence windows was 0.126. This value was subsequently used for creating fTS.MeandP. This aspect of the method is further illustrated in FIG. 10*d*. The consecutive numbers of said 40 included time sequence windows (PerfectTS) are indicated on the x scale 1027. Pressure values are indicated on the y scale or pressure scale 1028. The trend plot of TS.MeandP 1029 of Signal[1] 1012 is indicated for said 40 included time sequence windows. In addition, the trend plot of fTS.MeandP 1030 of Signal[2] 1013 is indicated. Factorization of Signal[2] was performed by multiplying the parameter TS.MeandP of each individual of said 40 time sequence windows with the factor 0.126. When considering the trend plots in FIG. 10*d*, the mean value of all 40 time sequence windows of TS.MeandP 1029 of Signal[1] 1012 was 2.98±0.28 and the comparable mean value of mean fTS.MeandP 1030 of Signal[2] 1013 was 2.99±0.21. Thus, after factorization TS.MeandP of Signal[2] 1013 was nearly identical to TS.MeandP of Signal[1] 1012. Also the comparable fluctuations of TSMeandP 1029 and fTS.MeandP 1030 are shown in FIG. 10*d*.

Figure 10D:
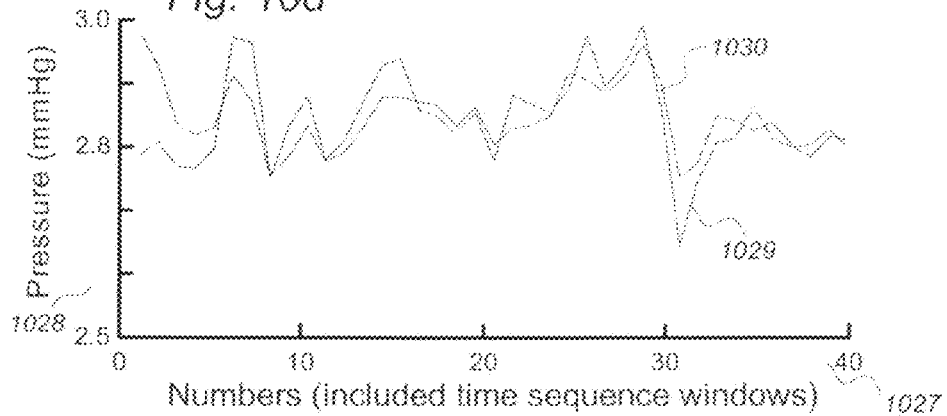
FIG. 10d shows trend plots of TS.MeandP of Signal[1] ad fTS.MeandP of Signal[2].

The data presented in FIGS. 10*b*, 10*c* and 10*d* provide illustrations that computation of related (rTS.x) and factorized (fTS.x) time sequence parameters can be very useful for non-invasive pressure measurements. This inventive feature provides a technical solution to this yet unsolved problem related to non-invasive pressure measurements.

Figure 11A:
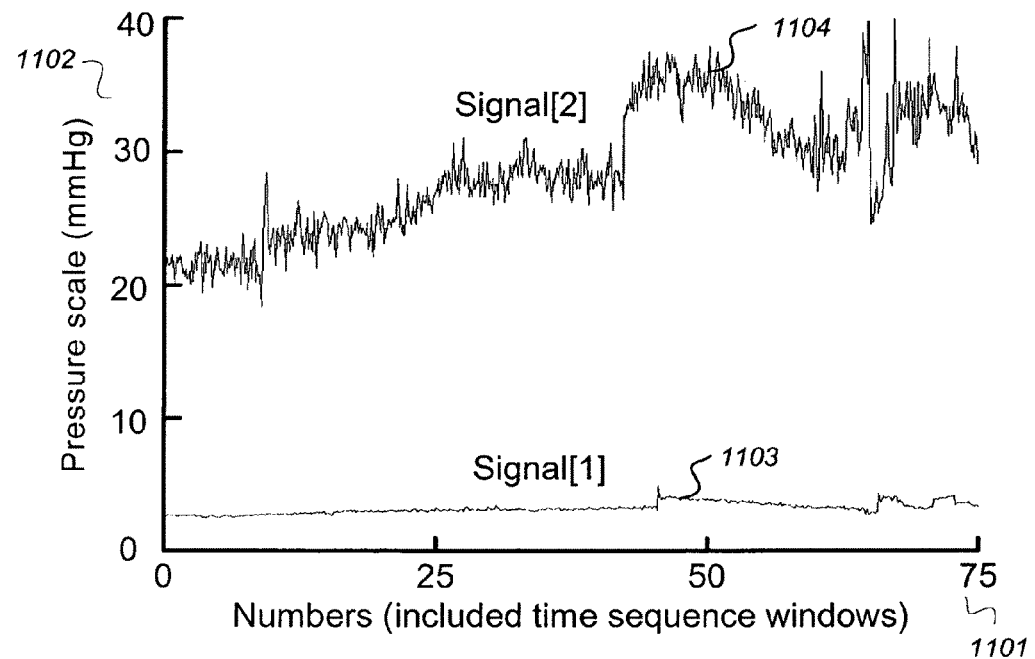
FIG. 11a shows trend plots of TS.MeandP of a continuous pressure-related signal derived from within the brain parenchyma and TS.MeandP of a continuous pressure-related signal derived from the outer ear channel after airtight sealing of the outer ear channel.
Figure 11B:
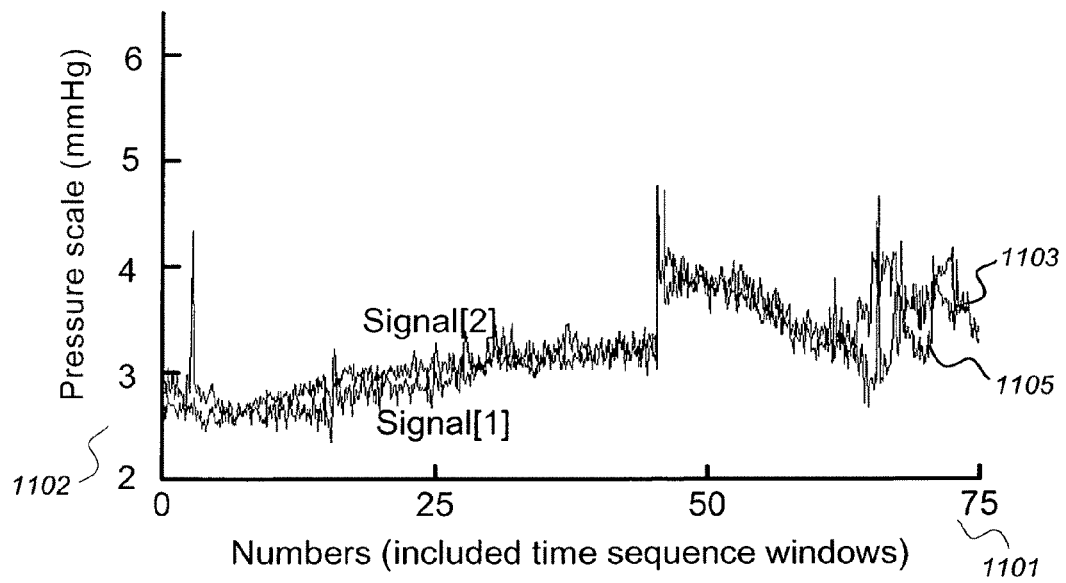
FIG. 11b shows trend plots of TS.MeandP and fTS.MeandP.

Reference is now given to FIGS. 11*a* and 11*b* that illustrate the same aspects as already described for FIGS. 10*a*, 10*b* and 10*c*. One individual recording contained two signals: Recording[250].Signal[1].ICP.Intradural; Recording[250].Signal [2].ICP.EarProbe. This means that both signals were continuous intracranial pressure (ICP)-related signals, wherein the sensor location was intra-dural (or within the brain parenchyma for Signal[1]) and non-invasive within the outer ear channel for Signal[2] within the same recording Recording [250]. The method of deriving continuous pressure-related signals indicative of intracranial pressure by measuring air pressure within the outer ear channel was described in detail for FIG. 10*a*. For the case referred to in FIGS. 11*a* and 11*b*, both Signal[1] and Signal[2] contained 3000 time sequence windows each (Time Sequence[1] to Time Sequence[3000]). The method described in detail for FIG. 9 was applied to both signals, leaving a total of 750 included and simultaneous time sequence windows within each of said two signals, i.e. 750 perfect time sequence windows (PerfectTS) were included. For both of said signals (Signal[1] and Signal[2]) the time sequence (TS.x) related parameter TS.MeandP were computed. Trend plots of TS.MeandP for these signals are shown in FIG. 11a, with numbers of consecutive included time sequence windows on the x scale 1101. The pressure scale 1102 is indicated on the y scale. Trend plot TS.MeandP 1103 of Signal[1] is indicated as well as trend plot TS.MeandP 1104 of Signal[2]. It is obvious that the y scaling of said two signals (Signal[1] and Signal[2]) are very different related to the fact that these signals were derived from different types of sensors and that the calibration of Signal[2] against atmospheric pressure was unknown. For each of these 750 simultaneous consecutive time sequence windows, the related time sequence (rTS.x) parameter rTS.MeandP was computed for each individual of said time sequence windows. The mean value of said 750 rTS.MeandP values was 0.137. Factorization of Signal[2] was performed by multiplying the parameter TS.MeandP of each individual of said 750 time sequences (PerfectTS) with the value 0.137, creating fTS.MeandP. The x scale 1101 is identical in FIGS. 11a and 11b. Concerning the y scale 1102, the scaling has been increased from in FIG. 11a to FIG. 11b. The trend plot of TS.MeandP 1103 of Signal [1] is indicated in FIG. 11b which is the same as signal 1103 in FIG. 11a. The trend plot of the factorized time sequence (fTS.x) parameter fTS.MeandP 1105 of Signal[2] (1104 in FIG. 11a) is as well shown in FIG. 11b. It should be noted that after factorization, the trend plots of TS.MeandP of 1103 Signal[1] and fTS.MeandP 1105 of Signal[2] followed each other closely, as clearly noted from FIG. 11b. When considering the trend plots in FIG. 11b, the mean value of all 750 time sequence windows (PerfectTS) of TS.MeandP 1103 of Signal[1] was 3.2±0.4 and the comparable mean value of mean fTS.MeandP 1105 of Signal[2] was 3.2±0.5. Thus, after factorization TS.MeandP of Signal[2] was practically identical to TS.MeandP of Signal[1]. Also the comparable fluctuations of TSMeandP 1103 and fTS.MeandP 1105 are shown in FIG. 11b.

The example shown in FIGS. 11a and 11b demonstrates that intracranial pressure (ICP) can be measured by placing a sensor within the outer ear channel. The basis for pressure signal processing is disclosed in connection with FIG. 9.

Both in FIGS. 10 and 11 two different simultaneous pressure-related signals were compared, wherein one signal (Signal[1]) was derived from within the brain parenchyma and the other signal (Signal[2]) was derived from within the outer ear channel (see FIG. 10a). In these examples Signal[1] may be considered as "gold standard" and Signal[2] as "non-gold" standard. Since the absolute zero pressure level is unknown for Signal[2], scaling of said pressure (y) scale is impossible. This is the problem with all types of non-invasive pressure monitoring, as related to currently used, prior art technology. Since the absolute pressure level relative to atmospheric pressure is unknown, continuous pressure-related signals derived from allocation on the body (i.e. non-invasively) only reveal changes in pressures without information whether the pressures are abnormal or not. By means of the present invention this problem is solved. The procedure is described exemplified by the locations (i.e. outer ear channel versus brain parenchyma) and sensors described for FIGS. 10 and 11:

i) Simultaneous signals from the same recordings are compared as described in detail for FIGS. 9, 10 and 11. Related time sequence (rTS.x) parameters are determined based on time sequence (TS.x)-related parameters only from included time sequence windows. The Single Wave & Delta Single Wave Criteria and Time Sequence & Delta Time Sequence Criteria used for identifying included time sequence windows (see FIG. 9) are very strict in order to exclude pressure waves related to artifacts or a combination of artifacts and cardiac beat-induced pressure waves. Strict criteria are used to ensure that the included single pressure waves of said included time sequence windows are single pressure waves related to cardiac beat-induced pressure waves. These included, i.e. accepted, time sequence windows are referred to as perfect time sequences (PerfectTS, or pTS).

ii) Related time sequence (rTS.x) parameters are determined for a population of recordings, and said relationships (rTS.x) may be stored in a database. The recordings may be categorized, e.g. related to signal type, locations and sensor types as well as physiological categorizations. Said related time sequence (rTS.x) parameters may be different types of relationships:

Constant relationships of rTS.x. Said related time sequence (rTS.x) parameters can be constant relationships between identical time sequence (TS.x)-related parameters of different pressure signals with identical time reference. This approach has been described in detail for rTS.MeandP (FIGS. 10b, 10c, 10d, 11a, and 11b), though rTS.x may be derived from any TS.x-related parameters.

Formula-based rTS.x relationships of related time sequences. Said related time sequence (rTS.x) parameters can be formula-based relationships between identical time sequence (TS.x)-related parameters of different pressure signals with identical time reference. Such formulas may be derived from a combination of time sequence (TS.x)- and related time sequence (rTS.x) parameters. The invention set no limitations concerning which formula-based relationships that are possible. Based on a population of recordings, determination of population-based formulas for said related time sequence (rTS.x)-related parameters is made possible.

iii) Said determined related time sequence (rTS.x) parameters are used for factorization of individual continuous pressure-related signals. Said factorization is particularly useful for non-invasive pressure-related signals. Said non-invasive signals are typically obtained without a simultaneous invasive signal. Said related relationships (rTS.x) stored in a database represent a historical material of known relationships that are used to factorize new and individual recordings. Some examples of continuous pressure-related signals that can be factorized according to this invention are mentioned: Continuous pressure-related signals indicative of intracranial pressure (ICP) may be derived from an invasive sensor measuring epidural pressure or from non-invasive sensors measuring air pressure within outer ear channel (as described for FIG. 10a), or transcranial Doppler signals, cranial impedance-related signals, cranial fontanel applanation pressure signals, or ocular applanation pressure signals. Continuous pressure-related signals indicative of arterial blood pressure may be derived from non-invasive sensors measuring arterial applanation pressure signals, pulse oxymetry signals, or from other physiological signals, being transformable into pressure-related signals indicative of intra-arterial pressure signals Reference is now given to a fifth feature of this invention. Characteristics of this inventive feature are particularly illustrated in FIGS. 12 and 13, and to FIG. 8.

Reference is now given to FIG. 12a. According to said fifth feature of this invention, it is described a device 1201 for use in draining excess fluid from a human brain or spinal fluid cavity 1202, comprising a first drainage tube 1203 having an inlet 1204 thereof located in said brain or spinal fluid cavity, said first drainage tube 1203 connected to the inlet 1205 of a fluid flow controllable valve 1206, a valve-opening regulator 1207 with associated control unit 1208 being connected to a regulator 1209 and processing unit 1210, the control output from which is a function of pressure-sensing signals derived from at least one pressure sensor 1211, a location of said sensor enabling continuous pressure-related signals to be derived from said human brain or spinal fluid cavity 1202, a pressure transducer 1212 transforming said pressure-sensing signals into signals processed by said processing unit 1210, a power supply 1213 connected thereto, information transferable means 1214, and a second drainage tube 1215 from an outlet 1216 of said valve opening having a distal outlet 1217 thereof, said distal outlet 1217 opening into said another human body cavity 1218. Said device 1201 including its components first drainage tube 1203, fluid flow controllable valve 1206, said valve-opening regulator 1207, said control unit 1208, said regulator 1209, said processing unit 1210, said pressure transducer 1212, said power supply 1213, said information transferable means 1214 and said second drainage tube 1215 being located below a skin surface of said human body.

In a xy-chart shown in FIG. 12*b*, it is indicated on the y-axis increasing valve opening 1219 and on the x-axis increasing fluid flow rate 1220, and a line 1221 indicates the relationship between degrees of valve opening 1219 and fluid flow rate 1220. This is shown to illustrate the fluid flow rate 1220 through said fluid flow controllable valve 1206 changes with increasing valve opening 1219 of said valve 1206. A specific type of relationship 1221 between valve opening 1219 and fluid flow rate 1220 represents no limitation of the scope of the invention, neither is a specific type of valve opening a limitation of the scope of the invention.

Said inlet 1204 of said first drainage tube 1203 can be located inside dura mater of a brain, within one or more of said brain fluid cavities. Typical locations can be within one of the cerebral ventricles within cerebrospinal fluid (CSF) compartments. Thereby the first drainage tube 1203 is able to drain fluid from said brain fluid cavities to the inlet 1205 of said fluid flow controllable valve 1206. Said 1204 inlet of a first drainage tube 1203 can as well be located inside dura mater of a spinal cord within the cerebrospinal fluid (CSF) cavity at the spinal level. Normally the cerebral and spinal cerebrospinal fluid (CSF) compartments are in direct communication, though blockade of fluid pathways may be present anywhere along the cranio-spinal fluid pathways. By placement of said first drainage tube 1203 within a spinal cerebrospinal fluid (CSF) compartment, said first drainage tube 1203 is able to drain fluid from said spinal fluid cavity 1202 to the inlet 1204 of said fluid flow controllable valve 1206.

A location of said sensor 1211 provides for sensing pressure-related signals from said human brain or spinal fluid cavity 1202. Said sensor 1211 location can be on or coupled to said first drainage tube 1203 providing for sensing pressure-related signals from said fluid within said first drainage tube 1203. For example, a sensor 1211 can be located on the tip of a ventricular catheter, e.g. first drainage tube 1203, placed within said cerebral ventricles. The connection wire between said sensor 1211 and pressure transducer 1212 that is incorporated within said device 1201 can be incorporated within the first drainage tube 1203. This would be the preferable approach though a placement of a sensor 1211 elsewhere than together with said first drainage tube 1203 is possible. Typically said sensor 1211 location is in a region of said brain cavity or in a region of said spinal cavity.

The sensor 1211 is connected via a signal transducer 1212 to said processing unit 1210, said processing unit 1210 is capable of delivering a first control signal to said regulator 1209. The output of said processing unit 1210 is set to control said control unit 1208 associated with said valve-opening regulator 1207, said control unit 1208 controlling fluid flow mass rate 1220 through said valve 1206 associated with said valve-opening regulator 1207 determining valve opening level 1219. The processing unit 1210 delivers a first control signal to said regulator 1209, and said regulator 1209 delivers a second control signal unto a control unit 1208, wherein the function of said second control signal is a function of said first control signal. The second control signal delivered unto said control unit 1208 is able to modify the mode by which said control unit 1208 controls adjustment of said valve-opening regulator 1207. The fluid flow rate 1220 through said valve 1206 is adjustable by said valve-opening regulator 1207 being controlled by said first control signal from said processing unit 1210.

Said device 1201 comprising partly said first drainage tube 1203, said fluid flow controllable valve 1206, said valve-opening regulator 1207, said control unit 1208, said regulator 1209, said processing unit 1210, said pressure transducer 1212, said power supply 1213, said information transferable means 1214 and partly said second drainage tube 1215 are locatable below a skin surface of said human body in a thoracic or abdominal body area. The device 1201 may thus be implanted in the thoracic area as is conventionally done for a cardiac pacemaker Another body cavity 1218 may be a thoracic body cavity such as a heart cavity, abdominal body cavity such as an intra-peritoneal cavity. The opening 1217 of said second drainage tube 1215 within said another body cavity 1218 enables drainage of fluid into an abdominal or thoracic body cavity 1218. Thereby fluid may be drained from said brain or spinal fluid body cavity 1202 into a thoracic or abdominal body cavity 1218.

The device incorporates information transferable means 1214 that provides for information transferal through skin between said information transferable means 1214 and an external processing unit 1222. Typically said external processing unit 1222 is placed on the skin surface above and in distance from the information transferable means 1214. Thus intact skin is between said information transferable means 1214 and an external processing unit 1222. Communication and transferal of information is performed wireless using technology known in the prior art. Said information can be from said power supply 1213 relating to residual power. It will be useful to record the residual battery supply to plan replacement of battery or recharging of battery if a rechargeable battery is used. Information can be derived from said processing unit 1210 relating to analysis output of processing of continuous pressure related signals. Continuous pressure-related signals are processed according to the method of this invention, and said external processing unit 1222 may read pressure recordings of a variable length. It can also be possible to deliver information from said external processing unit 1222 to the processing unit 1210 incorporated in said device 1201. This information can relate to adjustment of interaction between analysis output of said processing unit 1210 and the level of said first control signal delivered thereof.

In short, the function of said device 1201 incorporates the following steps:

(1) Continuous pressure sensing signals derived from said brain or spinal fluid cavity 1202 are transferred from said sensor 1211 to said pressure transducer 1212, modifying said signals into signals that can be further processed by the processing unit 1210.

Figure 14:
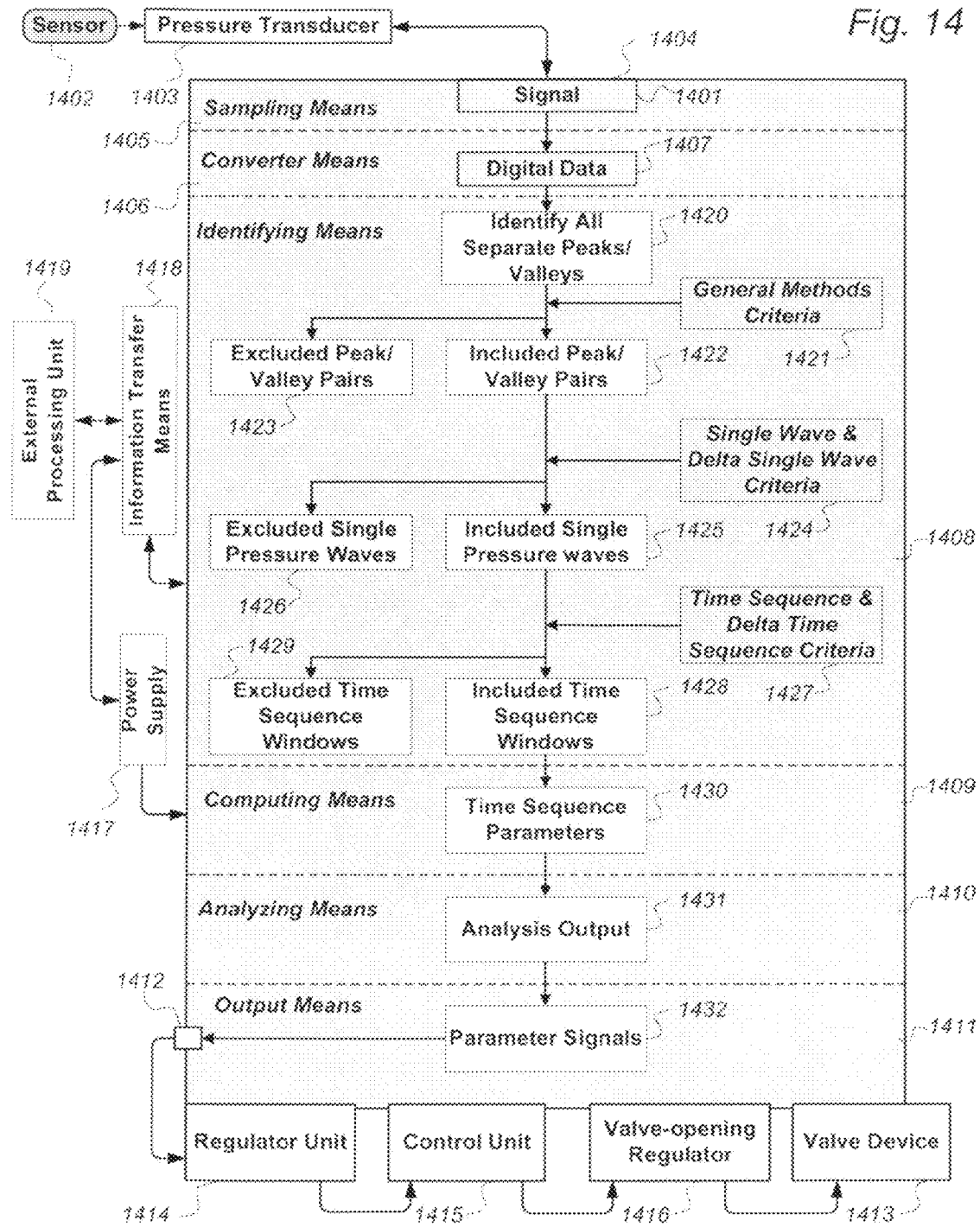
FIG. 14 shows a flow chart over a system for processing continuous pressure-related signals, used for control of drainage fluid flow rate from a first to a second body cavity.

(2) The inventive method for processing continuous pressure-related signals described in detail for FIG. 8 is applied to a selectable duration of said pressure signal. An analysis output is created based on computation of time sequence parameters (see FIG. 8). The method for processing of continuous pressure-related signals with reference to said device 1201 is further described in detail with reference to FIGS. 13 and 14.

(3) Based on said analysis output of said processing unit 1210, a first control signal is created and delivered into said regulator 1209. Said first control signal is a function of said analysis output. This step is further described in detail with reference to FIG. 14.

(4) Within said regulator 1209 said first control signal is transformed unto a second control signal that is delivered unto a control unit 1208 that is modifying the mode by which a valve opening regulator 1207 is functioning. Said valve-opening regulator modifies the valve opening level 1219 that in turn determines the fluid flow rate 1220 of said fluid flow controllable valve 1206.

(5) The whole process is tuned in so that said analysis output of said processing unit 1210 determines and controls the fluid flow rate 1220 of said valve 1206.

It should be understood that modifications of said components and modifications of functional interactions between said components are within the scope of this invention. A crucial aspect of the invention is that valve opening level 1219 and hence fluid flow rate 1220 can be determined from said analysis output of said processing unit 1210, wherein said analysis output is determined by the inventive method of processing continuous pressure-related signals. A further crucial aspect of the invention is the possibility of being able to locate the device 1201 in the thoracic area of the body, providing a greater freedom of construction of the device, and easier maintenance, repair and replacement of components.

As compared to current and prior art technology, the device has several major advantages, such as e.g.: (a) Optimal and physiological drainage of fluid is made possible. Optimal drainage is obtained when fluid drainage is accompanied with normal cerebral compliance. The inventive method when incorporated within said processing unit in the inventive device or the inventive system enables control of drainage to a rate giving optimal cerebral compliance. (b) Current problems associated with drainage such as over-drainage or under-drainage are eliminated. The inventive method when used in a processing unit of the inventive device or the inventive system reveals too high or too low pressure and enables the device or the system to provide an output to adjust valve fluid flow rate thereafter. (c) Optimal placement of device. Since valve fluid flow rate is independent of the position of the patient, the device may be placed the most optimal location for the particular case. For example, the device may be placed below the skin in the thoracic level, comparable to a conventional pacemaker placement. (d) Physiological drainage from either brain or spinal fluid cavities. Since the inventive device or system processes pressure signals independent of a zero pressure level and also enables continuous pressure signals from spinal cerebrospinal fluid cavity when processed in the device or system to be highly predictive of intracranial pressure, when using the device or system the distal end of the first drainage tube can be placed within the spinal cerebrospinal fluid (CSF) cavity, making it unnecessary to penetrate the brain with a catheter.

Reference is now given to the sixth feature of this invention. Various aspects related to this feature of the invention are particularly shown in FIG. 8, and also in connection with FIGS. 13 and 14.

This sixth inventive feature relates to a method for processing continuous pressure-related signals, as related to the use of said device 1201. Pressure sensing signals are derived from said sensor 1211, and modified within said pressure transducer 1212 into signals that are further within said processing unit 1210. The process method has already been described in detail with reference to FIG. 8, and partly with reference to FIG. 2. Said method for processing continuous pressure-related signals derived from locations inside a human body or body cavity, comprises the steps of obtaining samples of said signals at specific intervals, and converting thus sampled pressure signals into pressure-related digital data with a time reference. For selectable time sequence windows the method comprises the further steps of identifying from said digital data signal single pressure waves related to cardiac beat-induced pressure waves, and identifying from said digital data signal pressure waves related to artifacts or a combination of artifacts and cardiac beat-induced pressure waves. The different steps of this process are reviewed in the Identifying Steps of FIG. 8. The method for processing the pressure-related signals further incorporates computing time sequence (TS.x)-related parameters of said single pressure waves during individual of said included time sequence windows (Computing Step; FIG. 8), and establishing an analysis output of said time sequence (TS.x)-related parameters for a selectable number of said time sequence windows. For included time sequence windows said analysis output relates to computing time sequence (TS.x)-related parameters, said parameters selected from the group of:

mean value of starting diastolic minimum pressures of a time sequence window (TS.MeanP$_{min1}$), standard deviation of mean value of starting diastolic minimum pressures of a time sequence window (TS.MeanP$_{min1}$_STD), mean value of systolic maximum pressures of a time sequence window (TS.MeanP$_{max}$), standard deviation of mean value of systolic maximum pressures of a time sequence window (TS.MeanP$_{max}$_STD), mean amplitude of a time sequence window (TS.MeandP), standard deviation of mean amplitude of a time sequence window (TS.MeandP_STD), mean latency of a time sequence window (TS.MeandT), standard deviation of mean latency of a time sequence window (TS.MeandT_STD), mean rise time coefficient of a time sequence window (TS.MeanRT), standard deviation of mean rise time coefficient of a time sequence window (TS.MeanRT_STD), mean wave duration of a time sequence window (TS.MeanWD), standard deviation of mean wave duration of a time sequence window (TS.MeanWD_STD), mean single wave pressure of a time sequence window (TS.Mean$_{SW}$P), standard deviation of mean single wave pressure of a time sequence window (TS.Mean$_{SW}$P_STD), mean of diastolic minimum pressure differences of a time sequence window (TS.MeanDiff_P$_{min}$), standard deviation of mean of diastolic minimum pressure differences of a time sequence window (TS.MeanDiff_P$_{min}$_STD), mean of systolic maximum pressure differences of a time sequence window (TS.MeanDiff_$P_{max}$), standard deviation of mean of systolic maximum pressure differences of a time sequence window (TS.MeanDiff_$P_{max}$_STD), mean amplitude difference of a time sequence window (TS.MeanDiff_dP), standard deviation of mean amplitude difference of a time sequence window (TS.MeanDiff_dP_STD), mean latency difference of a time sequence window (TS.MeanDiff_dT), standard deviation of mean latency difference of a time sequence window (TS.MeanDiff_dT_STD), mean rise time coefficient difference of a time sequence window (TS.MeanDiff_RT), standard deviation of mean rise time coefficient difference of a time sequence window (TS.MeanDiff_RT_STD), mean wave duration difference of a time sequence window (TS.MeanDiff_WD), standard deviation of mean wave duration difference of a time sequence window (TS.MeanDiff_WD_STD), mean single wave pressure difference of a time sequence window (TS.MeanDiff_Mean$_{SW}$P), standard deviation of mean single wave pressure difference of a time sequence window (TS.MeanDiff_Mean$_{SW}$P_STD), numbers of accepted single pressure waves of a time sequence window (TS.SWCount), mean wave amplitude of a time sequence computed according to the first matrix (TS.MeanWavedP), mean wave latency of a time sequence computed according to the first matrix (TS.MeanWavedT), mean wave rise time coefficient of a time sequence computed according to the second matrix (TS.MeanWaveRT).

The methods for computing said parameters have already been described in detail with reference to FIGS. 2 and 8. Any of said time sequence (TS.x)-related parameters can be used to create said analysis output. Concerning regulation of said valve opening level 1219 and fluid flow rate 1220, in a preferred mode of the invention it has been found that the following parameters are most useful: Mean wave amplitude (TS.MeanWavedP), mean wave latency (TS.MeanWavedT), mean wave rise time coefficient (TS.MeanWaveRT), and mean amplitude (TS.MeandP), mean latency (TS.MeandT), and mean rise time coefficient (TS.MeanRT). However, other parameters as mentioned could also be used in addition or as replacements.

The various time sequence (TS.x)-related parameters have a different role in regulation of a valve, such as e.g.:

(a) Quality control that the continuous pressure signal is of good quality (i.e. that time sequence windows included for analysis contain single pressure waves created by cardiac beat-induced pressure waves) is predicted by TS-parameters such as: TS.MeandT, TS.MeandT_STD, TS.MeanWD, TS.MeanWD_STD, TS.MeanDiff_dT, TS.MeanDiff_dT_STD, TS.MeanDiff_WD, TS.MeanDiff_WD_STD, TS.SWCount, and TS.MeanWavedT. In particular, it is useful to combine values of several of said parameters.

(b) Determination of reduced or increased cerebral compliance (i.e. whether intracranial pressure (ICP) is abnormally high or low) is predicted by TS-parameters such as: TS.MeandP, TS.MeandP_STD, TS.MeanRT, TS.MeanRT_STD, TS.MeanDiff_dP, TS.MeanDiff_dP_STD, TS.MeanWavedP, and TS.MeanWaveRT. It can be very useful to combine the values of several of these parameters. This particular aspect is described in connection with FIGS. 13a and 13b, including the parameters TS.MeanWavedP and TS.MeanWavedT. In FIG. 13a is as well illustrated that changes in cerebral compliance can not be revealed by current and prior art technology (illustrated by the TS-parameter TS.MeanICP that is computed according to prior art technology).

(c) Prediction of absolute intracranial pressure (ICP) (i.e. absolute pressure relative to atmospheric pressure) is made by TS-parameters such as: TS.MeanP$_{min1}$, TS.MeanP$_{min1}$_STD, TS.MeanP$_{max}$, TS.MeanP$_{max}$_STD, TS.MeandP, TS.MeandP_STD, TS.MeanRT, TS.MeanRT_STD, TS.Mean$_{SW}$P, TS.Mean$_{SW}$P_STD, TS.MeanDiff_$P_{min}$, TS.MeanDiff_$P_{min}$_STD, TS.MeanDiff_$P_{max}$, TS.MeanDiff_$P_{max}$_STD, TS.MeanDiff_dP, TS.MeanDiff_dP_STD, TS.MeanDiff_RT, TS.MeanDiff_RT_STD, TS.MeanDiff_Mean$_{SW}$P, TS.MeanDiff_Mean$_{SW}$P_STD, TS.MeanWavedP, and TS.MeanWaveRT. Values of these different TS-parameters are combined to predict absolute intracranial pressure (ICP).

Based on said analysis output, a deliverable first control signal is established, said first control signal being determined according to one or more selectable criteria for said analysis output. Subsequently said first control signal is modified within said regulator 1209 into a second control signal. Said second control signal is a function of said first deliverable control signal, and is applicable as a device performance-modifying signal. Within said device 1201, said device performance-modifying signal can modify a valve opening regulator 1207, controlling a shunt-valve fluid flow rate 1220.

Said selectable criteria are determined on basis of analysis output of a selectable number of individual time sequence windows in a continuous series of said time sequence windows. For example, said selectable criteria relate to selectable thresholds for time sequence (TS.x)-related parameters, said parameters selected from the group of: mean wave amplitude (TS.MeanWavedP), mean wave latency (TS.MeanWavedT), mean wave rise time coefficient (TS.MeanWaveRT), mean amplitude (TS.MeandP), mean latency (TS.MeandT), and mean rise time coefficient (TS.MeanRT). Exact thresholds for said time sequence (TS.x)-related parameters are not given, not to limit the scope of the invention. However, in order to illustrate aspects with such selectable criteria, an example of criteria related to TS.MeanWavedP is shown in Table 9.

TABLE 9

Selectable criteria related to TS.MeanWavedP.

| TS.MeanWavedP Thresholds* | Processing Unit: Analysis Output — First Control Signal Level | Processing Unit: Performance Output — Valve Opening Level | Processing Unit: Performance Output — Valve Fluid Flow Rate Level |
|---|---|---|---|
| 1.0-3.0 mmHg | 0 | 0 | 0 |
| 3.0-4.0 mmHg | 1 | 1 | 1 |
| 4.0-5.0 mmHg | 2 | 2 | 2 |
| 5.0-7.0 mmHg | 3 | 3 | 3 |
| >7.0 mmHg | 4 | 4 | 4 |

*TS.MeanWave dP Threshold relates to a mean value of mean wave amplitude (TS.MeanWavedP) for a selectable number of said individual time sequence windows.

In this specific example, said deliverable first control signal from said processing unit 1210 unto said regulator 1209 has five levels; at First Control Signal Level zero, the corresponding Valve Opening Level is zero, the corresponding Valve Fluid Flow Rate Level is zero, corresponding to no flow of fluid through said valve 1206. On the other hand, at First Control Signal Level four, the corresponding Valve Opening Level is four, the corresponding Valve Fluid Flow Rate Level is four, corresponding to maximum flow of fluid through said valve 1206. Thresholds of said time sequence (TS.x)-related parameters may be related to individual of said parameters or to combinations of said parameters. The first and second control signal levels may be possible to adjust according to said criteria. The specific levels referred to in Table 8 should not limit the scope of the invention.

Reference is now given to FIGS. 13a, 13b, and 13c in order to further illustrate how the results of the inventive method of processing pressure-related signals can be used to modify a shunt valve opening level.

First the background of the example is explained. A woman with so-called normal-pressure hydrocephalus (NPH) received a Codman-HAKIM™ adjustable shunt. This shunt consists of the following components, as related to the device shown in FIG. 12a: A ventricular catheter (corresponding to the first drainage tube 1203) was placed within the cerebral ventricles (corresponding to the first brain fluid cavity 1201), and connected to the shunt valve (corresponding to the fluid flow adjustable valve 1206). This shunt valve (1206) then was connected to a distal catheter (corresponding to the second drainage tube 1215) that was introduced to the intra-peritoneal cavity (corresponding to another body cavity 1218). The shunt contained an adjustable fluid flow controllable valve. The system was placed below the skin of this woman. By applying a regulator onto the intact skin surface, the fluid flow of said valve could be adjusted. The shunt function is well known from the prior art and not described in more detail here.

With reference to FIGS. 13a, 13b and 13c is shown three periods of pressure measurement, with the time scale 1301 on the x-axis. For the first pressure measurement the adjustable valve was adjusted to 16 cm $H_2O$, for the second pressure recording the valve resistance was 12 cm $H_2O$ and for the third time period the valve resistance was 8 cm $H_2O$. The terms 16 cm $H_2O$, 12 cm $H_2O$ and 8 cm $H_2O$ refer to different degrees of valve opening, with increased valve opening the lower resistance applied. The mechanism by which an adjustable vale is draining fluid is not a part of this invention and is not described in more detail. In this case a Codman ICP sensor was placed within the brain parenchyma, thus enabling the simultaneous ICP recording. The sensor is tunneled outside the skin, connected to an external pressure transducer (Codman ICP Express), and analyzed according to the method described in this invention. The y-axis of FIG. 13a indicates the pressure scale 1302 of mean intracranial pressure (ICP) computed according to current and existing technology. The trend plot 1303 of mean ICP is also indicated. It must be remembered that mean ICP is computed according to currently used, prior art technology as the sum of pressure levels divided by number of samples, independent whether the signal contains pressure waves related to cardiac beats or artifacts. It is clearly shown that mean ICP did not change during adjustment of shunt valve opening. On the other hand, highly observable changes were found for the trend plots of the TS.x-parameters TS.MeanWavedP 1305 and TS.MeanWavedT 1307 that are computed according to the inventive method. Both these latter parameters are highly indicative of intracranial compliance.

In FIG. 13b is indicated the pressure scale 1304 of TS.MeanWavedP with the trend plot of TS.MeanWavedP 1305. In FIG. 13c is shown on the Y-axis the TS.MeanWavedT scale 1306 as well as the trend plot of TS.MeanWavedT 1307. Valve opening level 1308 was 16 cm $H_2O$ before the first measurement period 1309, valve opening level 1310 was 12 cm $H_2O$ before the second measurement period 1311, and valve opening level 1312 was 8 cm $H_2O$ before the third measurement period 1313. It should be noted that though valve resistance was reduced, mean ICP (computed according to current and prior art technology and not a part of this invention) did not change much between the measurement periods one 1309 to three 1313 (mean ICP 10.5±3.0 mmHg for measurement period one, mean of trend plot of mean ICP 7.6±3.3 mmHg for measurement period two, and mean ICP 8.9±3.6 mmHg for measurement period three). Therefore, mean ICP was within normal ranges during all the three measurement periods, and currently used, prior art methods for evaluating pressure changes were of no help. Mean wave amplitude (TS.MeanWavedP) 1305, on the other hand, changed during adjustment of the shunt (mean wave amplitude 4.7±1.6 mmHg for measurement period one, mean wave amplitude 3.6±1.0 mmHg for measurement period two, and mean wave amplitude 3.2±0.5 mmHg for measurement period three). In test recordings, it has already been established that the presence of mean wave amplitudes (TS.MeanWavedP) above 4.5 mmHg is abnormal, and highly predictable for a good response to extra-cranial shunt treatment. Therefore, during shunt adjustment mean wave amplitudes (TS.MeanWavedP) were normalized. It should also be noted that mean wave latency (TS.MeanWavedT) values were as well normalized during shunt valve adjustment (mean wave latency 0.26±0.04 seconds for measurement period one, mean wave latency 0.24±0.05 seconds for measurement period two, and mean wave latency 0.21±0.04 seconds for measurement period three). The down-regulation of shunt valve resistance was accompanied by a clinical improvement of the patient.

With reference to Table 9, this specific example illustrates the following: After measuring mean wave amplitudes (TS.MeanWavedP) above 4.5 mmHg for a selectable time (e.g. said first measurement period 1309; FIG. 3b), said First Control Signal Level would be adjusted to level 2, corresponding to a Valve Opening Level 2 and a Valve Fluid Flow Rate Level 2. After a new measurement period of a selectable time (e.g. said second measurement period 1311; FIG. 13b) measuring mean wave amplitudes (TS.MeanWavedP) between 3 and 3.5 mmHg, said First Control Signal Level would remain at 1, corresponding to a Valve Opening Level remaining at 1 and a Valve Fluid Flow Rate Level remaining at 1. The duration of pressure measurement is selectable. By means of this approach the inventive device 1201 would ensure best possible drainage of excess fluid within said brain or spinal fluid cavities.

Reference is now given to the seventh feature of this invention. Characteristics related to this feature of the invention are particularly shown in FIG. 14, and also in connection with FIG. 8.

According to said seventh feature of this invention is described a system for processing continuous pressure-related signals 1401 derivable from one or more sensor(s) 1402 having location(s) inside or outside a body or body cavity of a human being. Said system comprises means for on basis of said signals 1401 receivable from said sensor(s) 1402 via pressure transducer means 1403 to control drainage fluid flow rate from a first body cavity to a second body cavity in one said human. A processing device 1404 in said system has means for processing said signals 1401, said processing means including sampling means 1405 for sampling said signals 1401 at specific intervals, converter means 1406 for converting the sampled signals 1401 into pressure related digital data 1407 with a time reference, identifying means 1408 for during selectable time sequence windows identifying from said digital data 1407 single pressure waves related to cardiac beat-induced pressure waves, and related to artifacts or a combination of cardiac beat-induced waves and artifacts, means for computing 1409 and analyzing 1410 said digital data 1407 during said selectable time sequence windows, output means 1411 for outputting to device terminal means 1412 one or more pressure parameter signals related to a selectable number of said time sequence windows, such as preferably mean wave amplitude (TS.MeanWavedP), mean wave latency (TS.MeanWavedT), mean wave rise time coefficient (TS.MeanWaveRT), mean amplitude (TS.MeandP), mean latency (TS.MeandT), mean rise time coefficient (TS.MeanRT), and mean single wave pressure (TS.Mean$_{SW}$P). The system includes a valve device 1413 controlling the drainage fluid flow rate and connectable to said body cavities. A regulator unit means 1414 connectable to said terminal means 1412 for receiving at least one of said parameter signals, said regulator unit means 1414 being capable of establishing a device performance modifying signal by means of one of said pressure parameter signals or a combination effect obtained from using at least two of said pressure parameter signals, wherein said performance modifying signal deliverable from said regulator unit 1414 is capable of controlling said drainage fluid flow rate through said valve device 1413 by input to a control unit 1415 and therefrom to a valve-opening regulator 1416. Said performance modifying signal is a function of pressure parameter signals, said function being related to selectable criteria for said pressure parameter signals.

The system incorporates a power supply 1417 locatable below skin surface of said human being and incorporates transfer means 1418 enabling information transfer through skin of said human being, said information being deliverable to an external processing unit 1419, said information including one or more of power supply 1417 power status, valve device 1413 performance data, parameter signals available or used.

It should be understood that modifications of said components and modifications of functional interactions between said components are within the scope of this invention.

The location of said sensor 1402 provides for sensing pressure-related signals 1401 from either a brain body cavity or a spinal body cavity. Drainage of fluid flow rate is from a first body cavity to a second body cavity in one said human, and said first body cavity can be a brain or spinal body cavity, said second body cavity relates to a thoracic body cavity or an abdominal body cavity.

Location of a valve device between first and second body cavities is appreciated from studying the schematic drawing figure of FIG. 12a. The system is locatable below a skin surface of said human body in a thoracic or abdominal body area.

Said processing device 1404 in said system provides for processing said signals 1401 according to the method described for FIGS. 2 and 8. With reference to previous descriptions related to FIGS. 2 and 8, a short overview of the inventive system for processing of continuous pressure signals 1401 is now given with reference to FIG. 14.

The identifying means 1408 the method provides for identification of all separate peaks and valleys 1420 in said sampled signal 1401. Each of said peaks is a sample with a pressure value and a time stamp or location, and each of said valleys is a sample with a pressure value and a time stamp or location. The result of applying General Methods Criteria 1421 is either included peak/valley pair combinations 1422 or excluded peak/valley pair combinations 1423.

After applying the Single Wave & Delta Single Wave Criteria 1424 to said included peak/valley pairs 1422, the output is either included single pressure waves 1425 or excluded pressure waves 1426. Said criteria 1424 relate to thresholds and ranges of single pressure wave (SW.x)-related parameters and delta single pressure wave (ΔSW.x)-related parameters during time sequence windows.

After applying the Single Wave & Delta Single Wave Criteria 1424, included pair combinations of peak/valley pairs 1422 in said signal 1401 correspond to included single pressure waves 1425. Pair combinations of diastolic minimum pressure (SW.P$_{min1}$) and systolic maximum pressure (SW.P$_{max}$) characterize single pressure waves created by cardiac beat-induced pressure waves. Said criteria 1424 exclude for further analysis pressure waves (i.e. minimum-maximum pressure (SW.P$_{min1}$/SW.P$_{max}$) pairs) during said time sequence windows with said single pressure wave (SW.x)- and delta single pressure wave (ΔSW.x)-related parameters outside selected criteria for thresholds and ranges of said parameters. Said criteria 1424 include for further analysis single pressure waves 1425 having single pressure wave (SW.x)- and delta single pressure wave (ΔSW.x)-related parameters within selected criteria for thresholds and ranges of said single pressure wave (SW.x)-related parameters. Pair combinations of diastolic minimum pressure (SW.P$_{min1}$) and systolic maximum pressure (SW.P$_{max}$) correspond to diastolic minimum pressures and systolic maximum pressures of individual of pressure waves created by each of said cardiac beats.

In order to further evaluate the included single pressure waves 1425, Time Sequence & Delta Time Sequence Criteria 1427 are applied to each of said time sequence windows in a continuous series of said time sequence windows. Each time sequence window is a selected time frame of said signal 1401. Said criteria 1427 for thresholds and ranges of said time sequence (TS.x) and delta time sequence (ΔTS.x)-related parameters determine included, i.e. accepted, time sequence windows 1428 and excluded, i.e. rejected, time sequence windows 1429. Said criteria 1427 exclude for further analysis time sequence windows 1429 with time sequence (TS.x)- and delta time sequence (ΔTS.x)-related parameters outside selected criteria for thresholds and ranges of said parameters. Said criteria 1427 include for further analysis time sequence windows 1428 having time sequence (TS.x) and delta time sequence (ΔTS.x)-related parameters within selected criteria for thresholds and ranges of said time sequence (TS.x) and delta time sequence (ΔTS.x)-related parameters.

Using said computing means 1409, time sequence (TS.x)-related parameters 1430 are computed for each individual of said included time sequence windows 1428. Such procedure is applied to each of said included, i.e. accepted, time sequence windows 1428 in a continuous series of said time sequence windows. Using said computing means 1409, time sequence (TS.x)-related parameters 1430 from included time sequences windows 1428 are computed, said parameters can be selected from the group of:

mean value of starting diastolic minimum pressures of a time sequence window (TS.MeanP$_{min1}$), standard deviation of mean value of starting diastolic minimum pressures of a time sequence window (TS.MeanP$_{min1}$_STD), mean value of systolic maximum pressures of a time sequence window (TS.MeanP$_{max}$), standard deviation of mean value of systolic maximum pressures of a time sequence window (TS.MeanP$_{max\_}$STD), mean amplitude of a time sequence window (TS.MeandP), standard deviation of mean amplitude of a time sequence window (TS.MeandP_STD), mean latency of a time sequence window (TS.MeandT), standard deviation of mean latency of a time sequence window (TS.MeandT_STD), mean rise time coefficient of a time sequence window (TS.MeanRT), standard deviation of mean rise time coefficient of a time sequence window (TS.MeanRT_STD), mean wave duration of a time sequence window (TS.MeanWD), standard deviation of mean wave duration of a time sequence window (TS.MeanWD_STD), mean single wave pressure of a time sequence window (TS.Mean$_{SW}$P), standard deviation of mean single wave pressure of a time sequence window (TS.Mean$_{SW}$P_STD), mean of diastolic minimum pressure differences of a time sequence window (TS.MeanDiff_P$_{min}$), standard deviation of mean of diastolic minimum pressure differences of a time sequence window (TS.MeanDiff_P$_{min}$_STD), mean of systolic maximum pressure differences of a time sequence window (TS.MeanDiff_P$_{max}$), standard deviation of mean of systolic maximum pressure differences of a time sequence window (TS.MeanDiff_P$_{max}$_STD), mean amplitude difference of a time sequence window (TS.MeanDiff_dP), standard deviation of mean amplitude difference of a time sequence window (TS.MeanDiff_dP_STD), mean latency difference of a time sequence window (TS.MeanDiff_dT), standard deviation of mean latency difference of a time sequence window (TS.MeanDiff_dT_STD), mean rise time coefficient difference of a time sequence window (TS.MeanDiff_RT), standard deviation of mean rise time coefficient difference of a time sequence window (TS.MeanDiff_RT_STD), mean wave duration difference of a time sequence window (TS.MeanDiff_WD), standard deviation of mean wave duration difference of a time sequence window (TS.MeanDiff_WD_STD), mean single wave pressure difference of a time sequence window (TS.MeanDiff_Mean$_{SW}$P), standard deviation of mean single wave pressure difference of a time sequence window (TS.MeanDiff_Mean$_{SW}$P_STD), numbers of accepted single pressure waves of a time sequence window (TS.SWCount), mean wave amplitude of a time sequence window computed according to the first matrix (TS.MeanWavedP), mean wave latency of a time sequence window computed according to the first matrix (TS.MeanWavedT), mean wave rise time coefficient of a time sequence window computed according to the second matrix (TS.MeanWaveRT).

The methods for computing said parameters 1430 have already been described in detail with reference to FIGS. 2 and 8. Any of said time sequence (TS.x)-related parameters 1430 can be used to create said analysis output 1431 from an analysis means 1410. Concerning regulation of said valve 1413, in a preferred mode of the invention it has been found that the following parameters are most useful: Mean wave amplitude (TS.MeanWavedP), mean wave latency (TS.MeanWavedT), mean wave rise time coefficient (TS.MeanWaveRT), mean amplitude (TS.MeandP), mean latency (TS.MeandT), mean rise time coefficient (TS.MeanRT), and mean single wave pressure (TS.Mean$_{SW}$P).

There are several major advantages with computing one or more of said parameters:

a) Compliance within a brain or spinal body cavity can be assessed by parameters e.g. such as TS.MeanWavedP, TS.MeanWavedT, TS.MeanWaveRT, TS.MeandP, TS.MeandT, and (TS.MeanRT). This is not possible by currently used, prior art technology. The inventive system enables to control drainage of excess fluid in a way that ensures optimal cerebral compliance.

b) The quality of the pressure signals can be assessed by parameters, e.g. such as TS.MeanPmin1_STD, TS.MeanP$_{max}$_STD, TS.MeandP_STD, TS.MeandT_STD, TS.MeanRT_STD, TS.MeanWD_STD, TS.MeanDiff_P$_{min}$_STD, TS.MeanDiff_P$_{max}$_STD, TS.MeanDiff_dP_STD, TS.MeanDiff_dT_STD, TS.MeanDiff_RT_STD, and TS.MeanDiff_WD_STD. It is very important to quality control the signals since bad signal quality increases the risk of not identifying cardiac beat-induced single pressure waves. Such quality control is not possible with current, prior art technology.

c) The output of said identifying means 1408 is included time sequence windows 1428 wherein said time sequence windows are included the best possible way. This means that these time sequence windows 1428 contain single pressure waves related to cardiac beat-induced pressure waves, not to artifacts or a combination of artifacts and cardiac beat-induced pressure waves. Thereby the risk of computing false or misleading time sequence (TS.x)-related parameters is made minimal.

d) Combinations of said time sequence parameters 1430 provide more detailed information about compliance and signal quality control than by using only one of such parameters 1430.

By use of output means 1411 of said processing device 1404, output is established as parameter signals 1432, based on analysis output of said analyzing means 1410.

Concerning said identifying means 1408, the signal processing performed has been described for FIGS. 2, 3a, 3b, 3c, 4a, 4b, 5a, 5b, 6, and 7a. Details about General Methods Criteria 1421, Single Wave & Delta Wave Criteria 1424 and Time Sequence & Delta Time Sequence Criteria 1427 are already commented on in detail with reference to FIG. 2, and therefore these aspects are not commented on further in this context.

Said output means 1411 enables establishment of one or more pressure parameter signals 1432 related to a selectable number of said time sequence windows for outputting to said device terminal means 1412. A performance-modifying signal established from the regulator unit means 1414 is a function of one or more of said pressure parameter signals 1432. Said function is related to selectable criteria for said pressure parameter signals 1432.

Said selectable criteria are determined on basis of analysis output 1431 of a selectable number of included time sequence windows 1428. Exact thresholds for said time sequence (TS.x)-related parameters 1430 are not given, as they may be varied and should not therefore be considered to limit the scope of the invention. However, in order to illustrate aspects with such selectable criteria, a non-limitative example of criteria related to TS.MeanWavedP is shown in Table 10. Table 10 is directly comparable to Table 9.

TABLE 10

Selectable criteria related to TS.MeanWavedP.

| Processing device (analysis means) TS.MeanWavedP Threshold Criteria* | Processing device (output means) Parameter signal | Regulator unit means Performance-modifying signal |
|---|---|---|
| 1.0-3.0 mmHg | 0 | 0 |
| 3.0-4.0 mmHg | 1 | 1 |
| 4.0-5.0 mmHg | 2 | 2 |
| 5.0-7.0 mmHg | 3 | 3 |
| >7.0 mmHg | 4 | 4 |

*TS.MeanWavedP Threshold relates to a mean value of mean wave amplitude (TS.MeanWavedP) for a selectable number of said individual time sequence windows.

Since the parameter 1430 TS.MeanWavedP is highly predictable of cerebral compliance, criteria related to this parameter are very useful for controlling said regulator unit means 1414 and in turn said valve device 1413 for fluid drainage purposes. A major advantage is further obtained by combining criteria related to two or more of said parameters 1430, since such combinations increase the accuracy by which cerebral compliance in assessed and controlled. In addition, the accuracy of the process of including correct single pressure waves and time sequences windows containing cardiac beat-induced single pressure waves is increased.

Reference is now given to the eighth feature of this invention. This feature is further illustrated in FIG. 15, and also in FIG. 8.

Reference is now given to FIGS. 15a, 15b, 15c, and 15d. FIG. 15a shows an inventive device and modifications of the device are shown in FIGS. 15b, 15c, and 15d.

First, with reference to FIG. 15a, is shown an inventive device 1501 for use in sensing continuous pressure-related signals derivable from locations inside or outside a human or animal body or body cavity. The device 1501 comprises a pressure sensor 1502 with a pressure sensing element, a pressure transducer 1503 capable of transforming said pressure-related signals into digital pressure-related signals, a processing unit 1504 with input means for receiving said pressure-related digital signals, said processing unit 1504 providing at output means 1505 thereof one or more of the following time sequence parameters during selectable time sequence windows of said pressure-related signals: Mean wave amplitude (TS.MeanWavedP), mean wave latency (TS.MeanWavedT), mean wave rise time coefficient (TS.MeanWaveRT), mean amplitude (TS.MeandP), mean latency (TS.MeandT), mean rise time coefficient (TS.MeanRT), and mean single wave pressure (TS.Mean$_{SW}$P). Furthermore, a display unit 1506 connected to said output means 1505 for selectively displaying said one or more parameters, and means for supplying power 1507 to power consuming parts of the device.

The device can be modified so that the means for supplying power 1507 can be connected to external means for power supply 1507', e.g. via a cable to another external power source.

As shown in FIG. 15a, said pressure sensor 1502, said pressure transducer 1503, said processing unit 1504, said output means 1505, said display unit 1506 and said means for supplying power 1507 together can constitute a single physical unit forming a display device 1501.

In FIG. 15b is shown another variant of the device shown in FIG. 15a. According to the device 1508 shown in FIG. 15b, a pressure sensor 1509 is connectable to the device 1508 at an input 1510 thereof linked to a pressure transducer 1511. More specifically said device 1508 constitutes a single physical unit, comprising said pressure transducer 1511, a processing unit 1512, an output means 1513, a display unit 1514 and means 1515 for supplying power. Said pressure sensor 1509 is configured to be located in tissue or body cavity or enclosed fluid flow part of said human or animal body. Said single physical unit of said device 1508 is locatable below or on a skin surface of said human or animal body or spaced externally from the skin surface.

The device can be modified so that the means for supplying power 1515 can be connected to external means for power supply 1515', e.g. via a cable to another external power source.

In FIG. 15c is described another modification of said device 1501 already described in FIG. 15a. The device 1501 can include parameter data storage means and parameter selection control means.

Reference is now given to FIG. 15c, illustrating a device 1516 comprising a pressure sensor 1517, a pressure transducer 1518, a processing unit 1519, an output means 1520, a display unit 1521, parameter selection control means 1522, parameter storage means 1523, means 1524 for supplying power, these elements within the device 1516 together constitute a single physical unit.

The device can be modified so that the means 1524 for supplying power can be connected to external means for power supply 1524', e.g. via a cable to another external power source.

The combined sensor and display device 1516 constituting a single physical unit 1516 can as well, as an option, include information transfer means 1525. Information can be transferred from said information transfer means 1525 to an external unit 1526. Said transferal of information to an external unit 1526 relates to visual display of said information. Said external unit 1526 can be a multi-parameter vital signs monitor. When said device 1516 also incorporates said information transfer means 1525, said information transfer means 1525 is included in said single physical unit 1516.

Reference is now given to FIG. 15d, which is a modification of the device shown in FIG. 15c. In FIG. 15d is shown a device 1527 wherein a pressure sensor 1528 is connectable to said single physical unit 1527 at an input 1529 thereof linked to a pressure transducer 1530. The device 1527 shown in FIG. 15d comprises said pressure transducer 1530, a processing unit 1531, an output means 1532, a parameter selection control means 1533, a parameter storage means 1534, a display unit 1535, said means 1536 for supplying power, said elements within the unit 1527 together constituting said single physical unit 1527. Said pressure sensor 1528 is configured to be suitably located in tissue or body cavity or enclosed fluid flow part of said human or animal body, and wherein said single physical unit of said device 1527 is locatable below or on a skin surface of said human or animal body or spaced externally from the skin surface.

The device can be modified so that the means 1536 for supplying power can be connected to external means for power supply 1536', e.g. via a cable to another external power source.

The display device 1527 constituting a single physical unit 1527 can as well include information transfer means 1537. Information can be transferred from said information transfer means 1537 to an external unit 1538. Said transferal of information to an external unit 1538 relates to visual display of said information. Said external unit 1538 can be a multi-parameter vital signs monitor. When said device 1527 also incorporates said information transfer means 1537, said information transfer means 1538 is also included in said single physical unit 1527.

With reference to FIGS. 15a, 15b, 15c, and 15d, said pressure sensors 1502, 1509, 1517, 1528 can be configured either to be located inside or outside a human or animal body or body cavity. Said sensor 1502, 1509, 1517, 1528 can either be configured for measuring pressures within a fluid or within a solid tissue. Said sensors 1509, 1528 can be located at a physical distance from said respective pressure transducer 1511, 1530 and processing unit 1512, 1531.

With reference to FIGS. 15a and 15b said means 1507, 1515 for supplying power could be a battery, e.g a rechargeable battery.

With reference to FIGS. 15c and 15d, said means 1524, 1536 for supplying power can receive power from a respective external unit 1526, 1538. Alternatively, said means for supplying power 1526, 1536 can be a battery, e.g. a rechargeable battery.

With reference to FIGS. 15a, 15b, 15c, and 15d said means 1507, 1515, 1524, 1536 for supplying power can be connected to external means for power supply 1507', 1515', 1524', 1536'. Such external means be a cable contact to external power sources.

With reference to FIGS. 15a, 15b, 15c, and 15d, said device 1501, 1508, 1516, and 1527 can be a self-contained system, or supplementary to an external multi-parameter display system as regards display of pressure related parameters.

The major significance with the devices described in FIGS. 15a, 15b, 15c, and 15d is that the inventive method of processing continuous pressure related signals can be directly displayed. Completely new information about pressures not revealed by currently used, though, prior art technology can be shown, enabling subsequent quick diagnosis to be made by an experienced physician, quit of intervention. The various modifications of the device provides for pressure measurements in many settings, from within the hospital department to the private home of a patient.

Reference is now given to the ninth feature of this invention. This feature is particularly illustrated in FIG. 16, and also in FIG. 8.

Reference is now given to FIGS. 16a, 16b, 16c, and 16d. It is shown an inventive device in FIG. 16a. Modifications of this device (FIG. 16a) are shown in FIGS. 16b, 16c, and 16d.

With reference to FIG. 16a, is shown a device 1601 for use in sensing continuous pressure-related signals derivable from locations inside or outside a human or animal body or body cavity, comprising a pressure sensor 1602 with a pressure sensing element, a pressure transducer 1603 capable of transforming said pressure-related signals into digital pressure-related signals, a processing unit 1604 with input means for receiving said pressure-related digital signals, said processing unit 1604 providing at output means 1605 thereof one or more of the following time sequence parameters during selectable time sequence windows of said pressure-related signals: Mean wave amplitude (TS.MeanWavedP), mean wave latency (TS.MeanWavedT), mean wave rise time coefficient (TS.MeanWaveRT), mean amplitude (TS.MeandP), mean latency (TS.MeandT), mean rise time coefficient (TS.MeanRT), and mean single wave pressure (TS.Mean$_{SW}$P). Information transfer means 1606 is connected to said output means 1605, and there is provided means 1607 for supplying power to power consuming parts within the device. Said information transfer means 1606 enables transferal of information to an external unit 1608 of at least said one or more parameters.

Transferal of information to an external unit 1608 can relate to visual display of said information, and wherein said external unit 1608 can be a multi-parameter vital signs monitor.

It is shown in FIG. 16a that said device 1601 comprising said pressure sensor 1602, said pressure transducer 1603, said processing unit 1604, said output means 1605, said information transfer means 1606 and said means for supplying power 1607 together constitute a single physical unit forming a sensor device 1601.

Reference is now given to FIG. 16b, to illustrate a device being a modification of the device shown in FIG. 16a. In FIG. 16b is shown a sensor device 1609, wherein the pressure sensor 1610 is connectable to the device 1609 at an input 1611 linked to said pressure transducer 1612. Said sensor device 1609 comprises elements in the form of a pressure transducer 1612, a processing unit 1613, an output means 1614, information transfer means 1615 and means 1616 for supplying power, said elements together constituting a single physical unit. Said pressure sensor 1610 can be located in tissue or body cavity or enclosed fluid flow part of said human or animal body. Said single physical unit forming said device 1609 is locatable below or on a skin surface of said human or animal body or spaced externally from said skin surface.

Reference is now given to FIG. 16c, to show another modification of the device 1601 shown in FIG. 16a. Said device 1601 is modified to further include a display unit 1623 connected to output means 1622 of a processing unit 1621 or linking said output means with information transfer means 1625.

In FIG. 16c is shown a combined sensor-display device 1618, wherein the elements included therein are a pressure sensor 1619, a pressure transducer 1620, a processing unit 1621, output means 1622, a display unit 1623, means 1624 for supplying power and information transfer means 1625 together constitute a single physical unit forming a sensor-display device 1618.

The device can be modified so that the means 1624 for supplying power can be connected to external means for power supply 1624', e.g. via a cable to another external power source.

In FIG. 16d is shown a device 1627 representing a modification of that shown in FIG. 16c. In FIG. 16d a pressure sensor 1628 is connectable to the device 1627 at an input 1629 thereof linked to a pressure transducer 1630. Said pressure transducer 1630 together with a processing unit 1631, output means 1632, display unit 1633, said means 1634 for supplying power and said information transfer means 1635 constitute a single physical unit 1627. Said pressure sensor 1628 can be configured to be suitable for location in tissue or body cavity or enclosed fluid flow part of said human or animal body. Said single physical unit of said device 1627 is locatable below or on a skin surface of said human or animal body or spaced externally from the skin surface.

The device can be modified so that the means 1634 for supplying power can be connected to external means for power supply 1634', e.g. via a cable to another external power source.

The sensor-display devices 1618, 1627 shown in FIGS. 16c and 16c, can further include parameter data storage means and parameter selection control means. The resulting devices have already been described in connection with FIGS. 15c and 15d, therefore further details are not given here. The devices 1516, 1527 described in FIGS. 15c and 15d are combined sensor-display devices.

With reference to FIGS. 16a, 16b, 16c, and 16d, said pressure sensor 1602, 1610, 1619, 1628 can be configured either to be located inside or outside a human or animal body or body cavity. Further, said sensors 1602, 1610, 1619, 1628 can either be configured for measuring pressures within a fluid or within a solid tissue. Suitably, the sensors 1610, 1628 can be located at physical distance from the respective pressure transducer 1612, 1630 and processing unit 1613, 1631.

With reference to FIGS. 16*a* and 16*b* said means 1607, 1616 for supplying power can be a battery, e.g. a rechargeable battery.

With reference to FIGS. 16*c* and 16*d*, said means 1624, 1634 for supplying power can receive power from said external unit 1626, 1636. Alternatively, said means 1624, 1634 can be a battery, e.g. a rechargeable battery.

With reference to FIGS. 16*a*, 16*b*, 16*c*, and 16*d*, said devices 1601, 1609, 1618, 1627 can each be used as an independent, self-contained sensor system. The devices 1618, 1627 can also provide parameter display, which will be supplementary to an externally located multi-parameter display system.

By means of the inventive devices described in FIGS. 16*a*, 16*b*, 16*c*, and 16*d* the inventive method of processing continuous pressure related signals can be incorporated directly within such sensor device, e.g. through use firmware or plug-in program related memory. Thereby the device can provide completely new information about pressures, as compared to current and prior art technology useful for diagnostic or monitoring purposed when viewed by a physician. For example, output from the device itself may be used to assess cerebral compliance without need for further or additional equipment. For example, simple equipment can be developed for diagnosing so-called normal pressure hydrocephalus (NPH). The sensor can measure pressure within the spinal cerebrospinal fluid (CSF) cavity, and the continuous pressure signals can be processed according to the inventive method, the output of the analysis can be displayed to the physician, thus allowing quick diagnosis based on the personal expertise of the physician. Thereby pressure related parameters and combination thereof have been made available through the invention, and can be subsequently viewed and evaluated by a physician for his/her determination of diagnosis or for mere status monitoring, even at locations outside hospital grounds, at an outpatient clinic or in field operations.

Reference is now given to the tenth feature of this invention. This feature is further illustrated in FIG. 17, and also in FIG. 8.

Figure 17:
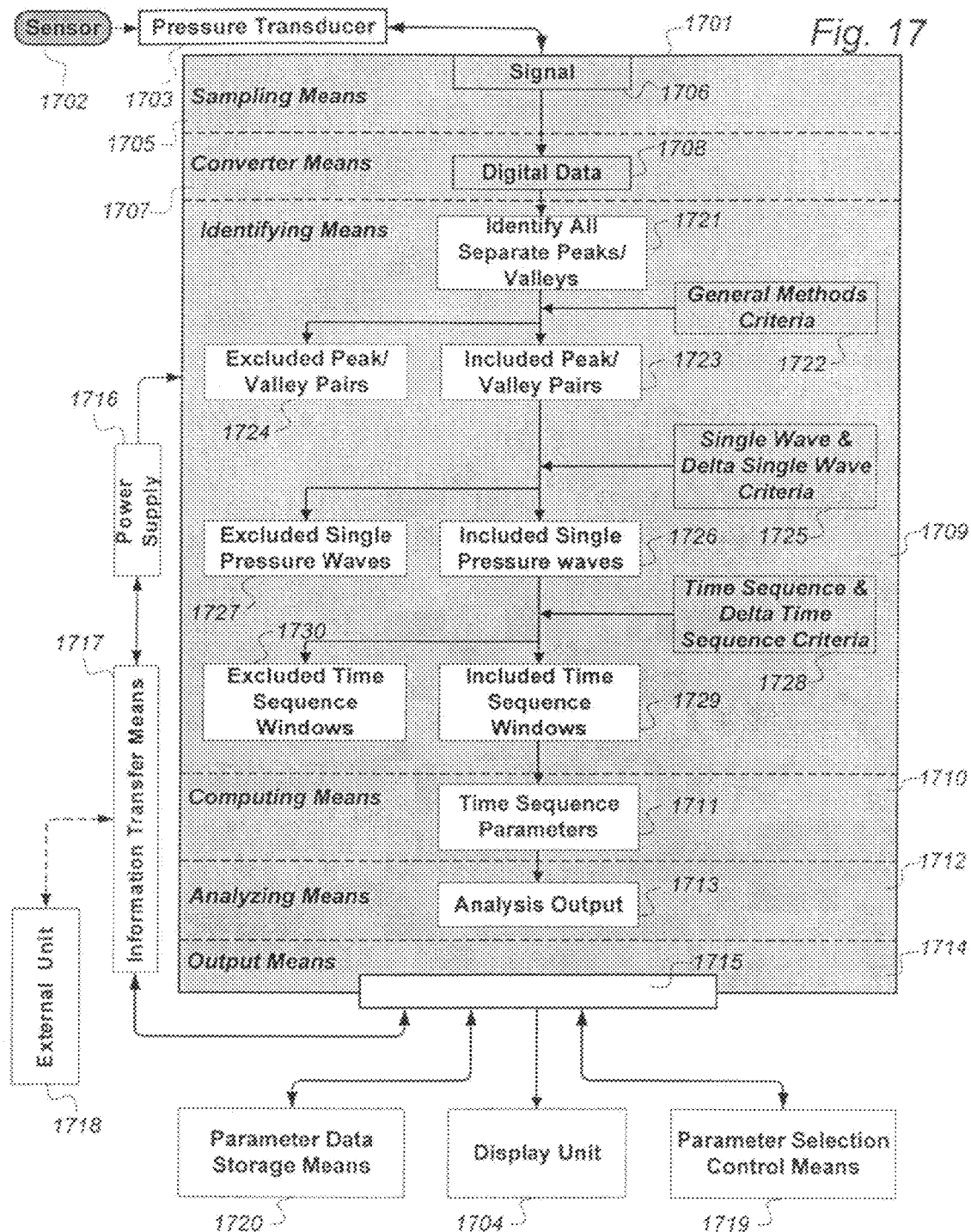
FIG. 17 shows a system for processing continuous pressure-related signals, used in sensing continuous pressure-related signals, and incorporated in sensor and/or display devices.

Reference is now given to FIG. 17. In FIG. 17 is shown a system for processing continuous pressure-related signals 1706 derivable from one or more sensor(s) 1702 configured to be suitable for location(s) inside or outside a body or body cavity of a human being. Said system comprises means for on basis of said signals 1706 receivable from said sensor(s) 1702 via pressure transducer means 1703 to display 1704 output of said processing, either on a display unit 1704 or an external unit 1718. A processing unit 1701 in said system comprises means for processing said signals 1706. The processing unit includes: (a) Sampling means 1705 for sampling said signals 1706 receivable from said pressure transducer means 1703 at specific intervals; (b) Converter means 1707 for converting the sampled signals 1706 received from said sampling means into pressure related digital data 1708 with a time reference; (c) Identifying means 1709 for during selectable time sequence windows identifying from said digital data 1708 output from said converter means 1707 single pressure waves related to cardiac beat-induced pressure waves, related to artifacts, or a combination of cardiac beat-induced waves and artifacts; (d) Computing means 1710 for computing time sequence parameters 1711 from included or selected time sequence windows output from said identifying means; (e) Analyzing means 1712 for analyzing said time sequence parameters 1711 in the form of digital data related to said selectable time sequence windows; (f) Output means 1714 for outputting to device terminal means 1715 one or more pressure parameters related to a selectable number of said time sequence windows: Mean wave amplitude (TS.MeanWavedP), mean wave latency (TS.MeanWavedT), mean wave rise time coefficient (TS.MeanWaveRT), mean amplitude (TS.MeandP), mean latency (TS.MeandT), mean rise time coefficient (TS.MeanRT), and mean single wave pressure (TS.Mean$_{SW}$P). Said system also includes means for supplying power 1716 to power consuming parts within the system.

Said system shown in FIG. 17 includes a display unit 1704 linked to said output means 1714 via terminal means 1715.

The system of FIG. 17 can be incorporated in many types of physical units forming sensor devices, display devices, or a combination of sensor and display devices. Some examples are given in FIGS. 15*a*, 15*b*, 15*c*, 15*d*, 16*a*, 16*b*, 16*c* and 16*d*, in which the processor unit with its output means corresponds to the processor unit 1701 in FIG. 17 with its included output means 1714.

A system comprising said pressure sensor 1702, said pressure transducer 1703, said processing unit 1701, said display unit 1704 and said means for supplying power 1716 can together constitute a single physical unit forming a display device. Such a physical unit forming a device is further described with reference to FIG. 15*a*.

A system comprising said pressure transducer 1703, said processing unit 1701, said display unit 1704 and said means for supplying power 1716 together can also constitute a single physical unit. In this situation said pressure sensor 1702 is connectable to said single physical unit at an input linked to said pressure transducer 1703. Said pressure sensor 1702 is configured to be suitably located in tissue or body cavity or enclosed fluid flow part of said human or animal body. Said single physical unit of said device is locatable below or on a skin surface of said human or animal body or spaced externally from the skin surface. Such a physical unit forming a device is further described in FIG. 15*b*.

Output means 1714 of said system shown in FIG. 17 can further be operative with information transfer means 1717, enabling display of said analysis output 1713 on an external unit 1718 connectable to said output means 1714 via the information transfer means 1717. Furthermore, output means 1714 of said system shown in FIG. 17 can further include or be co-operate with parameter selection control means 1719 and parameter data storage means 1720.

Transferal of information to an external unit 1718 can relate to visual display of said information, and for such purpose said external unit 1718 is suitably a multi-parameter vital signs monitor.

A system comprising said pressure sensor 1702, said pressure transducer 1703, said processing unit 1701, said display unit 1704, said means for supplying power 1716, said information transfer means 1717, said parameter selection control means 1718, and said parameter data storage means 1720 together can constitute a single physical unit forming a display and sensor device. Such a physical unit forming a device is further described in FIG. 15*c*.

Another system comprising said pressure transducer 1703, said processing unit 1701, said display unit 1704, said means for supplying power 1716, said information transfer means 1717, said parameter selection control means 1719, and said parameter data storage means 1720 together can constitute another single physical unit. In this situation, the pressure sensor 1702 is connectable to said single physical unit at an input thereof linked to said pressure transducer 1703. Said pressure sensor 1702 is configured to be suitably located in tissue or body cavity or enclosed fluid flow part of said human or animal body. Said single physical unit of said device is locatable below or on a skin surface of said human or animal body or spaced externally from the skin surface. Such a physical unit forming a device is further described in FIG. 15d.

A system comprising said pressure sensor 1702, said pressure transducer 1703, said processing unit 1701, said information transfer means 1717 and said means for supplying power 1716 together can constitute a single physical unit forming a sensor device. This single physical unit of said device is locatable below a skin surface of or non-invasively relative to said human or animal body. Such a single physical unit forming a sensor device is further described in FIG. 16a.

A system comprising said pressure transducer 1703, said processing unit 1701, said information transfer means 1717 and said means for supplying power 1716 together can constitute a single physical unit. The pressure sensor 1702 can be connectable to said single physical unit at an input linked to said pressure transducer 1703. The pressure sensor 1702 can be configured to be suitably located in tissue or body cavity or enclosed fluid flow part of said human or animal body, and the single physical unit of said device can be locatable below or on a skin surface of said human or animal body or spaced externally from the skin surface. Such a single physical unit forming a sensor device is further described in FIG. 16b.

Output means 1714 of said system shown in FIG. 17 can further be operative with a display unit 1704 connected to said output means 1714 of said processing unit 1701 or linking said output means 1714 with said information transfer means 1717 enabling connection to an optional external unit 1718. In this situation a system comprising said pressure sensor 1702, said pressure transducer 1703, said processing unit 1701, said display unit 1704, said means for supplying power 1716 and said information transfer means 1717 together can constitute a single physical unit forming a sensor device. Such a single physical unit forming a sensor device is further described in FIG. 16c.

A system comprising said pressure transducer 1703, said processing unit 1701, said display unit 1704, said means for supplying power 1716 and said information transfer means 1717 together can constitute a single physical unit. In this situation the pressure sensor 1702 is connectable to said single physical unit at an input thereof linked to said pressure transducer 1703. The pressure sensor 1702 can be located in tissue or body cavity or enclosed fluid flow part of said human or animal body, and the single physical unit of such device can be locatable below or on a skin surface of said human or animal body or spaced externally from the skin surface. Such a single physical unit forming a sensor device is further described in FIG. 16d.

With reference to the system described in FIG. 17, said pressure sensor 1702 can be configured to be located either inside or outside a human or animal body or body cavity. Furthermore, said pressure sensor 1702 can either be configured for measuring pressures within a fluid or configured for measuring pressures within a solid tissue. Said sensor 1702 can be located at a physical distance from said pressure transducer 1703 and processing unit 1701 when the sensor 1702 is connectable to the single physical unit which inter alia incorporates the pressure transducer 1703.

Said means for supplying power 1716 referred to in FIG. 17 can receive power from said external unit 1718 in the embodiment of FIGS. 15c, 15d, 16a-16d. Alternatively or in combination said means for supplying power 1716 can be a battery, e.g. a rechargeable battery.

The system described in FIG. 17 can be a self-contained system. The system, with reference to FIGS. 15a-15d, 16c and 16d provides for add-on of display to a display device in an external multi-parameter display system.

Said processing unit 1701 in said system provides for processing said signals 1706 according to the method described for FIGS. 2 and 8. With reference to previous descriptions related to FIGS. 2 and 8, a short overview of the inventive system for processing of continuous pressure signals 1701 is now given with reference to FIG. 17.

Using the identifying means 1709, the method provides for identification of all separate peaks and valleys 1721 in said sampled signal 1706. Each of said peaks is a sample with a pressure value and a time stamp or location, and each of said valleys is a sample with a pressure value and a time stamp or location. The result of applying General Methods Criteria 1722 is either included peak/valley pair combinations 1723 or excluded peak/valley pair combinations 1724.

After applying the Single Wave & Delta Single Wave Criteria 1725 to said included peak/valley pairs 1723, the output is either included single pressure waves 1726 or excluded pressure waves 1727. Said criteria 1725 relate to thresholds and ranges of single pressure wave (SW.x)-related parameters and delta single pressure wave ($\Delta$SW.x)-related parameters during time sequence windows.

After applying the Single Wave & Delta Single Wave Criteria 1725, included pair combinations of peak/valley pairs 1723 in said signal 1706 correspond to included single pressure waves 1726. Pair combinations of diastolic minimum pressure (SW.$P_{min1}$) and systolic maximum pressure (SW.$P_{max}$) characterize single pressure waves created by cardiac beat-induced pressure waves. Said criteria 1725 exclude for further analysis pressure waves (i.e. minimum-maximum pressure (SW.$P_{min1}$/SW.$P_{max}$) pairs) during said time sequence windows with said single pressure wave (SW.x)- and delta single pressure wave ($\Delta$SW.x)-related parameters outside selected criteria for thresholds and ranges of said parameters. Said criteria 1725 include for further analysis single pressure waves 1726 having single pressure wave (SW.x)- and delta single pressure wave ($\Delta$SW.x)-related parameters within selected criteria for thresholds and ranges of said single pressure wave (SW.x)-related parameters. Pair combinations of diastolic minimum pressure (SW.$P_{min1}$) and systolic maximum pressure (SW.$P_{max}$) correspond to diastolic minimum pressures and systolic maximum pressures of individual of pressure waves created by each of said cardiac beats.

In order to further evaluate the included single pressure waves 1726, Time Sequence & Delta Time Sequence Criteria 1728 are applied to each of said time sequence windows in a continuous series of said time sequence windows. Each time sequence window is a selected time frame of said signal 1706. Said criteria 1728 for thresholds and ranges of said time sequence (TS.x) and delta time sequence ($\Delta$TS.x)-related parameters determine included time sequence windows 1729 and excluded time sequence windows 1730. Said criteria 1728 exclude for further analysis time sequence windows 1730 with time sequence (TS.x)- and delta time sequence ($\Delta$TS.x)-related parameters outside selected criteria for thresholds and ranges of said parameters. Said criteria 1728 include for further analysis time sequence windows 1729 having time sequence (TS.x) and delta time sequence ($\Delta$TS.x)-related parameters within selected criteria for thresholds and ranges of said time sequence (TS.x) and delta time sequence ($\Delta$TS.x)-related parameters.

Using said computing means 1710, time sequence (TS.x)-related parameters 1711 are computed for each individual of said included time sequence windows 1729. Such procedure is applied to each of said included time sequence windows 1729 in a continuous series of said time sequence windows. Using said computing means 1710, time sequence (TS.x)-related parameters 1711 from included time sequences windows 1729 are computed, said parameters can be selected from the group of:

mean value of starting diastolic minimum pressures of a time sequence window (TS.MeanP$_{min1}$), standard deviation of mean value of starting diastolic minimum pressures of a time sequence window (TS.MeanP$_{min1}$_STD), mean value of systolic maximum pressures of a time sequence window (TS.MeanP$_{max}$), standard deviation of mean value of systolic maximum pressures of a time sequence window (TS.MeanP$_{max}$_STD), mean amplitude of a time sequence window (TS.MeandP), standard deviation of mean amplitude of a time sequence window (TS.MeandP_STD), mean latency of a time sequence window (TS.MeandT), standard deviation of mean latency of a time sequence window (TS.MeandT_STD), mean rise time coefficient of a time sequence window (TS.MeanRT), standard deviation of mean rise time coefficient of a time sequence window (TS.MeanRT_STD), mean wave duration of a time sequence window (TS.MeanWD), standard deviation of mean wave duration of a time sequence window (TS.MeanWD_STD), mean single wave pressure of a time sequence window (TS.Mean$_{SW}$P), standard deviation of mean single wave pressure of a time sequence window (TS.Mean$_{SW}$P_STD), mean of diastolic minimum pressure differences of a time sequence window (TS.MeanDiff_P$_{min}$), standard deviation of mean of diastolic minimum pressure differences of a time sequence window (TS.MeanDiff_P$_{min}$_STD), mean of systolic maximum pressure differences of a time sequence window (TS.MeanDiff_P$_{max}$), standard deviation of mean of systolic maximum pressure differences of a time sequence window (TS.MeanDiff_P$_{max}$_STD), mean amplitude difference of a time sequence window (TS.MeanDiff_dP), standard deviation of mean amplitude difference of a time sequence window (TS.MeanDiff_dP_STD), mean latency difference of a time sequence window (TS.MeanDiff_dT), standard deviation of mean latency difference of a time sequence window (TS.MeanDiff_dT_STD), mean rise time coefficient difference of a time sequence window (TS.MeanDiff_RT), standard deviation of mean rise time coefficient difference of a time sequence window (TS.MeanDiff_RT_STD), mean wave duration difference of a time sequence window (TS.MeanDiff_WD), standard deviation of mean wave duration difference of a time sequence window (TS.MeanDiff_WD_STD), mean single wave pressure difference of a time sequence window (TS.MeanDiff_Mean$_{SW}$P), standard deviation of mean single wave pressure difference of a time sequence window (TS.MeanDiff_Mean$_{SW}$P_STD), numbers of accepted single pressure waves of a time sequence window (TS.SWCount), mean wave amplitude of a time sequence window computed according to the first matrix (TS.MeanWavedP), mean wave latency of a time sequence window computed according to the first matrix (TS.MeanWavedT), mean wave rise time coefficient of a time sequence window computed according to the second matrix (TS.MeanWaveRT).

The methods for computing said parameters 1711 have already been described in detail with reference to FIGS. 2 and 8. Any of said time sequence (TS.x)-related parameters 1711 can be used to create said analysis output 1713 from an analyzing means 1712. Concerning the system described in FIG. 17, in a preferred mode of the invention it has been found that the following parameters are most useful: Mean wave amplitude (TS.MeanWavedP), mean wave latency (TS.MeanWavedT), mean wave rise time coefficient (TS.MeanWaveRT), mean amplitude (TS.MeandP), mean latency (TS.MeandT), mean rise time coefficient (TS.MeanRT), and mean single wave pressure (TS.Mean$_{SW}$P).

There are several major advantages with computing one or more of said parameters:

Compliance within a brain or spinal body cavity can be assessed from the expertise of a qualified physician by his/her studying of parameters such as e.g.: TS.MeanWavedP, TS.MeanWavedT, TS.MeanWaveRT, TS.MeandP, TS.MeandT, and (TS.MeanRT). This is not possible by currently use, prior art technology. The inventive system provides the physician with useful aids by making available for new information not available with currently used, and prior art technology, thus enabling also more comprehensive and relevant monitoring of pressure related signals and render in the end a safer diagnosis of a patient to be made by a physician. However, neither the inventive methods disclosed herein, nor the devices/systems disclosed will in any way and by themselves be able to provide any diagnosis of an illness or a physical defect, e.g. in the brain. Thus, the pressure related parameters which are output to a display, possibly through an elevated selection of just some pressure related parameters, will provide the physician with aids which must be further proceed by him/her to provide an expert diagnosis.

The quality of the pressure signals can be assessed by parameters, e.g. such as TS.MeanPmin1_STD, TS.MeanP$_{max}$_STD, TS.MeandP_STD, TS.MeandT_STD, TS.MeanRT_STD, TS.MeanWD_STD, TS.MeanDiff_P$_{min}$_STD, TS.MeanDiff_P$_{max}$_STD, TS.MeanDiff_dP_STD, TS.MeanDiff_dT_STD, TS.MeanDiff_RT_STD, and TS.MeanDiff_WD_STD. It is very important to quality control the signals since bad signal quality increases the risk of not identifying cardiac beat-induced single pressure waves. Such quality control is not possible with current, prior art technology. Thus, the risk of obtaining misleading and false pressure measurements is made minimal by using the provisions made available through the present invention.

The output of said identifying means 1709 is included time sequence windows 1729 wherein said time sequence windows are included the best possible way. This means that these time sequence windows 1729 contain single pressure waves related to cardiac beat-induced pressure waves, not to artifacts or a combination of artifacts and cardiac beat-induced pressure waves. Thereby the risk of computing false or misleading time sequence (TS.x)-related parameters is made minimal. This is very important when e.g. a sensor is implanted on permanent basis into a body or body cavity. It is crucial to control that the signals measured are good and that the measured pressures actually are predictive for the pressures within the body or body cavity.

Concerning said identifying means 1709 the processing performed thereby is identical to the process described for FIGS. 2, 3a, 3b, 3c, 4a, 4b, 5a, 5b, 6, and 7a. Details about General Methods Criteria 1722, Single Wave & Delta Wave Criteria 1725 and Time Sequence & Delta Time Sequence Criteria 1728 are already commented on in detail with reference to FIG. 2, and therefore these aspects are not commented on further in this context.

It will be readily understood that a processing unit 1701 with output means 1714 included therein and in the form of e.g. a personal desk-top or lap-top computer could be used for implementing the operational functions 1721-1729, 1711 and 1713 through use of software loaded into the computer in a conventional manner. However, with smaller physical dimension of such processor and output means, the operational functions would suitably be provided through use of firmware or use of plug-in program memory.

If the display unit 1506, 1514, 1525, 1537, 1625, 1635 or 1704 has a display in the form of a touch screen, the parameter selection control means could partly be provided through a selection device operable from using the touch screen.

The invention claimed is:

1. A method for processing continuous pressure-related signals derivable from locations inside or outside a human or animal body or body cavity, comprising the steps of obtaining samples of said signals at specific intervals, and converting thus sampled pressure signals into pressure-related digital data with a time reference, wherein for selectable time sequence windows the method comprises the further steps of:
   a) identifying in a processing unit from said digital data single pressure waves related to cardiac beat-induced pressure waves,
   b) identifying in the processing unit from said digital data pressure waves related to artifacts or a combination of artifacts and cardiac beat-induced pressure waves,
   c) computing in the processing unit time sequence (TS.x)-related parameters of said single pressure waves during individual of said time sequence windows,
   d) adjusting by the processing unit said time sequence (TS.x)-related parameters of said single pressure waves during individual of said time sequence windows using formula-based adjustments based on related time sequence (rTS.x) parameters,
   e) creating in the processing unit from said formula-based adjustments factorized time sequence (fTS.x) parameters of said individual time sequence windows of said continuous pressure-related signals, and
   f) establishing and presenting by the processing unit an analysis output selected from one or more of said factorized time sequence (fTS.x)-related parameters of said single pressure waves during individual of said time sequence windows, wherein said related time sequence (rTS.x) parameters can be selected from the group of:
   relationship of mean values of starting diastolic minimum pressure of two or more perfect time sequence windows from two or more different pressure signals (rTS.$P_{min}$),
   relationship of standard deviation of mean values of starting diastolic minimum pressure of two or more perfect time sequence windows from two or more different pressure signals (rTS.MeanP$_{min1}$_STD),
   relationship of mean values of systolic maximum pressure of two or more perfect time sequence windows from two or more different pressure signals (rTS.MeanP$_{max}$),
   relationship of standard deviation of mean values of systolic maximum pressure of two or more perfect time sequence windows from two or more different pressure signals (rTS.MeanP$_{max}$_STD),
   relationship of mean amplitude values of two or more perfect time sequence windows from two or more different pressure signals (rTS.MeandP),
   relationship of standard deviation of mean amplitude of two or more perfect time sequence windows from two or more different pressure signals (rTS.MeandP_STD),
   relationship of mean latency of two or more perfect time sequence windows from two or more different pressure signals (rTS.MeandT),
   relationship of standard deviation of mean latency of two or more perfect time sequence windows from two or more two different pressure signals (rTS.MeandT_STD),
   relationship of mean rise time coefficient of two or more perfect time sequence windows from two or more different pressure signals (rTS.MeanRT),
   relationship of standard deviation of mean rise time coefficient of two or more perfect time sequence windows from two or more different pressure signals (rTS.MeanRT_STD),
   relationship of mean wave duration of two or more perfect time sequence windows from two or more different pressure signals (rTS.MeanWD),
   relationship of standard deviation of mean wave duration of two or more perfect time sequence windows from two or more different pressure signals (rTS.MeanWD_STD),
   relationship of mean single wave pressure of two or more perfect time sequence windows from two or more different pressure signals (rTS.Mean$_{sw}$P),
   relationship of standard deviation of mean single wave pressure of two or more perfect time sequence windows from two or more different pressure signals (rTS.Mean$_{sw}$ P_STD),
   relationship of mean diastolic minimum pressure difference of two or more perfect time sequence windows from two or more different pressure signals (rTS.MeanDiff_P$_{min}$),
   relationship of standard deviation of mean diastolic minimum pressure difference of two or more perfect time sequence windows from two or more different pressure signals (rTS.MeanDiff_P$_{min}$_STD),
   relationship of mean systolic maximum pressure difference of two or more perfect time sequence windows from two or more different pressure signals (rTS.MeanDiff_P$_{max}$),
   relationship of standard deviation of mean systolic maximum pressure difference of two or more perfect time sequence windows from two or more different pressure signals (rTS.MeanDiff_P$_{max}$_STD),
   relationship of mean amplitude difference of two or more perfect time sequence windows from two or more different pressure signals (rTS.MeanDiff_dP),
   relationship of standard deviation of mean amplitude difference of two or more perfect time sequence windows from two or more different pressure signals (rTS.MeanDiff_dP_STD),
   relationship of mean latency difference of two or more perfect time sequence windows from two or more different pressure signals (rTS.MeanDiff_dT),
   relationship of standard deviation of mean latency difference of two or more perfect time sequence windows from two or more different pressure signals (rTS.MeanDiff_dT_STD), relationship of mean rise time coefficient difference of two or more perfect time sequence windows from two or more different pressure signals (rTS.MeanDiff_RT), relationship of standard deviation of mean rise time coefficient difference of two or more perfect time sequence windows from two or more different pressure signals (rTS.MeanDiff_RT_STD), relationship of mean wave duration difference of two or more perfect time sequence windows from two or more different pressure signals (rTS.MeanDiff_WD), relationship of standard deviation of mean wave duration difference of two or more perfect time sequence windows from two or more two different pressure signals (rTS.MeanDiff_WD_STD), relationship of mean single wave pressure difference of two or more perfect time sequence windows from two or more different pressure signals (rTS.MeanDiff_ Mean$_{sw}$P), relationship of standard deviation of mean single wave pressure difference of two or more perfect time sequence windows from two or more two different pressure signals (rTS.MeanDiff_Mean$_{sw}$P_STD), relationship of single wave count of two or more perfect time sequence windows from two or more different pressure signals (rTS.SWCount), relationship of mean wave amplitude of two or more perfect time sequence windows from two or more different pressure signals (rTS.MeanWavedP), relationship of mean wave latency of two or more perfect time sequence windows from two or more different pressure signals (rTS.MeanWavedT), and relationship of mean wave rise time coefficient of two or more perfect time sequence windows from two or more different pressure signals (rTS.MeanWaveRT).

2. The method according to claim 1, wherein said pressure-related signals relate to human or animal body pressures elected from one or more of: intracranial pressure, arterial blood pressure, or ocular pressure.

3. The method according to claim 1, wherein said pressure-related signals are transcranial Doppler signals, being transformable into pressure-related signals indicative of intracranial pressure signals.

4. The method according to claim 1, wherein said pressure related signals are cranial impedance-related signals, being transformable into pressure-related signals indicative of intracranial pressure signals.

5. The method according to claim 1, wherein said pressure related signals are related to air pressure signals derivable from within outlet-sealed outer ear channel of a human or animal, said air pressure signals being transformable into pressure-related signals indicative of intracranial pressure signals.

6. The method according to claim 1, wherein said pressure related signals are fontanel applanation pressure signals, being transformable into pressure-related signals indicative of intracranial pressure signals.

7. The method according to claim 1, wherein said pressure related signals are ocular applanation pressure signals, being transformable into pressure-related signals indicative of intra-ocular pressure signals.

8. The method according to claim 1, wherein said pressure related signals are arterial applanation pressure signals, being transformable into pressure-related signals indicative of intra-arterial pressure signals.

9. The method according to claim 1, wherein each of said selectable time sequence windows is a selected time frame of said pressure-related digital data with a time reference, each of said selected time frame lying in the range 5-15 seconds.

10. The method according to claim 1, wherein each of said selectable time sequence windows is related to a number of time-related sequential pressure samples, each sample identifiable by a sample number and elapsed time determined by sample location number and sample frequency.

11. The method according to claim 1, wherein the method is applied to each of said time sequence windows in a continuous series of said time sequence windows during a recording.

12. The method according to claim 1, wherein said computing step c) for included time sequence windows further includes determining said time sequence (TS.x)-related parameters, said parameters selected from the group of:

c1) mean value of starting diastolic minimum pressures of a time sequence window (TS.MeanP$_{min1}$), c2) standard deviation of mean value of starting diastolic minimum pressures of a time sequence window (TS.MeanP$_{min1}$_STD), c3) mean value of systolic maximum pressures of a time sequence window (TS.MeanP$_{max}$), c4) standard deviation of mean value of systolic maximum pressures of a time sequence window (TS.MeanP$_{max\_}$STD), c5) mean amplitude of a time sequence window (TS.MeandP), c6) standard deviation of mean amplitude of a time sequence window (TS.MeandP_STD), c7) mean latency of a time sequence window (TS.MeandT), c8) standard deviation of mean latency of a time sequence window (TS.MeandT_STD), c9) mean rise time coefficient of a time sequence window (TS.MeanRT), c10) standard deviation of mean rise time coefficient of a time sequence window (TS.MeanRT_STD), c11) mean wave duration of a time sequence window (TS.MeanWD), c12) standard deviation of mean wave duration of a time sequence window (TS.MeanWD_STD), c13) mean single wave pressure of a time sequence window (TS.Mean$_{sw}$P), c14) standard deviation of mean single wave pressure of a time sequence window (TS.Mean$_{sw}$P_STD), c15) mean of diastolic minimum pressure differences of a time sequence window (TS.MeanDiff_P$_{min}$), c16) standard deviation of mean of diastolic minimum pressure differences of a time sequence window (TS.MeanDiff_P$_{min\_}$STD), c17) mean of systolic maximum pressure differences of a time sequence window (TS.MeanDiff_P$_{max}$), c18) standard deviation of mean of systolic maximum pressure differences of a time sequence window (TS.MeanDiff_P$_{max\_}$STD), c19) mean amplitude difference of a time sequence window (TS.MeanDiff_dP), c20) standard deviation of mean amplitude difference of a time sequence (TS .MeanDiff_dP_STD), c21) mean latency difference of a time sequence window (TS.MeanDiff_dT), c22) standard deviation of mean latency difference of a time sequence window (TS.MeanDiff_dT_STD), c23) mean rise time coefficient difference of a time sequence window (TS.MeanDiff_RT), c24) standard deviation of mean rise time coefficient difference of a time sequence window (TS.MeanDiff_RT_STD),
c25) mean wave duration difference of a time sequence window (TS.MeanDiff_WD),
c26) standard deviation of mean wave duration difference of a time sequence window (TS.MeanDiff_WD_STD),
c27) mean single wave pressure difference of a time sequence window (TS.MeanDiff_Mean$_{sw}$P),
c28) standard deviation of mean single wave pressure difference of a time sequence window (TS.MeanDiff_Mean$_{sw}$P_STD),
c29) number of accepted single pressure waves of a time sequence window (TS.SWCount),
c30) mean wave amplitude of a time sequence computed according to a first matrix (TS.MeanWavedP),
c31) mean wave latency of a time sequence computed according to a first matrix (TS.MeanWavedT),
c32) mean wave rise time coefficient of a time sequence computed according to a second matrix (TS.MeanWaveRT).

13. The method according to claim 1, wherein said perfect time sequence windows imply time sequences accepted after application of very strict criteria.

14. The method according to claim 1, wherein said formula-based adjustments based on related time sequence (rTS.x) parameters refer to constant relationships and/or formula-based relationships between identical time sequence (TS.x)-related parameters.

15. The method according to claim 1, wherein said formula-based adjustments of time sequence (TS.x)-related parameters relate to multiplication of the pressure scale of said individual time sequence windows of said pressure-related signal with a given constant factor value derived from the related time sequence (rTS.x) parameters.

16. The method according to claim 1, wherein said formula-based adjustments of time sequence (TS.x)-related parameters relate to adjustment of the pressure scale of said individual time sequence windows of said pressure-related signal according to a formula-based relationship derived from the related time sequence (rTS.x) parameters.

17. The method according to claim 1, wherein said related time sequence (rTS.x) parameters are derived from a database, and represent a historical material of known relationships.

18. The method according to claim 1, wherein said related time sequence (rTS.x) parameters are determined for a population of recordings, said population including selectable recordings, each including one or more simultaneous continuous pressure-related signals, and wherein said population of recordings enables determination of population-based formulas for said related time sequence (rTS.x)-related parameters.

19. The method according to claim 1, wherein said factorized time sequence (fTS.x) parameters of step e) are selected from the group of:
factorized mean value of starting diastolic minimum pressure of a time sequence window (fTS.MeanP$_{min1}$),
factorized standard deviation of mean value of starting diastolic minimum pressure of a time sequence window (fTS.MeanP$_{min1}$_STD),
factorized mean value of systolic maximum pressure of a time sequence window (fTS.MeanP$_{max}$),
factorized standard deviation of mean value of systolic maximum pressure of a time sequence window (fTS.MeanP$_{max}$_STD),
factorized mean amplitude of a time sequence window (fTS.MeandP),
factorized standard deviation of mean amplitude of a time sequence window (fTS.MeandP_STD),
factorized mean latency of a time sequence window (fTS.MeandT),
factorized standard deviation of mean latency of a time sequence window (fTS.MeandT_STD),
factorized mean rise time coefficient of a time sequence window (fTS.MeanRT),
factorized standard deviation of mean rise time coefficient of a time sequence window (fTS.MeanRT_STD),
factorized mean wave duration of a time sequence window (fTS.MeanWD),
factorized standard deviation of mean wave duration of a time sequence window (fTS.MeanWD_STD),
factorized mean single wave pressure of a time sequence window (fTS.Mean$_{sw}$P),
factorized standard deviation of mean single wave pressure of a time sequence window (fTS.Mean$_{sw}$P_STD),
factorized mean value of diastolic minimum pressure difference of a time sequence window (fTS.MeanDiff_P$_{min}$),
factorized standard deviation of mean value of diastolic minimum pressure difference of a time sequence window (fTS.MeanDiff_P$_{min}$_STD),
factorized mean value of systolic maximum pressure difference of a time sequence window (fTS.MeanDiff_P$_{max}$),
factorized standard deviation of mean value of systolic maximum pressure difference of a time sequence window (fTS.MeanDiff_P$_{max}$_STD),
factorized mean amplitude difference of a time sequence window (fTS.MeanDiff_dP),
factorized standard deviation of mean amplitude difference of a time sequence window (fTS.MeanDiff_dP_STD),
factorized mean latency difference of a time sequence window (fTS.MeanDiff_dT),
factorized standard deviation of mean latency difference of a time sequence window (fTS.MeanDiff_dT_STD),
factorized mean rise time coefficient difference of a time sequence window (fTS.MeanDiff_RT),
factorized standard deviation of mean rise time coefficient difference of a time sequence window (fTS.MeanDiff_RT_STD),
factorized mean wave duration difference of a time sequence window (fTS.MeanDiff_WD),
factorized standard deviation of mean wave duration difference of a time sequence window (fTS.MeanDiff_WD_STD),
factorized standard deviation of mean single wave pressure difference of a time sequence window (fTS.MeanDiff_Mean$_{sw}$P_STD),
factorized amplitude of the mean wave of a time sequence window (fTS.MeanWavedP),
factorized latency of the mean wave of a time sequence window (fTS.MeanWavedT), and
factorized rise time coefficient of the mean wave of a time sequence window (fTS.MeanWaveRT).

20. The method according to claim 1, wherein said creating step f) yields output of factorized time sequence (fTS.x) parameters of said individual time sequence windows in a continuous series of said time sequence windows of said pressure-related signal.

21. The method according to claim 1, wherein the duration of each selectable time sequence window lies in a time range of 5-15 seconds.

22. The method according to claim 1, wherein said pressure related signals are applanation pressure signals, being transformable into pressure-related signals indicative of intra-arterial pressure signals.

23. The method according to claim 22, wherein said applanation pressure signals are arterial applanation pressure signals.

* * * * *